US011642407B2

(12) United States Patent
Ricke

(10) Patent No.: US 11,642,407 B2
(45) Date of Patent: May 9, 2023

(54) IDENTIFICATION OF VARIABLE INFLUENZA RESIDUES AND USES THEREOF

(71) Applicant: Massachusetts Institute of Technology, Cambridge, MA (US)

(72) Inventor: Darrell O. Ricke, Winchester, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 17/186,851

(22) Filed: Feb. 26, 2021

(65) Prior Publication Data

US 2021/0379179 A1 Dec. 9, 2021

Related U.S. Application Data

(60) Provisional application No. 62/983,519, filed on Feb. 28, 2020.

(51) Int. Cl.

| | |
|---|---|
| ***A61K 39/145*** | (2006.01) |
| ***A61K 39/12*** | (2006.01) |
| *A61K 31/16* | (2006.01) |

(52) U.S. Cl.

CPC ............ *A61K 39/145* (2013.01); *A61K 39/12* (2013.01); *A61K 31/16* (2013.01)

(58) Field of Classification Search

CPC ........ A61K 39/12; A61K 39/145; A61P 31/16

See application file for complete search history.

(56) References Cited

U.S. PATENT DOCUMENTS

| | | | | |
|---|---|---|---|---|
| 9,017,694 | B2 * | 4/2015 | Jin | C07K 14/005 435/235.1 |
| 10,905,756 | B2 * | 2/2021 | Eichmeyer | A61K 39/12 |
| 2012/0014972 | A1 | 1/2012 | Hodges et al. | |

FOREIGN PATENT DOCUMENTS

| | | | | |
|---|---|---|---|---|
| EP | 3730620 | | 10/2020 | |
| WO | 2008/157419 | | 12/2008 | |
| WO | 2010125461 | * | 11/2010 | A61K 39/145 |
| WO | 2018/078053 | | 5/2018 | |
| WO | 2014/141125 | | 9/2018 | |
| WO | WO20191455475 | * | 1/2019 | A61K 39/0011 |
| WO | 2019/124557 | | 6/2019 | |
| WO | 2019/246363 | | 12/2019 | |
| WO | 2020/061443 | | 3/2020 | |

OTHER PUBLICATIONS

Korsun, et al. (2020) "Genetic diversity of influenza A viruses circulating in Bulgaria during the 2018-2019 winter season," Journal of Medical Microbiology 2020;69:986-998.

Liu, et al., (2021) "Molecular evolution and characterization of hemagglutinin and neuraminidase of influenza A(H1N1) pdm09 viruses isolated in Beijing, China, during the 2017-2018 and 2018-2019 influenza seasons," Archives of Virology (2021) 166:179-189.

Opanda, et al., (2020) "Assessing antigenic drift and phylogeny of influenza A (H1N1) pdm09 virus in Kenya using HA1 sub-unit of the hemagglutinin gene," PLoS ONE 15(2): e0278029.

Zolotarova. et al., (2019) "Antigenic Site Variation in the Hemagglutinin of Pandemic Influenza A(H1N1)pdm09 Viruses between 2009-2017 in Ukraine," Pathogens 2019, 8 (194): 1-13.

International Search Report for PCT/US2021/019864, dated Jun. 30, 2021.

* cited by examiner

*Primary Examiner* — Bao Q Li

(74) *Attorney, Agent, or Firm* — McDonnell Boehnen Hulbert & Berghoff

(57) ABSTRACT

Provided herein are universal prophylactic compositions for preventing infection with influenza viruses by directing the immune response to highly conserved regions of the virus. Also provided are universal therapeutic compositions for treating influenza infection by targeting the highly conserved regions. Methods for using the prophylactic and therapeutic compositions are also provided.

18 Claims, 5 Drawing Sheets

Specification includes a Sequence Listing.

```
    M  K  A  I  L  V  V  L  L  Y  T  F  T  T  A  N  A  D  T  L
1   atgaaggcaatactagtagttctgctatatacatttacaaccgcaaatgcagacacatta 60

    C  I  G  Y  H  A  N  N  S  T  D  T  V  D  T  V  L  E  K  N
61  tgtataggttatcatgcgaacaattcaacagacactgtagacacagtactagaaaagaat 120

    V  T  V  T  H  S  V  N  L  L  E  D  K  H  N  G  K  L  C  K
121 gtaacagtaacacactctgttaaccttctggaagacaagcataacggaaaactatgcaaa 180

    L  R  G  V  A  P  L  H  L  G  K  C  N  I  A  G  W  I  L  G
181 ctaagaggggtagccccattgcatttgggtaaatgtaacattgctggctggatcctggga 240

    N  P  E  C  E  S  L  S  T  A  S  S  W  S  Y  I  V  E  T  S
241 aatccagagtgtgaatcactctccacagcaagttcatggtcctacattgtggaaacatct 300

    N  S  D  N  G  T  C  Y  P  G  D  F  I  N  Y  E  E  L  R  E
301 aattcagacaatggaacgtgttacccaggagatttcatcaattatgaggagctaagagag 360

    Q  L  S  S  V  S  S  F  E  R  F  E  I  F  P  K  T  S  S  W
361 caattgagctcagtgtcatcatttgaaaggtttgagatattccccaagacaagttcatgg 420

    P  N  H  D  S  N  K  G  V  T  A  A  C  P  H  A  G  A  K  S
421 cccaatcatgactcgaacaaaggtgtaacggcagcatgtcctcacgctggagcaaaaagc 480

    F  Y  K  N  L  I  W  L  V  K  K  G  N  S  Y  P  K  L  N  Q
481 ttctacaaaaacttgatatggctagttaaaaaggaaattcatacccaaagcttaaccaa 540

    S  Y  I  N  D  K  G  K  E  V  L  V  L  W  G  I  H  H  P  S
541 tcctacattaatgataaagggaaagaagtcctcgtgctgtggggcattcaccatccatct 600

    T  T  A  D  Q  Q  S  L  Y  Q  N  A  D  A  Y  V  F  V  G  T
601 actactgctgaccaacaaagtctctatcagaatgcagatgcatatgtttttgtggggaca 660
```

FIG. 2

```
     S  R  Y  S  K  K  F  K  P  E  I  A  T  R  P  K  V  R  D  Q
661  tcaagatacagcaagaagttcaagccggaaatagcaacaagacccaaagtgagggatcaa  720

     E  G  R  M  N  Y  Y  W  T  L  V  E  P  G  D  K  I  T  F  E
721  gaagggagaatgaactattactggacactggtagagccgggggacaaaataacattcgaa  780

     A  T  G  N  L  V  V  P  R  Y  A  F  T  M  E  R  N  A  G  S
781  gcaactggaaatctagtggtaccgagatatgcattcacaatggaaagaaatgctggatct  840

     G  I  I  I  S  D  T  P  V  H  D  C  N  T  T  C  Q  T  P  E
841  ggtattatcatttcagatacaccagtccacgattgcaatacaacttgtcagacacccgag  900

     G  A  I  N  T  S  L  P  F  Q  N  I  H  P  I  T  I  G  K  C
901  ggtgctataaacaccagcctcccctttcaaaatatacatcccatcacaattggaaaatgt  960

     P  K  Y  V  K  S  T  K  L  R  L  A  T  G  L  R  N  V  P  S
961  ccaaagtatgtaaaaagcacaaaattgagactggccacaggattgaggaatgttccgtct  1020

     I  Q  S  R  G  L  F  G  A  I  A  G  F  I  E  G  G  W  T  G
1021 attcaatctagaggcctattcggggccattgccggcttcattgaaggggggtggacaggg  1080

     M  V  D  G  W  Y  G  Y  H  H  Q  N  E  Q  G  S  G  Y  A  A
1081 atggtagatggatggtacggttatcaccatcaaaatgagcaggggtcaggatatgcagcc  1140

     D  L  K  S  T  Q  N  A  I  D  K  I  T  N  K  V  N  S  V  I
1141 gacctgaagagcacacaaaatgccattgacaagattactaacaaagtaaattctgttatt  1200

     E  K  M  N  T  Q  F  T  A  V  G  K  E  F  N  H  L  E  K  R
1201 gaaaagatgaatacacagttcacagcagtgggtaaagagttcaaccacctggaaaaaaga  1260

     I  E  N  L  N  K  K  V  D  D  G  F  L  D  I  W  T  Y  N  A
1261 atagagaatctaaataaaaaagttgatgatggtttcctggacatttggacttacaatgcc  1320

     E  L  L  V  L  L  E  N  E  R  T  L  D  Y  H  D  S  N  V  K
1321 gaactgttggttctattggaaaatgaaagaactttggactatcacgattcaaatgtgaag  1380

     N  L  Y  E  K  V  R  S  Q  L  K  N  N  A  K  E  I  G  N  G
1381 aacttgtatgaaaaagtaagaagccagttaaaaaacaatgccaaggaaattggaaacggc  1440

     C  F  E  F  Y  H  K  C  D  N  T  C  M  E  S  V  K  N  G  T
1441 tgctttgaattttaccacaaatgcgataacacgtgcatggaaagtgtcaaaaatgggact  1500

     Y  D  Y  P  K  Y  S  E  E  A  K  L  N  R  E  K  I  D  G  V
1501 tatgactacccaaaatactcagaggaagcaaaattaaacagagaaaaaatagatggggta  1560

     K  L  E  S  T  R  I  Y  Q  I  L  A  I  Y  S  T  V  A  S  S
1561 aagctggaatcaacaaggatttaccagattttggcgatctattcaactgtcgccagttca  1620

     L  V  L  V  V  S  L  G  A  I  S  F  W  M  C  S  N  G  S  L
1621 ttggtactggtagtctccctgggggcaatcagcttctggatgtgctctaatgggtctcta  1680

     Q  C  R  I  C  I  *
1681 cagtgtagaatatgtatttaa
```

FIG. 2 cont.

```
      M  A  D  G  W  Y  G  Y  H  H  Q  N  E  Q  G  S  G  Y  A  A
1081  atggcagatggatggtacggttatcaccatcaaaatgagcaggggtcaggatatgcagcc  1140
      D  A  K  S  T  Q  N  A  I  D  A  I  T  N  K  V  N  S  V  I
1141  gacgcaaagagcacacaaaatgccattgacgcaattactaacaaagtaaattctgttatt  1200
      E  K  M  N  T  Q  F  T  A  V  G  K  E  F  A  H  L  E  A  R
1201  gaaaagatgaatacacagttcacagcagtgggtaaagagttcgcccacctggaagcaaga  1260
      I  E  N  L  N  K  K  V  D  D  G  F  L  D  I  W  T  Y  N  A
1261  atagagaatctaaataaaaaggttgatgatggtttcctggacatttggacttacaatgcc  1320
      E  L  L  V  L  L  E  N  E  R  T  L  D  Y  H  D  S  N  V  K
1321  gaactgttggttctattggaaaatgaaagaactttggactatcacgattcaaatgtgaag  1380
      N  L  Y  E  K  V  R  A  Q  L  K  N  N  A  K  E  I  G  N  G
1381  aacttgtatgaaaaagtaagagcccagttaaaaaacaatgccaaggaaattggaaacggc  1440
      C  F  E  F  Y  H  K  C  D  A  A  C  M  E  S  V  K  N  G  T
1441  tgctttgaattttaccacaaatgcgatgccgcctgcatggaaagtgtcaaaaatgggact  1500
      Y  D  Y  P  K  Y  S  E  E  A  K  L  N  R  E  A  I  D  G  V
1501  tatgactacccaaaatactcagaggaagcaaaattaaacagagaagcaatagatggggta  1560
      K  L  E  S  T  R  I  Y  Q  I  L  A  I  Y  S  T  V  A  S  S
1561  aagctggaatcaacaaggatttaccagattttggcgatctattcaactgtcgccagttca  1620
      L  V  L  A  V  S  L  G  A  I  S  F  W  M  C  S  N  G  S  L
1621  ttggtacttgcagtctccctgggggcaatcagcttctggatgtgctctaatgggtctcta  1680
      Q  C  R  I  C  I  *
1681  cagtgtagaatatgtatttaa
```

A can be replaced with any non-hypervariable amino acid

FIG. 3 cont.

IDENTIFICATION OF VARIABLE INFLUENZA RESIDUES AND USES THEREOF

CROSS-REFERENCE TO RELATED APPLICATIONS

This application claims the benefit of U.S. Provisional Patent Application Ser. No. 62/983,519, filed Feb. 28, 2020, the entire contents of which is incorporated herein by reference.

GOVERNMENT SUPPORT

This invention was made with Government support under Grant No. FA8702-15-D-0001 awarded by the U.S. Air Force. The Government has certain rights in the invention.

SEQUENCE LISTING STATEMENT

A computer readable form of the Sequence Listing is filed with this application by electronic submission and is incorporated into this application by reference in its entirety. The Sequence Listing is contained in the file created on Aug. 18, 2022 having the file name "21-0895-US_SeqList2.txt" and is 170 in size.

BACKGROUND

Influenza viruses are members of the family Orthomyxoviridae and are divided into three genera: A, B, and C. Influenza A and B viruses cause respiratory infections in humans. Current vaccines are designed to induce immunity to hemagglutinin, one of two glycoproteins present on the surface of influenza viruses. Despite the availability of highly effective vaccines, influenza infection still results in up to 5,000,000 hospitalizations and 500,000 deaths annually worldwide. Currently available vaccines against influenza include up to four influenza hemagglutinin components intended to provide protection against H1N1, H3N2, and influenza B strains. Vaccine compositions are reassessed annually by the World Health Organization (WHO) to accommodate antigenic shift and drift in circulating virus strains. Such a strategy requires diligent surveillance of circulating influenza strains from year to year, and vaccine mismatches resulting from inaccurate predictions or unpredictable HA mutations arising during vaccine manufacture, which can result in increased morbidity and mortality even in vaccinated populations.

Given the shortcomings of the currently available vaccines, there remains a need for prophylactic and therapeutic compositions and methods that can be used to broadly target influenza in view of the high virus mutation rate amongst strains.

SUMMARY OF THE INVENTION

The present disclosure provides immunogenic compositions, methods for immunizing a subject against infection with an influenza virus, methods for inducing an immune response against influenza virus, and methods of reducing an influenza virus infection in a subject in need thereof by administering one or more immunogenic compositions of the disclosure.

In one aspect, the disclosure provides an immunogenic composition comprising at least one polypeptide comprising an amino acid sequence of an influenza viral protein having one or more hypervariable amino acid residues and one or more conserved amino acid residues, wherein the amino acid sequence of the polypeptide comprises a substitution of at least one hypervariable amino acid residue with a different, non-hypervariable amino acid residue. In one embodiment, the at least one non-hypervariable amino acid residue is a nonpolar, aliphatic R group amino acid selected from alanine, glycine, valine, leucine, isoleucine, and methionine. In one embodiment, the non-hypervariable amino acid residue is alanine or glycine.

In one aspect, the disclosure provides an immunogenic composition comprising at least one polypeptide comprising an amino acid sequence of an influenza viral protein having one or more hypervariable amino acid residues and one or more conserved amino acid residues, wherein the amino acid sequence of the polypeptide comprises a substitution of at least one hypervariable amino acid residue with an amino acid residue that is a hypervariable-substitute. In one embodiment, the hypervariable-substitute is a nonpolar, aliphatic R group amino acid selected from alanine, glycine, valine, leucine, isoleucine, and methionine. In one embodiment, the hypervariable-substitute is alanine or glycine.

In one aspect, the disclosure provides an immunogenic composition comprising two or more polypeptides each individually comprising an amino acid sequence of a viral protein comprising one or more hypervariable amino acid residues, wherein each polypeptide individually comprises an amino acid sequence having a substitution of at least one hypervariable amino acid residue with a different, non-hypervariable amino acid residue, and wherein the polypeptides are of the same or different influenza virus strains. In one embodiment, the at least one non-hypervariable amino acid residue is a nonpolar, aliphatic R group amino acid selected from alanine, glycine, valine, leucine, isoleucine, and methionine. In one embodiment, the non-hypervariable amino acid residue is alanine or glycine.

In one aspect, the disclosure provides an immunogenic composition comprising two or more polypeptides each individually comprising an amino acid sequence of a viral protein comprising one or more hypervariable amino acid residues, wherein each polypeptide individually comprises an amino acid sequence having a substitution of at least one hypervariable amino acid residue with an amino acid residue that is a hypervariable-substitute, and wherein the polypeptides are of the same or different influenza virus strains. In one embodiment, the hypervariable-substitute is a nonpolar, aliphatic R group amino acid selected from alanine, glycine, valine, leucine, isoleucine, and methionine. In one embodiment, the hypervariable-substitute is alanine or glycine.

In one aspect, the disclosure provides an immunogenic composition comprising at least one polypeptide comprising an amino acid sequence of an influenza viral protein having one or more hypervariable amino acid residues and one or more conserved amino acid residues, wherein the influenza virus is an influenza A virus strain or an influenza B virus strain, wherein the amino acid sequence of the polypeptide comprises a substitution of at least one hypervariable amino acid residue with a different, non-hypervariable amino acid residue. In one embodiment, the at least one non-hypervariable amino acid residue is a nonpolar, aliphatic R group amino acid selected from alanine, glycine, valine, leucine, isoleucine, and methionine. In one embodiment, the non-hypervariable amino acid residue is alanine or glycine.

In one aspect, the disclosure provides an immunogenic composition comprising at least one polypeptide comprising an amino acid sequence of an influenza viral protein having one or more hypervariable amino acid residues and one or more conserved amino acid residues, wherein the influenza virus is an influenza A virus strain or an influenza B virus strain, wherein the amino acid sequence of the polypeptide comprises a substitution of at least one hypervariable amino acid residue with an amino acid residue that is a hypervariable-substitute. In one embodiment, the hypervariable substitute is a nonpolar, aliphatic R group amino acid selected from alanine, glycine, valine, leucine, isoleucine, and methionine. In one embodiment, the hypervariable-substitute is alanine or glycine.

In one aspect, the disclosure provides an immunogenic composition comprising at least one polypeptide comprising an amino acid sequence of an influenza viral protein having one or more hypervariable amino acid residues and one or more conserved amino acid residues, wherein the virus influenza virus is H1N1, H3N2, B/Victoria/2/1987-like, B/Yamagata/16/1988-like, H5N1, or any combination thereof, wherein the amino acid sequence of the polypeptide comprises a substitution of at least one hypervariable amino acid residue with a different, non-hypervariable amino acid residue. In one embodiment, the at least one non-hypervariable amino acid residue is a nonpolar, aliphatic R group amino acid selected from alanine, glycine, valine, leucine, isoleucine, and methionine. In one embodiment, the non-hypervariable amino acid residue is alanine or glycine.

In one aspect, the disclosure provides an immunogenic composition comprising at least one polypeptide comprising an amino acid sequence of an influenza viral protein having one or more hypervariable amino acid residues and one or more conserved amino acid residues, wherein the virus influenza virus is H1N1, H3N2, B/Victoria/2/1987-like, B/Yamagata/16/1988-like, H5N1, or any combination thereof, wherein the amino acid sequence of the polypeptide comprises a substitution of at least one hypervariable amino acid residue with an amino acid residue that is a hypervariable-substitute. In one embodiment, the hypervariable substitute is a nonpolar, aliphatic R group amino acid selected from alanine, glycine, valine, leucine, isoleucine, and methionine. In one embodiment, the hypervariable-substitute is alanine or glycine.

In one aspect, the disclosure provides an immunogenic composition comprising at least one polypeptide comprising an amino acid sequence of an influenza viral protein having one or more hypervariable amino acid residues and one or more conserved amino acid residues, wherein the at least one viral protein is a hemagglutinin protein, a neuraminidase protein, a M2 matrix protein, or combinations thereof, wherein the amino acid sequence of the polypeptide comprises a substitution of at least one hypervariable amino acid residue with a different, non-hypervariable amino acid residue. In one embodiment, the at least one non-hypervariable amino acid residue is a nonpolar, aliphatic R group amino acid selected from alanine, glycine, valine, leucine, isoleucine, and methionine. In one embodiment, the non-hypervariable amino acid residue is alanine or glycine.

In one aspect, the disclosure provides an immunogenic composition comprising at least one polypeptide comprising an amino acid sequence of an influenza viral protein having one or more hypervariable amino acid residues and one or more conserved amino acid residues, wherein the at least one viral protein is a hemagglutinin protein, a neuraminidase protein, a M2 matrix protein, or combinations thereof, wherein the amino acid sequence of the polypeptide comprises a substitution of at least one hypervariable amino acid residue with an amino acid that is a hypervariable-substitute. In one embodiment, the hypervariable substitute is a nonpolar, aliphatic R group amino acid selected from alanine, glycine, valine, leucine, isoleucine, and methionine. In one embodiment, the hypervariable-substitute is alanine or glycine.

In one aspect, the disclosure provides an immunogenic composition comprising at least one polypeptide comprising an amino acid sequence of an influenza viral protein having one or more hypervariable amino acid residues and one or more conserved amino acid residues, wherein the amino acid sequence of the polypeptide comprises a substitution of at least one hypervariable amino acid residue with a different, non-hypervariable amino acid residue, and wherein the polypeptide comprises at least one B cell epitope. In one embodiment, the at least one non-hypervariable amino acid residue is a nonpolar, aliphatic R group amino acid selected from alanine, glycine, valine, leucine, isoleucine, and methionine. In one embodiment, the non-hypervariable amino acid residue is alanine or glycine. In one embodiment, the immunogenic composition elicits an immune response against the at least one B cell epitope. In one embodiment, the immune response comprises production of antibodies that bind the at least one B cell epitope.

In one aspect, the disclosure provides an immunogenic composition comprising at least one polypeptide comprising an amino acid sequence of an influenza viral protein having one or more hypervariable amino acid residues and one or more conserved amino acid residues, wherein the amino acid sequence of the polypeptide comprises a substitution of at least one hypervariable amino acid residue with an amino acid that is a hypervariable-substitute, and wherein the polypeptide comprises at least one B cell epitope. In one embodiment, the hypervariable substitute is a nonpolar, aliphatic R group amino acid selected from alanine, glycine, valine, leucine, isoleucine, and methionine. In one embodiment, the hypervariable-substitute is alanine or glycine. In one embodiment, the immunogenic composition elicits an immune response against the at least one B cell epitope. In one embodiment, the immune response comprises production of antibodies that bind the at least one B cell epitope.

In one aspect, the disclosure provides an immunogenic composition comprising at least one polypeptide comprising an amino acid sequence of an influenza viral protein having one or more hypervariable amino acid residues and one or more conserved amino acid residues, wherein the viral protein comprises an amino acid sequence selected from SEQ ID NOs: 1-6, and wherein the amino acid sequence of the polypeptide comprises a substitution of at least one hypervariable amino acid residue with a different, non-hypervariable amino acid residue. In one embodiment, the polypeptide comprises at least one B cell epitope. In one embodiment, the at least one non-hypervariable amino acid residue is a nonpolar, aliphatic R group amino acid selected from alanine, glycine, valine, leucine, isoleucine, and methionine. In one embodiment, the non-hypervariable amino acid residue is alanine or glycine. In one embodiment, the immunogenic composition elicits an immune response against the at least one B cell epitope. In one embodiment, the immune response comprises production of antibodies that bind the at least one B cell epitope. In one embodiment, the hypervariable amino acid which is substituted is selected from one or more underlined amino acid residues set forth in SEQ ID NOs: 1-6.

In one aspect, the disclosure provides an immunogenic composition comprising at least one polypeptide comprising an amino acid sequence of an influenza viral protein having one or more hypervariable amino acid residues and one or more conserved amino acid residues, wherein the viral protein comprises an amino acid sequence selected from SEQ ID NOs: 1-6, and wherein the amino acid sequence of the polypeptide comprises a substitution of at least one hypervariable amino acid residue with an amino acid that is a hypervariable-substitute. In one embodiment, the polypeptide comprises at least one B cell epitope. In one embodiment, the at least one non-hypervariable amino acid residue is a nonpolar, aliphatic R group amino acid selected from alanine, glycine, valine, leucine, isoleucine, and methionine. In one embodiment, the non-hypervariable amino acid residue is alanine or glycine. In one embodiment, the immunogenic composition elicits an immune response against the at least one B cell epitope. In one embodiment, the immune response comprises production of antibodies that bind the at least one B cell epitope. In one embodiment, the hypervariable amino acid which is substituted is selected from one or more underlined amino acid residues set forth in SEQ ID NOs: 1-6.

In any of the foregoing or related embodiments, the immunogenic composition further comprises an adjuvant.

In any of the foregoing and related aspects, the immunogenic composition comprises a nucleic acid encoding the at least one polypeptide.

In one aspect, the disclosure provides a method for immunizing a subject against infection with an influenza virus, comprising administering one or more immunogenic compositions of the disclosure.

In one aspect, the disclosure provides a method for inducing an immune response against influenza virus, comprising administering to a subject one or more immunogenic compositions of the disclosure.

In one aspect, the disclosure provides a method of reducing an influenza virus infection in a subject in need thereof, comprising administering to a subject one or more immunogenic compositions of the disclosure.

In any of the foregoing and related aspects, the administration of one or more immunogenic compositions to the subject results in the production of antibodies against the at least one B cell epitope in the polypeptide.

Other aspects of the disclosure relate to methods for generating an immunogenic composition comprising:

(i) obtaining two or more amino acid sequences of viral proteins from one or more strains of a particular type and/or subtype of influenza virus;

(ii) aligning the amino acid sequences to generate an alignment;

(iii) identifying one or more hypervariable amino acid residues between strains and one or more conserved amino acid residues; and (iv) substituting at least one hypervariable amino acid residue identified in (iii) with a different, non-hypervariable amino acid residue. In some aspects, the alignment is generated with Dawn, or Clustal-Omega. In some aspects, the method further comprises performing site-specific mutagenesis at each hypervariable amino residue, or combinations thereof, and determining if the mutated viral protein elicits neutralizing antibodies against the multiple strains of influenza virus.

Other aspects of the disclosure relate to immunogenic compositions comprising at least one polypeptide comprising an amino acid sequence of an influenza viral protein having one or more amino acid residues which are conserved between one or more strains of a type and/or subtype of influenza virus, wherein the amino acid sequence of the polypeptide comprises an amino acid sequence comprising the one or more conserved amino acid residues.

In one aspect, the disclosure provides an immunogenic composition comprising two or more polypeptides, each individually comprising an amino acid sequence of a viral protein having one or more amino acid residues which are conserved between one or more strains of a type and/or subtype of influenza virus, wherein each polypeptide individually comprises an amino acid sequence comprising one or more conserved amino acid sequences, and wherein the polypeptides are of the same or different influenza virus strains. In some aspects, the two or more polypeptides are of the same viral protein. In some aspects the two or more polypeptides are of different viral proteins.

In one aspect the disclosure relates to immunogenic compositions comprising at least one polypeptide comprising an amino acid sequence of an influenza viral protein having one or more amino acid residues which are conserved between one or more strains of a type and/or subtype of influenza virus, wherein the amino acid sequence of the polypeptide comprises an amino acid sequence comprising the one or more conserved amino acid residues, and wherein the polypeptide comprises two or more T cell epitopes, wherein each T cell epitope is operably linked to one other, optionally via a linker.

In one aspect, the disclosure provides immunogenic compositions comprising at least one polypeptide comprising an amino acid sequence of an influenza viral protein having one or more amino acid residues which are conserved between one or more strains of a type and/or subtype of influenza virus, wherein the influenza virus is an influenza A virus strain or an influenza B virus strain, and wherein the amino acid sequence of the polypeptide comprises an amino acid sequence comprising the one or more conserved amino acid residues.

In one aspect, the disclosure provides immunogenic compositions comprising at least one polypeptide comprising an amino acid sequence of an influenza viral protein having one or more amino acid residues which are conserved between one or more strains of a type and/or subtype of influenza virus, wherein the influenza virus is H1N1, H3N2, B/Victoria/2/1987-like, B/Yamagata/16/1988-like, H5N1, or any combination thereof, and wherein the amino acid sequence of the polypeptide comprises an amino acid sequence comprising the one or more conserved amino acid residues.

In one aspect, the disclosure provides immunogenic compositions comprising at least one polypeptide comprising an amino acid sequence of an influenza viral protein having one or more amino acid residues which are conserved between one or more strains of a type and/or subtype of influenza virus, wherein the viral protein is a hemagglutinin protein, a neuraminidase protein, a M2 matrix protein, or combinations thereof, and wherein the amino acid sequence of the polypeptide comprises an amino acid sequence comprising the one or more conserved amino acid residues.

In one aspect, the disclosure provides immunogenic compositions comprising at least one polypeptide comprising an amino acid sequence of an influenza viral protein having one or more amino acid residues which are conserved between one or more strains of a type and/or subtype of influenza virus, wherein the at least one viral polypeptide comprises at least one conserved amino acid sequence selected from SEQ ID NOs: 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 151, 153 and 155, and any combination thereof, and wherein the amino acid sequence of the polypeptide comprises an amino acid sequence comprising the one or more conserved amino acid residues.

In any of the foregoing and related aspects, the immunogenic composition comprises a nucleic acid encoding the at least one polypeptide.

In any of the foregoing and related aspects, the immunogenic composition elicits an immune response against the virus. In some aspects, the immune response is a T cell response directed to the one of more T cell epitopes comprising the conserved amino acid residues of the viral protein.

In any of the foregoing and related aspects, the immunogenic composition further comprises an adjuvant.

In some aspects the disclosure provides methods of immunizing a subject against infection with an influenza virus, optionally a T cell or B cell response or both, comprising administering one or more immunogenic compositions of the disclosure.

In some aspects the disclosure provides methods for inducing an immune response against influenza virus, optionally a T cell or B cell response or both, comprising administering one or more immunogenic compositions of the disclosure.

In some aspects the disclosure provides methods of reducing an influenza virus infection in a subject in need thereof, optionally a T cell or B cell response or both, comprising administering one or more immunogenic compositions of the disclosure.

In some aspects, the composition elicits a T cell response against one or more T cell epitopes comprising the conserved amino acid residues of the viral protein.

In other aspects, the disclosure provides methods for generating an immunogenic composition comprising:

(i) obtaining two or more amino acid sequences of viral proteins from multiple strains of a particular type and/or subtype of influenza virus;

(ii) aligning the amino acid sequences to generate an alignment;

(iii) identifying a region of amino acid residues having conserved amino acid residues between strains; and (iv) generating a polypeptide comprising the region of amino acids identified in (iii). In one embodiment, the alignment is generated with Dawn or Clustal-Omega.

In one embodiment, the methods of the disclosure further comprise determining if the immunogenic composition elicits a T cell response against the multiple strains of influenza virus.

In some aspects, the disclosure provides an immunogenic composition comprising:

(a) one or more immunogenic compositions comprising at least one polypeptide comprising an amino acid sequence of an influenza viral protein having one or more hypervariable amino acid residues and one or more conserved amino acid residues, optionally wherein the influenza virus is an influenza A virus strain or an influenza B virus strain, and wherein the amino acid sequence of the polypeptide comprises a substitution of at least one hypervariable amino acid residue with a different, non-hypervariable amino acid residue; and (b) one or more immunogenic compositions comprising at least one polypeptide comprising an amino acid sequence of an influenza viral protein having one or more amino acid residues which are conserved between one or more strains of a type and/or subtype of influenza virus, optionally wherein the influenza virus is an influenza A virus strain or an influenza B virus strain, and wherein the amino acid sequence of the polypeptide comprises an amino acid sequence comprising the one or more conserved amino acid residues. In one embodiment, the at least one non-hypervariable amino acid residue in an immunogenic composition (a) is a nonpolar, aliphatic R group amino acid selected from alanine, glycine, valine, leucine, isoleucine, and methionine. In one embodiment, the non-hypervariable amino acid residue is alanine or glycine.

In one embodiment, the at least one polypeptide of (a) and the at least one polypeptide of (b) are from the same or different viral proteins from the same influenza virus type. In one embodiment, the at least one polypeptide of (a) and the at least on polypeptide of (b) are from the same or different proteins from different influenza virus types. In one embodiment, the at least one polypeptide of (b) comprises two or more polypeptides each individually comprising a T cell epitope. In one embodiment, the two or more polypeptides comprise same amino acid sequence. In one embodiment, the two or more polypeptides comprise different amino acid sequences. In one embodiment, the two or more polypeptides are derived from the same viral protein. In one embodiment the two or more polypeptides are derived from different viral proteins. In one embodiment, the influenza virus is H1N1, H3N2, B/Victoria/2/1987-like, B/Yamagata/16/1988-like, H5N1, or any combination thereof. In one embodiment, the two or more polypeptides are operably linked to each other, optionally comprising a linker and/or spacer between each polypeptide. In one embodiment, the one or more compositions of (a) and the one ore more compositions of (b) further comprise an adjuvant.

In some aspects, the disclosure provides an immunogenic composition comprising:

(a) one or more immunogenic compositions comprising at least one polypeptide comprising an amino acid sequence of an influenza viral protein having one or more hypervariable amino acid residues and one or more conserved amino acid residues, the viral protein is a hemagglutinin protein, a neuraminidase protein, a M2 matrix protein, or combinations thereof, and wherein the amino acid sequence of the polypeptide comprises a substitution of at least one hypervariable amino acid residue with a different, non-hypervariable amino acid residue; and (b) one or more immunogenic compositions comprising at least one polypeptide comprising an amino acid sequence of an influenza viral protein having one or more amino acid residues which are conserved between one or more strains of a type and/or subtype of influenza virus, the viral protein is a hemagglutinin protein, a neuraminidase protein, a M2 matrix protein, or combinations thereof, and wherein the amino acid sequence of the polypeptide comprises an amino acid sequence comprising the one or more conserved amino acid residues. In one embodiment, the at least one non-hypervariable amino acid residue in an immunogenic composition (a) is a nonpolar, aliphatic R group amino acid selected from alanine, glycine, valine, leucine, isoleucine, and methionine. In one embodiment, the non-hypervariable amino acid residue is alanine or glycine. In one embodiment, the immunogenic composition elicits an immune response against at least one T cell epitope, at least one B cell epitope, or combinations thereof. In one embodiment, the immune response comprises production of antibodies that bind B cell epitopes, eliciting a T cell response against T cell epitopes, or both.

In some aspects, the disclosure provides an immunogenic composition comprising:

(a) one or more immunogenic compositions comprising at least one polypeptide comprising an amino acid sequence of an influenza viral protein having one or more hypervariable amino acid residues and one or more conserved amino acid residues, wherein the at least one polypeptide comprises an amino acid sequence selected from SEQ ID NOs: 1-6, or combinations thereof, and wherein the amino acid sequence of the polypeptide comprises a substitution of at least one hypervariable amino acid residue with a different, non-hypervariable amino acid residue; and (b) one or more immunogenic compositions comprising at least one polypeptide comprising an amino acid sequence of an influenza viral protein having one or more amino acid residues which are conserved between one or more strains of a type and/or subtype of influenza virus, and wherein the amino acid sequence of the polypeptide comprises an amino acid sequence comprising the one or more conserved amino acid residues. In one embodiment, the at least one non-hypervariable amino acid residue in an immunogenic composition (a) is a nonpolar, aliphatic R group amino acid selected from alanine, glycine, valine, leucine, isoleucine, and methionine. In one embodiment, the non-hypervariable amino acid residue is alanine or glycine. In one embodiment, the immunogenic composition elicits an immune response against at least one T cell epitope, at least one B cell epitope, or combinations thereof. In one embodiment, the immune response comprises production of antibodies that bind B cell epitopes, eliciting a T cell response against T cell epitopes, or both.

In some aspects, the disclosure provides an immunogenic composition comprising:

(a) one or more immunogenic compositions comprising at least one polypeptide comprising an amino acid sequence of an influenza viral protein having one or more hypervariable amino acid residues and one or more conserved amino acid residues, wherein the amino acid sequence of the polypeptide comprises a substitution of at least one hypervariable amino acid residue with a different, non-hypervariable amino acid residue, and wherein the hypervariable amino acid which is substituted is selected from one or more underlined amino acid residues set forth in SEQ ID NOs: 1-6; and (b) one or more immunogenic compositions comprising at least one polypeptide comprising an amino acid sequence of an influenza viral protein having one or more amino acid residues which are conserved between one or more strains of a type and/or subtype of influenza virus, and wherein the amino acid sequence of the polypeptide comprises an amino acid sequence comprising the one or more conserved amino acid residues. In one embodiment, the at least one non-hypervariable amino acid residue in an immunogenic composition (a) is a nonpolar, aliphatic R group amino acid selected from alanine, glycine, valine, leucine, isoleucine, and methionine. In one embodiment, the non-hypervariable amino acid residue is alanine or glycine. In one embodiment, the immunogenic composition elicits an immune response against at least one T cell epitope, at least one B cell epitope, or combinations thereof. In one embodiment, the immune response comprises production of antibodies that bind B cell epitopes, eliciting a T cell response against T cell epitopes, or both.

In one embodiment, the at least one polypeptide of (b) comprises at least one conserved amino acid sequence selected from SEQ ID NOs: 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 151, 153, and 155, or any combination thereof.

In any of the foregoing or related aspects, the immunogenic composition comprises a nucleic acid encoding the at least one polypeptide of (b).

Other aspects of the disclosure relate to methods for immunizing a subject against infection with an influenza virus, comprising administering one or more immunogenic composition of (a) and one or more immunogenic compositions of (b).

Other aspects of the disclosure relate to methods for inducing an immune response in a subject to protect against infection with an influenza virus, or reducing an influenza virus infection comprising administering one or more immunogenic composition of (a) and one or more immunogenic compositions of (b).

In one embodiment, the immunogenic composition of (a) is administered prior to, simultaneously with, or subsequently to administration of the immunogenic composition (b).

Other aspects of the disclosure relate to methods for inducing an immune response or reducing an influenza virus infection in a subject in need thereof who has received or is receiving one or more compositions of (a), the method comprising: administering to the subject an effective amount of one or more compositions of (b).

Other aspects of the disclosure relate to methods for inducing an immune response in a subject in need thereof who has received or is receiving one or more compositions of (b), the method comprising: administering to the subject an effective amount of one or more compositions of (a).

Other aspects of the disclosure relate to methods for reducing an influenza virus infection in a subject, comprising administering to the subject an immunogenic composition comprising: one or more compositions of any of (a); and one or more compositions of (b). In one embodiment, the immunogenic composition of (a) is administered prior to, simultaneously with, or subsequently to administration of the immunogenic composition (b).

In other aspects, the disclosure provides nucleic acid molecules comprising a nucleotide sequence having substantial complementarity to a nucleotide sequence encoding a polypeptide derived from a viral protein of influenza, wherein the at least one polypeptide comprises conserved amino acid sequence between multiple strains of a particular type and/or subtype of influenza virus. In some embodiments, the nucleic acid molecule is an RNA interference (RNAi) molecule. In some embodiments, the RNAi molecule is an siRNA or miRNA molecule. In some embodiments, the nucleic acid molecule is an antisense oligonucleotide. In some embodiments, the nucleic acid encodes for one or more polypeptides. In some embodiment, the one or more polypeptides comprise the same amino acid sequence. In some embodiments, the one or more polypeptides comprise different amino acid sequences. In some embodiments, wherein the one or more polypeptides are derived from the same viral protein. In some embodiments, wherein the one or more polypeptides are derived from different viral proteins. In some embodiments, the one or more polypeptides are operably linked to each other, optionally comprising a linker and/or spacer between each polypeptide. In some embodiments, the nucleic acid is formulated in a composition comprising an adjuvant. In some embodiments, the influenza virus is an influenza A virus strain or an influenza B virus strain. In some embodiments, the influenza virus is H1N1, H3N2, B/Victoria/2/1987-like, B/Yamagata/16/1988-like, H5N1, or any combination thereof. In some embodiments, the viral protein is a hemagglutinin protein, a neuraminidase protein, a M2 matrix protein, or combinations thereof. In some embodiments, the composition elicits an immune response against the virus. In some embodiments, the immune response is a T cell response directed to one of more T cell epitopes. In some embodiments, the nucleic acid encodes a conserved amino acid sequence selected from SEQ ID NOs: 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 151, 153 and 155, or any combination thereof.

In some embodiments, the disclosure provides method for immunizing a subject against infection with an influenza virus, methods for inducing an immune response against influenza virus, and methods of reducing an influenza virus infection in a subject in need thereof, comprising administering the nucleic acid molecule of the disclosure. In some embodiments, the nucleic acid molecule elicits a T cell response directed to one of more T cell epitopes. In some embodiments, the method further comprises determining if the nucleic acid molecule elicits a T cell response against the multiple strains of influenza virus.

In other aspects, the disclosure provides methods of treating an influenza infection, comprising administering the nucleic acid molecule of the disclosure, optionally in a delivery vehicle.

BRIEF DESCRIPTION OF FIGURES

FIG. 2 provides the amino acid sequence (SEQ ID NO: 1) and nucleic acid sequence (SEQ ID NO: 169) of influenza A hemagglutinin. Hypervariable residues are indicated by a box whereas highly conserved regions are underlined.

DETAILED DESCRIPTION

Figure 1:
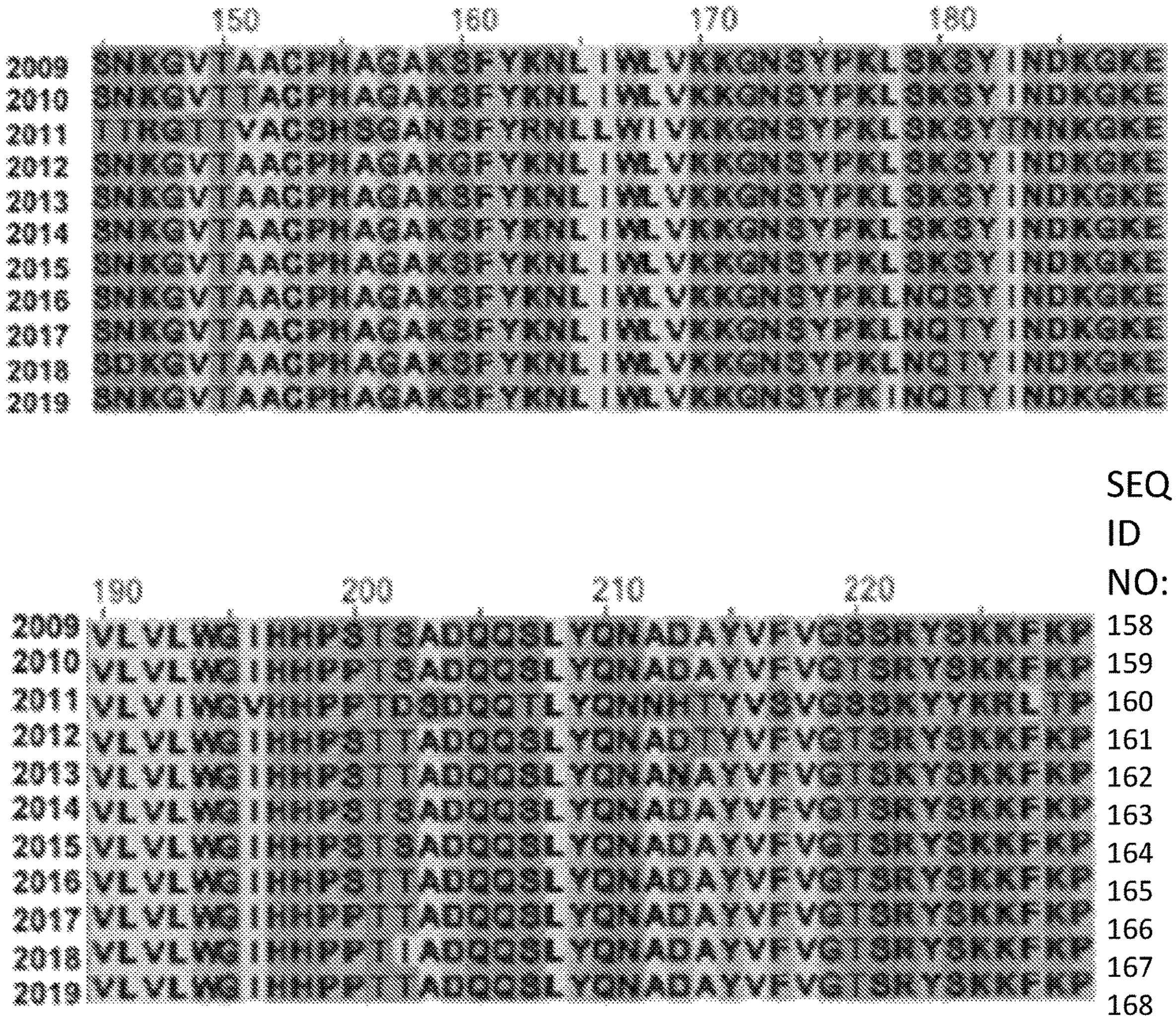
FIG. 1 is a schematic showing yearly variations in hemagglutinin amino acid sequence from influenza A H1N1.

The present disclosure provides compositions and methods for inducing an immune response across strains of influenza virus. Specifically, hypervariable residues and highly conserved regions of amino acid sequences have been identified in various influenza viral proteins that can be exploited to induce a universal immune response amongst strains.

Identification of Influenza Residues

Influenza is caused by a virus that attacks mainly the upper respiratory tract—the nose, throat and bronchi and rarely also the lungs. The infection usually lasts for about a week. It is characterized by sudden onset of high fever, myalgia, headache and severe malaise, non-productive cough, sore throat, and rhinitis. Most people recover within one to two weeks without requiring any medical treatment. However, in the very young, the elderly and people suffering from medical conditions such as lung diseases, diabetes, cancer, kidney or heart problems, influenza poses a serious risk. In these people, the infection may lead to severe complications of underlying diseases, pneumonia and death. Annual influenza epidemics are thought to result in between three and five million cases of severe illness and between 250,000 and 500,000 deaths every year around the world.

Influenza virus is a member of Orthomyxoviridae family. There are three subtypes of influenza viruses, designated influenza A, influenza B, and influenza C. The influenza virion contains a segmented negative-sense RNA genome, which encodes the following proteins: hemagglutinin (HA), neuraminidase (NA), matrix (MI), proton ion-channel protein (M2), nucleoprotein (NP), polymerase basic protein 1 (PBI), polymerase basic protein 2 (PB2), polymerase acidic protein (PA), and nonstructural protein 2 (NS2). The HA, NA, MI, and M2 are membrane associated, whereas NP, PBI, PB2, PA, and NS2 are nucleocapsid associated proteins. The MI protein is the most abundant protein in influenza particles. The HA and NA proteins are envelope glycoproteins, responsible for virus attachment and penetration of the viral particles into the cell. Specifically, HA binds the influenza virus to cells with sialic acid-containing on surface structures on their membranes.

Both HA and NA proteins are the sources of the major immunodominant epitopes for virus neutralization and protective immunity, making them important components for prophylactic influenza vaccines. The genetic makeup of influenza viruses allows frequent minor genetic changes, known as antigenic drift. Thus, the amino acid sequence of the major antigens of influenza, particularly HA, is highly variable across groups, subtypes and strains. For this reason, current seasonal influenza vaccines need to be revised every 1-3 years to account for mutations in HA and NA proteins (antigenic drift). A further limitation of the current vaccine approach is that the influenza strains used in the vaccine are selected by the WHO/CDC based on the agencies' best guess as to the prevalent influenza strains for the upcoming flu season. Often times, the guess is not accurate, and the vaccine strains do not match the seasonal influenza strains, limiting the effectiveness of the seasonal vaccines. Seasonal vaccines are also not designed to provide protection against pandemic strains that can result from antigen shift. Further, as the name suggests, seasonal vaccines must be administered every year.

Pandemic outbreaks of influenza are caused by the emergence of a pathogenic and transmissible virus to which the human population is immunologically naive. Because the virus is new, the human population has little to no immunity against it. The virus spreads quickly from person-to-person worldwide. Three times in the last century, the influenza A viruses have undergone major genetic changes mainly in their H-component, resulting in global pandemics and large tolls in terms of both disease and deaths. The most infamous pandemic was "Spanish Flu" which affected large parts of the world population and is thought to have killed at least 40 million people in 1918-1919. More recently, two other influenza A pandemics occurred in 1957 ("Asian influenza") and 1968 ("Hong Kong influenza") and caused significant morbidity and mortality globally. In contrast to current influenza epidemics, these pandemics were associated with severe outcomes also among healthy younger persons, albeit not on such a dramatic scale as the "Spanish flu" where the death rate was highest among healthy young adults. More recently, limited outbreaks of a new influenza subtype A (H1N1) directly transmitted from swine to humans have occurred in Mexico in 2009 and are being detected in an increasing number of countries. Currently, the mortality rate associated with swine-origin H1N1 influenza viruses appears to be similar to that of seasonal influenza strains. However, increased surveillance and detection of swine-origin H1N1 influenza could push the mortality rates higher. Due to antigenic drift, and even more dramatic alterations known as antigenic shift, pandemic influenza antigens (e.g., the HA amino acid sequence of the pandemic strain) are highly unpredictable. Thus, vaccines have traditionally been unavailable until the later stages of a pandemic.

There is an unmet need for influenza vaccines that can better address the current problems of antigenic drift, antigenic shift, and virus mismatch by providing broader protection against multiple influenza strains, including both seasonal and pandemic strains. There is also an unmet need for influenza vaccines that provide longer lasting immunity, particularly vaccines that would not have to be administered every year.

In some embodiments, the present disclosure provides immunogenic compositions that direct the immune response to highly conserved areas, surface exposed areas of the viral proteins, e.g., the HA and/or NA proteins. In some embodiments, the immunogenic compositions additionally comprise the M2 ectodomain of the virus. In yet another embodiment, the immunogenic compositions additionally comprise additional influenza proteins including internal virus proteins, e.g., the M1, NEP, NS1, NS2, PA, PB1, and PB2 proteins. Specifically, by mutating (e.g., substituting) hypervariable amino acid residues and/or generating polypeptides comprising highly conserved amino acid sequences, the compositions and methods described herein can be used to induce an immune response against different strains of influenza, including future strains that may develop due to antigenic shift.

In one embodiment, the present disclosure provides immunogenic compositions comprising one or more polypeptides derived from influenza proteins, wherein at least one hypervariable amino acid residue is replaced by a conserved, non-hypervariable amino acid residue. In one embodiment, the non-hypervariable amino acid residue is selected from amino acid residues with non-polar or neutral side charge. In one embodiment, the non-hypervariable amino acid residue is selected from alanine, glycine, valine, leucine, isoleucine and methionine.

In one embodiment, the present disclosure provides immunogenic compositions comprising one or more polypeptides derived from influenza proteins, wherein at least one hypervariable amino acid residue is replaced by an amino acid residue that is a conserved, hypervariable-substitute. In one embodiment, the hypervariable-substitute is selected from amino acid residues with non-polar or neutral side charge. In one embodiment, the hypervariable-substitute is selected from alanine, glycine, valine, leucine, isoleucine and methionine.

In some embodiments, the immunogenic composition comprises an influenza protein or polypeptide having a highly conserved regions as described herein. In some embodiments, the immunogenic composition comprises an influenza protein or polypeptide having a highly conserved regions annotated in any one of SEQ ID NOs: 171-193. In some embodiments, the protein or polypeptide comprises a non-hypervariable amino acid residue at an amino acid residue that is a hypervariable amino acid residue as annotated in any one of SEQ ID NOs: 171-193. In some embodiments, the protein or polypeptide comprises a hypervariable-substitute at an amino acid residue that is a hypervariable amino acid residue as annotated in any one of SEQ ID NOs: 171-193.

Influenza A

In some embodiments, the methods and compositions described herein target influenza A. Influenza A virus is both best characterized and the most serious threat to public health, capable of inducing massive epidemics or pandemics.

In some embodiments, the methods and compositions described herein comprise a recombinant viral protein derived from influenza A. In some embodiments, the viral protein of an influenza A virus is selected from subtypes H1, H2, H3, H4, H5, H6, H7, H8, H9, H10, H11, H12, H13, H14, H15, or H16. In some embodiments, the influenza virus is selected from the group consisting of H1N1, H3N2, H5N1, and H7N9. In some embodiments, the type A virus is a seasonal strain, such as, /Texas/36/1991, A/Singapore/1986, A/New Caledonia/20/1999, A/Solomon Islands/03/2006, A/Brisbane/59/2007, or A/Wisconsin/67/2005. In some embodiments, the type A virus is a pandemic strain such as A/California/07/2009, A/California/04/2009, A/Belgium/145/2009, A/South Carolina/01/1918, or A/New Jersey/1976.

Influenza B

In some embodiments, the methods and compositions described herein target influenza B. Influenza B viruses generally mutate slower than influenza A viruses.

In some embodiments, the methods and compositions described herein comprise a recombinant viral protein derived from influenza B. In some embodiments, the viral protein of an influenza B virus is selected from a Yamagata lineage strain or a Victoria lineage strain. In some embodiments, the viral protein of an influenza B virus is selected from B/Hong Kong/330/2001, B/Hong Kong/05/1972, B/Lee/40, B/Massachusetts/02/2012, B/Panama/45/1990, B/Singapore/222/79, B/Victoria/02/1987, B/Yamagata/16/1988, or B/Brisbane/60/2008.

Hemagglutinin (HA)

In some embodiments, an immunogenic composition described herein comprises a hemagglutinin (HA) recombinant protein, polypeptide or both. In some embodiments, the HA recombinant protein comprises a non-hypervariable amino acid substituted for a hypervariable amino acid residue. In some embodiments, the HA recombinant protein comprises a non-hypervariable amino acid replaced with an amino acid that is a hypervariable-substitute. In some embodiments, the HA polypeptide comprises a highly conserved region of amino acid sequences.

HA is a glycoprotein on the surface of influenza virus responsible for interaction of the virus with host cell receptors. HA proteins on the virus surface are trimers of hemagglutinin protein monomers that are enzymatically cleaved to yield amino-terminal HA1 and carboxy-terminal HA2 polypeptides. The globular head consists exclusively of the major portion of the HA1 polypeptide, whereas the stem that anchors the hemagglutinin protein into the viral lipid envelope is comprised of HA2 and part of HAL The globular head of a hemagglutinin protein includes two domains: the receptor binding domain (RBD), an ~148-amino acid residue domain that includes the sialic acid-binding site, and the vestigial esterase domain, a smaller ~75-amino acid residue region just below the RBD. The top part of the RBD adjacent to the 2,6-sialic acid recognition sites includes a large region (amino acids 131-143, 170-182, 205-215 and 257-262, 1918 numbering) (referred to herein as the RBD-A region) of over 6000 A2 per trimer that is 95% conserved between A/South Carolina/1/1918 (1918 SC) and A/California/04/2009 (2009 CA) pandemic strains. The globular head includes several antigenic sites that include immunodominant epitopes. Examples include the Sa, Sb, Ca1, Ca2 and Cb antigenic sites (see, for example, Caton A J et al, 1982, Cell 31, 417-427). The RBD-A region includes the Sa antigenic site and part of the Sb antigenic site.

H1N1

In some embodiments, the immunogenic composition comprises an HA recombinant protein or polypeptide derived from H1N1. In some embodiments, the recombinant H1N1 HA protein or polypeptide comprises a non-hypervariable amino acid residue at an amino acid position selected from Table 1, or any combination thereof. In some embodiments, the recombinant H1N1 HA protein or polypeptide comprises an amino acid that is a hypervariable-substitute at an amino acid position selected from Table 1, or any combination thereof.

TABLE 1

| List of Hypervariable Amino Acid Residues in H1N1 HA Protein |
|---|
| 13T |
| 14T |
| 52D |
| 53K |
| 78I |
| 86S |
| 88S |
| 101N |
| 114N |
| 137T |
| 145S |
| 147K |
| 155H |
| 158A |
| 159K |
| 160S |
| 163K |
| 178L |
| 179N |
| 180Q |
| 185D |
| 187G |
| 195G |
| 200S |
| 202T |
| 203A |
| 214A |
| 220T |
| 222R |
| 225K |
| 228K |
| 233T |
| 239D |
| 241E |
| 251V |
| 256K |
| 273T |
| 274M |
| 275E |
| 277N |
| 278A |
| 287T |
| 288P |
| 293N |
| 300E |
| 315I |
| 319K |
| 331L |
| 338V |
| 362V |
| 382L |
| 391K |
| 415N |
| 419K |
| 468N |
| 490N |
| 491T |
| 516K |
| 544V |

*residue numbering based on straight numbering of SEQ ID NO: 1. SEQ ID NO: 1 indicates these residues in bold.

In some embodiments, the recombinant H1N1 HA polypeptide comprises a highly conserved region of amino acid sequences. In some embodiments, the highly conserved region of amino acid sequences is selected from Table 2, or any combination thereof.

TABLE 2

| Highly Conserved Regions in H1N1 HA Protein | | | |
|---|---|---|---|
| GYHANNST (SEQ ID NO 7) | NVTVTHS (SEQ ID NO 9) | SWSYIVE (SEQ ID NO 11) | QSRGLFGAIAGF (SEQ ID NO 13) |
| QGSGYAAD (SEQ ID NO 15) | ITNKVNS (SEQ ID NO 17) | WTYNAELL (SEQ ID NO 19) | GCFEFYH (SEQ ID NO 21) |
| LGNPEC (SEQ ID NO 23) | EGGWTG (SEQ ID NO 25) | LLENER (SEQ ID NO 27) | |

H3N2

In some embodiments, the immunogenic composition comprises an HA recombinant protein or polypeptide derived from H3N2. In some embodiments, the recombinant H3N2 HA protein or polypeptide comprises a non-hypervariable amino acid residue at an amino acid position selected from Table 3, or any combination thereof. In some embodiments, the recombinant H3N2 HA protein or polypeptide comprises an amino acid that is a hypervariable-substitute at an amino acid position selected from Table 3, or any combination thereof.

TABLE 3

| List of Hypervariable Amino Acid Residues in H3N2 HA Protein | | | | | | | | | | | |
|---|---|---|---|---|---|---|---|---|---|---|---|
| 7L | 26T | 73Q | 110Y | 151T | 172H | 189Q | 214S | 242I | 296E | 391D | 494I |
| 9Y | 41I | 78E | 117D | 153S | 173L | 202G | 215S | 243P | 315R | 394N | 495G |
| 14V | 47N | 91Q | 137N | 154A | 174N | 205K | 218I | 245R | 327Q | 400L | 500G |
| 16A | 49R | 94G | 138N | 156I | 175F | 206D | 219T | 277R | 328S | 402G | 505N |
| 18K | 61N | 98K | 140S | 158R | 176K | 208I | 228A | 278S | 342K | 422I | 506V |
| 19L | 64I | 99K | 144T | 160N | 179A | 209F | 238R | 291G | 362M | 466K | 509D |
| 22Y | 66E | 107S | 147T | 161S | 187N | 212A | 239I | 292K | 363V | 468K | 522E |
| 25S | 69D | 108K | 149N | 171T | 188E | 213Q | 241N | 294K | 377R | 469K | 545V |
| 546A | 560I | 561R | 562C | 563N | 559N | | | | | | |

*residue numbering based on straight numbering of SEQ ID NO: 3. SEQ ID NO: 3 indicates these residues in hold In some embodiments, the recombinant H3N2 HA polypeptide comprises a highly conserved region of amino acid sequences. In some embodiments, the highly conserved region of amino acid sequences is selected from Table 4, or any combination thereof.

TABLE 4

| Highly Conserved Regions in H3N2 HA Protein | | | |
|---|---|---|---|
| LCLGHHA (SEQ ID NO 61) | GNLIAPRGYF (SEQ ID NO 63) | LKLATGMRN (SEQ ID NO 65) | FGAIAGF IENGWEG (SEQ ID NO 67) |
| KFHQIEKEF (SEQ ID NO 69) | DLTDSEM (SEQ ID NO 71) | LRENAED (SEQ ID NO 73) | |

Influenza B

In some embodiments, the immunogenic composition comprises an HA recombinant protein or polypeptide derived from influenza B. In some embodiments, the recombinant influenza B HA protein or polypeptide comprises a non-hypervariable amino acid residue at an amino acid position selected from Table 5, or any combination thereof. In some embodiments, the recombinant influenza B HA protein or polypeptide comprises an amino acid that is a hypervariable-substitute at an amino acid position selected from Table 5, or any combination thereof.

TABLE 5

| List of Hypervariable Amino Acid Residues in Influenza B HA Protein |
|---|
| 55H |
| 63E |
| 71K |
| 73L |
| 86K |
| 88T |
| 90K |
| 91I |
| 95R |
| 96V |

TABLE 5-continued

| List of Hypervariable Amino Acid Residues in Influenza B HA Protein |
|---|
| 123P |
| 131H |
| 132I |
| 137H |
| 141N |
| 144N |
| 151K |
| 152I |
| 161I |
| 163N |
| 164G |
| 165N |
| 177K |
| 178N |
| 180K |
| 181N |
| 183T |
| 187P |
| 188L |
| 190I |
| 195I |
| 197T |
| 213E |
| 217A |

TABLE 5-continued

| List of Hypervariable Amino Acid Residues in Influenza B HA Protein |
|---|
| 218K |
| 224K |
| 245G |
| 248N |
| 267V |
| 270S |
| 277T |
| 282I |
| 314K |
| 328E |
| 494E |
| 513R |
| 520D |
| 566I |
| 570V |

*residue numbering based on straight numbering of SEQ ID NO: 5. SEQ ID NO: 5 indicates these residues in bold.

In some embodiments, the recombinant influenza B HA polypeptide comprises a highly conserved region of amino acid sequences. In some embodiments, the highly conserved region of amino acid sequences is selected from Table 6, or any combination thereof.

TABLE 6

Highly Conserved Regions in Influenza B HA Protein

| | | | |
|---|---|---|---|
| VKTATQG<br>EVNVTG<br>(SEQ ID NO 194) | NCTDLDVAL<br>(SEQ ID NO 95) | TSGCFPIMH<br>DRTKIRQL<br>(SEQ ID NO 97) | NLLRGYE<br>(SEQ ID NO 99) |
| TMAWAVP<br>(SEQ ID NO 101) | EDGGLPQS<br>GRIWDYM<br>(SEQ ID NO 103) | LPLIGEAD<br>CLHE<br>(SEQ ID NO 105) | YGGLNKSKP<br>YYTG<br>(SEQ ID NO 107) |
| CPIWVKTPL<br>(SEQ ID NO 109) | GFFGAIAGF<br>LEGGWEGM<br>(SEQ ID NO 111) | AGWHGYTSHGAHG<br>(SEQ ID NO 113 | AVAADLKSTQEA<br>(SEQ ID NO 115) |
| KITKNLNSLSELE<br>(SEQ ID NO 117) | KNLQRLS<br>(SEQ ID NO 119) | EILELDEK<br>VDDLRADT<br>ISSQIELA<br>VLLSNEGI<br>INSEDEHL<br>LALERKLK<br>KMLGPSA<br>(SEQ ID NO 121) | IGNGCFETKH<br>KCNQTCLD<br>(SEQ ID NO 123) |
| AGEFSLPTFD<br>SLNITAASL<br>(SEQ ID NO 125) | HTILLYYSTA<br>ASSLAVTLM<br>(SEQ ID NO 127) | | |

Neuraminidase (NA)

In some embodiments, an immunogenic composition described herein comprises a neuraminidase (NA) recombinant protein, polypeptide or both. In some embodiments, the NA recombinant protein comprises a non-hypervariable amino acid substituted for a hypervariable amino acid residue. In some embodiments, the NA recombinant protein comprises a non-hypervariable amino acid replaced with an amino acid that is a hypervariable-substitute. In some embodiments, the NA polypeptide comprises a highly conserved region of amino acid sequences.

NA is an enzyme found on the surface of influenza that enables the virus to be released from the host cells. Neuraminidases are enzymes that cleave sialic acid groups from glycoproteins and are required for virus replication. The NA protein also functions during entry of virus into the respiratory tract. The epithelial cells are bathed in mucus, a complex protective coating that contains may sialic acid-containing glycoproteins. When influenza virions enter the respirator tract, they are trapped in mucus where they bind sialic acids. This interaction would prevent the viruses from binding to a susceptible cell were it not for the action of the NA protein. When a virus particle encounters a cell, it binds the sialic acid-containing receptor and is rapidly taken into the cell before the NA protein can cleave the carbohydrate from the cell surface.

The NA is a tetramer of four identical polypeptides. Each polypeptide contains about 470 amino acids arranged in four domains, an N-terminal cytoplasmic sequence, followed by a membrane-anchoring hydrophobic transmembrane domain and a thin stalk of variable length, ending in a globular "head" domain that carries the enzyme active site. Crystal structures of NA encompass the catalytically active heads, either proteolytically cleaved from the virus or engineered as a soluble secreted protein. The intact NA has not been crystallized, but a cryoelectron microscopy study of the X-31 (A/Aichi/68, H3N2) reassortant virus has revealed considerable detail at near atomic resolution. The structure confirms that the N2 NA protrudes slightly further than the HA from the viral membrane, that there are 40-50 NA spikes per virion, and that these occur in clusters amid 300-400 HA spikes on an average sized virion of diameter 120 nm.

H1N1

In some embodiments, the immunogenic composition comprises an NA recombinant protein or polypeptide derived from H1N1. In some embodiments, the recombinant H1N1 NA protein or polypeptide comprises a non-hypervariable amino acid residue at an amino acid position selected from Table 7, or any combination thereof. In some embodiments, the recombinant H1N1 NA protein or polypeptide comprises an amino acid that is a hypervariable-substitute at an amino acid position selected from Table 7, or any combination thereof.

TABLE 7

| List of Hypervariable Amino Acid Residues in H1N1 NA Protein |
| --- |
| 13I |
| 14C |
| 15M |
| 16T |
| 19M |
| 20A |
| 21N |
| 23I |
| 34I |
| 40L |
| 42N |
| 44N |
| 45Q |
| 46I |
| 47E |
| 48T |
| 52S |
| 53V |
| 59N |
| 64Q |
| 70S |
| 74F |
| 75A |
| 77G |
| 78Q |
| 79S |
| 80V |
| 81V |
| 82S |
| 84K |
| 86A |
| 93P |
| 94V |
| 101S |
| 106I |
| 126P |
| 130R |
| 149I |
| 157T |
| 163I |
| 166V |
| 173R |
| 188I |
| 189N |
| 200N |
| 214D |
| 220R |
| 221N |
| 222N |
| 232A |
| 234V |
| 241I |
| 248D |
| 249G |
| 250Q |
| 257R |
| 263I |
| 264V |
| 267V |
| 269M |
| 270N |
| 274Y |
| 275H |
| 285S |
| 286S |
| 287E |
| 288I |
| 289T |
| 311E |
| 314I |
| 321V |
| 329N |
| 331K |
| 332T |
| 336G |
| 339S |
| 340S |
| 341N |
| 344N |
| 351F |
| 354G |
| 365I |
| 366S |
| 367S |
| 369K |
| 382G |
| 385N |
| 386N |
| 389I |
| 393I |
| 395G |
| 397N |
| 398E |
| 416D |
| 427I |
| 430R |
| 432E |
| 449N |
| 450S |
| 452T |
| 453V |
| 454G |

*residue numbering based on straight numbering of SEQ ID NO: 2. SEQ ID NO: 2 indicates these residues in bold.

In some embodiments, the recombinant H1N1 NA polypeptide comprises a highly conserved region of amino acid sequences. In some embodiments, the highly conserved region of amino acid sequences is selected from Table 8, or any combination thereof.

TABLE 8

| Highly Conserved Regions in H1N1 NA Protein | | | |
| --- | --- | --- | --- |
| MNPNQKIITIGS (SEQ ID NO 29) | RIGSKGDVFV (SEQ ID NO 31) | REPFISCS (SEQ ID NO 33) | TFFLTQGAL LNDKHSNGT (SEQ ID NO 35) |
| KDRSPYR (SEQ ID NO 37) | FESVAWSASACHDG (SEQ ID NO 39) | WLTIGISGPD (SEQ ID NO 41) | GAVAVLKY (SEQ ID NO 155) |
| ILRTQESEC (SEQ ID NO 43) | YEECSCYPD (SEQ ID NO 45) | CVCRDNWHGS NRPWVSFNQNL (SEQ ID NO 47) | NGVWIGRTKS (SEQ ID NO 49) |

TABLE 8-continued

| Highly Conserved Regions in H1N1 NA Protein | | | |
|---|---|---|---|
| GFEMIWDPNGWT | WSGYSGSFV | RPCFWVEL | WTSGSSISFCGV |
| (SEQ ID NO 51) | QHPELTGL | (SEQ ID NO 55) | (SEQ ID NO 57) |
| | (SEQ ID NO 53) | | |
| WSWPDGAELPF | | | |
| (SEQ ID NO 59) | | | |

H3N2

In some embodiments, the immunogenic composition comprises an NA recombinant protein or polypeptide derived from H3N2. In some embodiments, the recombinant H3N2 NA protein or polypeptide comprises a non-hypervariable amino acid residue at an amino acid position selected from Table 9, or any combination thereof. In some embodiments, the recombinant H3N2 NA protein or polypeptide comprises an amino acid that is a hypervariable-substitute at an amino acid position selected from Table 9, or any combination thereof.

TABLE 9

| List of Hypervariable Amino Acid Residues in H3N2 NA Protein |
|---|
| 16T |
| 18S |
| 23F |
| 26I |
| 30I |
| 40Y |
| 41E |
| 42F |
| 43N |
| 44S |
| 45P |
| 46P |
| 51M |
| 52L |
| 56T |
| 62I |
| 73I |
| 75K |
| 81L |
| 82A |
| 93N |
| 126P |
| 127D |
| 140L |
| 143V |
| 147D |
| 149V |
| 150R |
| 155Y |
| 161N |
| 172K |
| 176I |
| 194V |
| 197D |
| 199K |
| 208N |
| 215I |
| 216V |
| 220K |
| 221E |
| 249K |
| 263V |
| 265T |
| 267T |
| 303V |
| 307I |
| 310Y |
| 313V |
| 329N |
| 331S |

TABLE 9-continued

| List of Hypervariable Amino Acid Residues in H3N2 NA Protein |
|---|
| 332S |
| 336H |
| 338L |
| 339D |
| 344E |
| 346G |
| 356D |
| 367S |
| 369K |
| 370L |
| 372S |
| 380I |
| 381E |
| 385N |
| 386P |
| 387N |
| 392I |
| 399D |
| 400R |
| 401G |
| 402N |
| 416S |
| 432E |
| 435E |
| 437L |
| 464I |
| 468P |

*residue numbering based on straight numbering of SEQ ID NO: 4. SEQ ID NO: 4 indicates these residues in bold.

In some embodiments, the recombinant H3N2 NA polypeptide comprises a highly conserved region of amino acid sequences. In some embodiments, the highly conserved region of amino acid sequences is selected from Table 10, or any combination thereof.

TABLE 10

| Highly Conserved Regions in H3N2 NA Protein | | |
|---|---|---|
| QFALGQGTT | AWSSSSC | LRTQESEC |
| (SEQ ID NO 75) | (SEQ ID NO 77) | (SEQ ID NO 79) |
| EECSCYP | CSGLVGDTPR | GVKGWAFD |
| (SEQ ID NO 81) | (SEQ ID NO 83) | (SEQ ID NO 85) |
| NRCFYVELIRG | VFCGTSGTYG | GSWPDGA |
| (SEQ ID NO 87) | (SEQ ID NO 89) | (SEQ ID NO 91) |

Influenza B

In some embodiments, the immunogenic composition comprises an NA recombinant protein or polypeptide derived from influenza B. In some embodiments, the recombinant influenza B NA protein or polypeptide comprises a non-hypervariable amino acid residue at an amino acid position selected from Table 11, or any combination thereof. In some embodiments, the recombinant influenza B NA protein or polypeptide comprises an amino acid that is a hypervariable-substitute at an amino acid position selected from Table 11, or any combination thereof.

TABLE 11

| List of Hypervariable Amino Acid Residues in Influenza B NA Protein |
|---|
| 42P |
| 45I |
| 49T |
| 61Q |
| 65R |
| 67A |
| 68T |
| 73L |
| 74L |
| 107T |
| 121V |
| 126N |
| 149G |
| 172I |
| 187K |
| 199N |
| 205V |
| 220N |
| 221N |
| 236N |
| 245S |
| 249V |
| 296R |
| 321D |
| 330N |
| 341D |
| 343D |
| 344K |
| 359K |
| 372K |
| 374E |
| 385G |
| 390A |
| 393D |
| 396A |
| 397F |
| 402V |
| 403S |
| 405K |
| 437E |
| 464D |
| 466A |

*residue numbering based on straight numbering of SEQ ID NO: 6. SEQ ID NO: 6 indicates these residues in bold.

In some embodiments, the recombinant influenza B NA polypeptide comprises a highly conserved region of amino acid sequences. In some embodiments, the highly conserved region of amino acid sequences is selected from Table 12, or any combination thereof.

TABLE 12

| Highly Conserved Regions in Influenza B NA Protein | | | |
|---|---|---|---|
| HFALTHYAAQPG (SEQ ID NO 131) | DRNKLRHL (SEQ ID NO 133) | AWSGSACHDG (SEQ ID NO 135) | KYGEAYT DTYHSY (SEQ ID NO 137) |
| LRTQESACNCI (SEQ ID NO 139) | CRFLKIREGR (SEQ ID NO 141) | HTEECTCGFA (SEQ ID NO 143) | YTAKRPFVKL (SEQ ID NO 145) |
| KGGFVHQR (SEQ ID NO 147) | GRWYSRT (SEQ ID NO 149) | EPGWYSFGFE (SEQ ID NO 151) | EMVHDGG (SEQ ID NO 153) |
| ALLISPHRFGE (SEQ ID NO 129) | | | |

M2 Ectodomain

In some embodiments, an immunogenic composition described herein comprises an M2 ectodomain (M2e) recombinant protein, polypeptide or both. In some embodiments, the M2e recombinant protein comprises a non-hypervariable amino acid substituted for a hypervariable amino acid residue. In some embodiments, the M2e recombinant protein comprises a non-hypervariable amino acid replaced with an amino acid residue that is a hypervariable-substitute. In some embodiments, the M2e polypeptide comprises a highly conserved region of amino acid sequences.

The M2 protein is a surface protein on the influenza virion encoded by the M segment. The M segment encodes M1 from unspliced mRNA and M2 protein by mRNA splicing. M2 forms homotetramers and possesses ion channel activity that allows for acidification of the inside of the virion during endocytosis and facilitates the dissociation of the matrix protein M1 from viral ribonucleoprotein complexes. The M2e, which is the exposed portion of the M2 protein found on the virion membrane, is highly conserved among influenza strains. Accordingly, the M2e protein is a target for universal influenza vaccine approaches.

In some embodiments, M2e protein sequences are obtained and aligned using a method described herein (e.g., the Dawn method) to identify hypervariable amino acid residues subject to antigenic shift/drift, and highly conserved regions of amino acid sequences.

In some embodiments, the immunogenic composition comprises an M2e recombinant protein or polypeptide derived from H1N1. In some embodiments, the recombinant H1N1 M2e protein or polypeptide comprises a non-hypervariable amino acid residue at a hypervariable amino acid residue, or any combination thereof. In some embodiments, the recombinant H1N1 M2e polypeptide comprises a highly conserved region of amino acid sequences, or any combination thereof.

In some embodiments, the immunogenic composition comprises an M2e recombinant protein or polypeptide derived from H3N2. In some embodiments, the recombinant H3N2 M2e protein or polypeptide comprises a non-hypervariable amino acid residue at a hypervariable amino acid residue, or any combination thereof. In some embodiments, the recombinant H3N2 M2e polypeptide comprises a highly conserved region of amino acid sequences, or any combination thereof.

In some embodiments, the immunogenic composition comprises an M2e recombinant protein or polypeptide derived from influenza B. In some embodiments, the recombinant influenza B M2e protein or polypeptide comprises a non-hypervariable amino acid residue at a hypervariable amino acid residue, or any combination thereof. In some embodiments, the recombinant influenza B M2e polypeptide comprises a highly conserved region of amino acid sequences, or any combination thereof.

Additional Influenza Proteins

In some embodiments, an immunogenic composition described herein comprises at least one additional influenza protein, polypeptides or both. In some embodiments the at least one additional influenza protein is selected from NP, M1, PA, PB2, PB2, NS1, and NS2. In some embodiments, the additional influenza protein comprises a non-hypervariable amino acid substituted for a hypervariable amino acid residue. In some embodiments, the additional influenza protein comprises a non-hypervariable amino acid replaced with an amino acid residue that is a hypervariable-substitute. In some embodiments, the additional influenza protein comprises a highly conserved region of amino acid sequences.

The nucleoprotein molecules encapsidate the viral single-stranded RNAs. Nucleoprotein molecules also participate in the nuclear import and export of vRNPs and viral replication, and interact with host proteins. The influenza viral polymerase (P complex) is a heterotrimer of subunits PA, PB1 and PB2. The P complex carries out mRNA transcription and replication of the influenza virus. The PA subunit N domain has a cation-dependent endonuclease active-site core; the catalytic residues His41, Glu80, Asp108 and Glu119 are conserved among influenza A subtypes and strains. The nonstructural protein NS1 binds double-stranded RNA (dsRNA) in a non-sequence specific manner. The NS1 protein has a conserved residue, Arg39 that interact with dsRNA. Accordingly, the additional influenza proteins are also targets for universal influenza vaccine approaches.

In some embodiments, the additional influenza protein sequences are obtained and aligned using a method described herein (e.g., the Dawn method) to identify hypervariable amino acid residues subject to antigenic shift/drift, and highly conserved regions of amino acid sequences.

In some embodiments, the immunogenic composition comprises an additional influenza protein or polypeptide derived from H1N1. In some embodiments, the recombinant H1N1 protein or polypeptide comprises a non-hypervariable amino acid residue at a hypervariable amino acid residue, or any combination thereof. In some embodiments, the recombinant H1N1 polypeptide comprises a highly conserved region of amino acid sequences, or any combination thereof.

In some embodiments, the immunogenic composition comprises an additional influenza protein or polypeptide derived from H3N2. In some embodiments, the recombinant H3N2 protein or polypeptide comprises a non-hypervariable amino acid residue at a hypervariable amino acid residue, or any combination thereof. In some embodiments, the recombinant H3N2 polypeptide comprises a highly conserved region of amino acid sequences, or any combination thereof.

In some embodiments, the immunogenic composition comprises an additional influenza protein or polypeptide derived from influenza B. In some embodiments, the recombinant influenza B protein or polypeptide comprises a non-hypervariable amino acid residue at a hypervariable amino acid residue, or any combination thereof. In some embodiments, the recombinant influenza B polypeptide comprises a highly conserved region of amino acid sequences, or any combination thereof.

In some embodiments, the immunogenic composition comprises an additional influenza protein or polypeptide having a highly conserved regions as annotated in any one of SEQ ID NOs: 171-193. In some embodiments, the protein or polypeptide comprises a non-hypervariable amino acid residue at an amino acid residue that is a hypervariable amino acid residue as annotated in any one of SEQ ID NOs: 171-193. In some embodiments, the protein or polypeptide comprises a hypervariable-substitute at an amino acid residue that is a hypervariable amino acid residue as annotated in any one of SEQ ID NOs: 171-193.

Methods for Identifying Hypervariable and Conserved Influenza Residues

In some embodiments, the present disclosure provides methods for identifying hypervariable and conserved residues in an influenza viral protein between types and/or subtypes of strains. In some embodiments, the hypervariable amino acid residues identified by the methods described herein are substituted with a non-hypervariable amino acid (e.g., alanine). In some embodiments, the hypervariable amino acid residues identified by the methods described herein are substituted with an amino acid residue that is a hypervariable-substitute (e.g., alanine). In some embodiments, the highly conserved regions of amino acids are used to generate polypeptides for peptide vaccines and/or as targets of nucleic acids.

In some embodiments, the present disclosure provides methods for evaluating the role of hypervariable and conserved residues on the ability to induce an immune response (e.g., production of antibodies).

Sequence Alignment—Dawn Method

Protein sequence evolutionary conservation analysis improves understanding of protein structure, function, and disease. Multiple sequence alignments of different isolates, orthologs, paralogs, and functional domains provide essential insights into protein function and structure. Evolutionary conservation level is directly correlated with likelihood of missense mutations' functional impact.

Missense mutations are typically either deleterious or neutral in regards to function impact. Deleterious mutations experience negative selection. Neutral mutations are not positively or negatively selected and can drift through populations. A few mutations experience positive selection and become fixed within populations. Aligning sequences from different species enable the estimation of residue functional importance based on sequence divergence of evolutionarily related proteins. Aligned residues that are identical are composed of a combination of functionally important residues and residues not observed to change due to stochastic chance. Aligned residue positions that are different can represent (1) functionally neutral residues, (2) positions that allow limited conservative residue changes of similar amino acid residues, and (3) positions with alignment errors (this varies by alignment tool used).

A protein enzyme typically consists of a globular domain with a conserved inner core with non-conserved residues observed on the solvent exposed surface. Protein folding includes structures like random coils, alpha helices, beta sheets, and loops/turns. Unlike a ball of yarn, protein peptide strands fold into the tertiary structure with the peptide strand traversing into the interior until typically turning in a solvent exposed loop. Residues in the inner core are typically conserved with amino acid substitutions likely impacting protein folding, structure, and/or function. These interior segments are typically what motif signature models such as, Profile analysis, Psi-Blast, and HAMMR, are derived from or trained on. See e.g., Gribskov, M. et al., *Proc. Natl. Acad. Sci.,* 84: 4355-4358 (1987); Altschul, S. F., et al., *Nucl. Acids Res.* 25:3389-3402 (1997); Eddy, S. R., *Bioinformatics,* 14:755-763 (1998). Ideally, these are the segments that should be aligned in a multiple sequence alignment without gapping allowed within each segment. Small insertions and gaps are observed in exterior turns/loops. Pascarella, S., and P. Argos, P., J Mol. Biol., 224: 461-471 (1992).

Multiple sequence alignment of protein sequences provides numerous insights into protein structures and functions. Available solutions for generating multiple sequence alignments is slow, and the resulting alignments are plagued by frequent over gapping. Scientists routinely realign sub-segments within alignments to enhance alignment quality. Algorithm developers have treated protein sequences as text strings for comparisons. Some advanced algorithms include knowledge extracted from motifs, profiles, and structures.

In some embodiments, protein sequences are aligned using the Dawn method.

The Dawn multiple sequence alignment and conservation analysis tool uses conserved residues as anchors such that evolutionarily related sequences can be added to the alignment incrementally. This approach reduces the complexity of creating multiple sequence alignment, or of comparing every sequence to every other sequence. This works for both evolutionarily close or distant sequences and combinations of both.

The ability to identify distant orthologs is directly correlated with the proportion of essential residues in a protein. Doolittle, R. F., OF URFS AND ORFS: A Primer on How to Analyze Derived Amino Acid Sequences: University Science Books, (1986), characterized sequence alignments below 25% identity as being the "Twilight Zone"—a limit on sequence alignment approaches. Below 20% identify is termed the "Midnight Zone", an accepted theoretical limit to sequence analysis techniques.

Dawn aligns sequences based on the Divergence Model of protein evolution, and can align and characterize large numbers of related protein sequences rapidly. Using this tool, a performance improvement of at least two orders of magnitude improvement over current methods. Dawn is applied to three pressing challenges: identification of anti-viral targets for therapeutics, multigene family alignment, and analysis of human missense mutations (variants). Dawn implements two concepts of (1) conserved core segments and (2) insertions in loops. Using the sequence analysis technique, Dawn is able to align some paralogs deep into the sequence alignment Twilight and Midnight Zones.

In some embodiments, the workflow for multiple sequence alignment strategy comprises:

1. Identify highly conserved protein segments and use these as vertical segments throughout the multiple sequence alignment;
2. Place insertions and gaps in candidate loop segments to align conserved segments. To minimize alignment gaps, align insertions and gaps in a loop region in overlapping alignment positions unless local sequence identity indicate two likely independent mutation events have likely occurred;
3. Residues in two homologs share high sequence identity between conserved segments that are ordered within a domain. Unrelated sequences can share common simple sequence motifs, but these can be ignored;
4. Conserved segments can be approximated by common k-mers between sequences. Multiple homologs will share a common set of ordered k-mers. Multiple unrelated sequences will not share ordered k-mer sequences outside of expected random sharing.

In some embodiments, the following definitions are used to define conserved segments:

- Ai=Multiple sequence alignment position, i, for sequence of interest;
- C(Ai)=−V with V>0—nonconserved position with V different amino acids observed at this alignment position;
- C(Ai)=0—nonconserved position with residue observed missing in sequences for this gene;
- C(Ai)=1—conserved positions for all sequences for this gene for organisms of the same taxonomic class;
- C(Ai)=1.T—conserved position for all sequences for this gene for taxonomic class of this sequence and T-1 additional taxonomic classes; and
- C(Ai)=V with V>1—conserved position with residue conserved in all sequences for V genes.

In some embodiments, the following definitions are used to define conserved variable or non-conserved segments:

- V(Ai)=number of nonconserved residues observed at alignment position, i, for the taxonomic class of interest. Allowable conservative substitutions defined by Bottema were used to define observed nonconservative substitutions. Bottema, C. D. K., et al., *Am J Hum Genet*, (49):820-838 (1991).

In some embodiments, an algorithm, MSAQ-compute.py (Multiple sequence alignment quality compute), developed in Python, is used to evaluate the quality of multiple sequence alignments. The algorithm accepts an MSA in Clustal format as an input, as well as optional parameters for the number of residues that should not be scored at the beginning and end of the alignment. This accommodates cases of partial sequence overlap and avoids imposing a penalty for otherwise good alignments with excess residues at the beginning or end. The algorithm generates an index of all scored positions within the MSA input file and tallies reported residues at each position to generate a consensus sequence for the alignment.

For each sequence in the MSA, the algorithm computes the number of residues that match the consensus sequence, the number of residues that are different from the corresponding position in the consensus sequence (mismatch), the total number of gap characters in the aligned sequence, and the total number of unique gaps in the aligned sequence. These values are reported in a "details" file generated by the algorithm. Additionally, these values are averaged across all sequences in the MSA to generate average match and average mismatch metrics.

The average length of all gaps in the MSA is also reported as well as the total number of gaps present in the alignment (summed across all sequences). Finally, based on the rationale that any gaps in a high quality alignment should overlap (i.e. input sequences should have alignment gaps at roughly the same positions), the number of non-overlapping gaps is computed. To generate this value, all gaps in the alignment are mapped to positions in the consensus sequence to generate ranges of gap positions. The number of such non-overlapping ranges is reported.

In some embodiments, viral protein sequences are selected from GenBank for influenza. For each selected virus protein, subsets are evaluated to measure execution runtimes using a single Linux core (no parallelization).

Alanine Scanning

The methods described supra are used to identify hyper-variable amino acid residues. In some embodiments, the importance of a hypervariable amino acid residue for inducing an immune response is determined by alanine scanning.

As described herein, alanine scanning is a technique used to determine the contribution of a specific wild-type residue to the stability or function(s) (e.g., inducing an immune response) of given protein or polypeptide. The technique involves the substitution of an alanine residue for a wild-type residue in a polypeptide, followed by an assessment of the stability or function(s) (e.g., inducing an immune response) of the alanine-substituted derivative or mutant polypeptide and comparison to the wild-type polypeptide. In some embodiments, the residues identified as not critical are further evaluated to modulate the induction of an immune response. A non-limiting example of such analysis is deep mutational scanning. This method allows for the evaluation of large numbers of mutations. Other methods for analyzing the effect of amino acid residue mutations are known in the art. For example, arginine/glutamic acid scanning is employed to study the effects of bulky, charged amino acid residues on antigen binding. In an embodiment, an arginine amino acid in the hypervariable region is replaced by glutamic acid.

Inducing T Cell Responses with Highly Conserved Regions

T cell immune response plays an important role in eliciting and maintaining protective immunity against influenza virus. In a recent human study, repeated influenza virus boosted multifunctional memory CD4+ T cell populations. Specifically, IFN-γ and TNF-α secreting CD4 cell population have been shown to boost anti-virus antibody titers after repeated vaccination, and is correlated with maintenance of protective antibody titers. Trieu, M. C., et al., npj Vaccines, 3:37 (2018). doi:10.1038/s41541-018-0069-1. Similarly, administration of a combination vaccine comprising trivalent influenza vaccine and a VLP based vaccine showed enhanced CD8+ and CD4+ immune response, and CD4+ T-cell response is correlated with neutralization antibody titers. Skibinski, D. A. G., et al., Sci Rep. 8:18007 (2018).

In some embodiments, the present disclosure provides a polypeptide comprising highly conserved regions of amino acid sequences within a viral protein. In some embodiments, the conserved region is a continuous stretch of at least 7, 8, 9, 10, 11, or 12 invariant or minimally variable amino acid residues. In some embodiments, the polypeptide has 100% identity to a highly conserved region provided herein. In some embodiments, the polypeptide has 99%, 98%, 97%, 96%, 95%, 94%, 93%, 92%, 91% or 90% identity to a highly conserved region provided herein.

In some embodiments, a polypeptide comprising a highly conserved region is operably linked to at least one additional polypeptide comprising a different highly conserved region. In some embodiments, a polypeptide comprising a highly conserved region is operably linked to at least one additional polypeptide comprising the same highly conserved region. In some embodiments, 2, 3, 4, 5, 6, 7, 8, 9, 10, 11, 12, 13, 14, 15, 16, 17, 18, 19 or 20 polypeptides comprising highly conserved regions are operably linked to each other, wherein each polypeptide is the same or different. In some embodiments, at least 10, at least 20, at least 30, at least 40 or at least 50 polypeptides comprising highly conserved regions are operably linked to each other, wherein each polypeptide is the same or different.

In some embodiments, a polypeptide or polypeptides operably linked to each other, induce a T cell response, such as virus-specific CD8+ or CD4+ T cell responses. In some embodiments, an virus-specific CD8+ T cell response comprises CD8+ T cell proliferation or CD8+ T cell cytokine production or both, are induced. In some embodiments, $CD8^+$ T cell cytokine production increases by at least 5% or at least 10% or at least 15% or at least 20% or at least 25% or at least 30% or at least 35% or at least 40% or at least 45% or at least 50%. In some embodiments, the percentage of $CD8^+$ T cells among the total T cell population increases by at least 5% or at least 10% or at least 15% or at least 20% or at least 25% or at least 30% or at least 35% or at least 40% or at least 45% or at least 50%.

In one embodiment, the disclosure provides a method for eliciting T cell response to conserved polypeptides of influenza viruses, the method comprising administering to a subject in need thereof an immunogenic composition comprising at least one influenza virus polypeptide comprising high conserved amino acid sequence, wherein the T cell response immune response to the highly conserved amino acid sequence is elicited in the subject. In one embodiment, eliciting T cell immune response in a subject comprises stimulating cytokine production (e.g., IFN-γ or TNF-α).

In another embodiment, eliciting an immune response in a subject comprises stimulating virus polypeptide-specific CD4+ or CD8+ T cell activity, e.g., priming, proliferation and/or survival (e.g., increasing the effector/memory T cell population). In one aspect, eliciting a T-cell immune response in a subject comprises stimulating virus-specific CD4+ T cell activity (e.g., increasing helper T cell activity). In other aspects, the CD4+ T cell immune response stimulates cell responses (e.g., increasing antibody production). In some embodiments, enhancing T cell immune response in a subject comprises stimulating cytokine production, stimulating antigen-specific CD8+ T cell responses, stimulating antigen-specific CD4+ helper cell responses, increasing the effector memory CD62Llo T cell population, stimulating B cell activity or stimulating virus-specific antibody production, or any combination of the foregoing responses.

In some embodiments, the enhanced immune response comprises an virus-specific CD8+ T cell response, wherein the CD8+ T cell response comprises an increase in the percentage of effector memory CD62Llo T cells among CD8+ T cells.

Inducing B Cell Responses by Targeting Hypervariable Amino Acid Residues

Most neutralizing antibodies bind to the loops that surround the virus receptor binding site and interfere with receptor binding and attachment. Since these loops are highly variable, most antibodies targeting these regions are strain-specific, and elicit limited, strain-specific immunity. Fully human monoclonal antibodies against influenza virus hemagglutinin with broad cross-neutralizing potency have been generated. Functional and structural analysis have revealed that these antibodies interfere with the membrane fusion process and are directed against highly conserved epitopes in the stem domain of the influenza HA protein (Throsby et al., Plos One 12(3): 1-15 (2008); Ekiert et al., Science 324:246-251 (2009), US2009/0311265, US2012/0039898, US2014/0120113).

In some embodiments, the present disclosure provides an influenza viral protein or fragment thereof, wherein hypervariable amino acid residues are replaced with a non-hypervariable amino acid. Non-hypervariable amino acid residues include, but are not limited to, alanine and glycine. In some embodiments, a non-hypervariable amino acid residue is referred to as a hypervariable-substitute. In some embodiments, the hypervariable amino acid residues are replaced with alanine, glycine, valine, leucine, isoleucine, and methionine. In some embodiments, the hypervariable amino acid residues are replaced with alanine and glycine. In some embodiments, the hypervariable amino acids are replaced with the exemplary and/or preferred amino acids to preserve the conformation of the viral protein and to minimize disruption to adjacent or overlapping conserved regions. In some embodiments, bulky and charged arginine amino acid residues are replaced with glutamic acid residues. In some embodiments, the polypeptide comprises a fragment of the amino acid sequence of the viral proteins. In some embodiments, the fragment comprises the entire amino acid sequence of the viral protein. In some embodiments, viral proteins and fragments thereof can be used in combination.

In some embodiments, the present disclosure provides immunogenic composition comprising at least viral protein or fragment thereof wherein 1-5, 6-10, 11-15, 16-20, 21-25, 26-30, 31-35, 36-40, 41-45, 46-50, 51-55, 56-60 hypervariable amino acid residues are replaced with non-hypervariable amino acid residues. In some embodiments at one, two, three, four, five or more hypervariable amino acids are replaced with non-hypervariable amino acid residues.

In some embodiments, the present disclosure provides immunogenic composition comprising at least viral protein or fragment thereof wherein 1-5, 6-10, 11-15, 16-20, 21-25, 26-30, 31-35, 36-40, 41-45, 46-50, 51-55, 56-60 hypervariable amino acid residues are replaced with amino acid residues that are hypervariable-substitute. In some embodiments at one, two, three, four, five or more hypervariable amino acids are replaced with an amino acid residue that is a hypervariable-substitute.

In some embodiments, substituting the hypervariable amino acid residues with non-hypervariable amino acid residues directs the immune response away from the residues subject to antigenic drift/shift and induces an immune response to the highly conserved regions of amino acid sequences. By targeting the highly conserved regions, such polypeptides can be used for protection against current and yet to exist influenza strains.

In some embodiments, the polypeptides described herein induce a B cell response (e.g., antibody production). In some embodiments, the B cell response is an antigen-specific antibody response. In some embodiments, the B cell response elicit neutralizing antibodies directed to the highly conserved regions in the viral protein. In some embodiments, the neutralizing antibodies are neutralizing against multiple strains of influenza viruses.

In another aspect, the disclosure provides a method of directing the specificity of an B cell immune response in a subject by administering to a subject an immunogenic composition comprising the viral protein, wherein one or more hypervariable amino acid residues of the virus protein are replaced with non-hypervariable amino acid residues.

In another embodiment, administration of immunogenic composition having the amino acid residue substitution results in the immune response to be directed to an highly conserved B cell epitope, and thus eliciting one or more protective neutralizing antibodies. In some embodiments, the neutralizing antibodies provide protective immunity against multiple strains of influenza virus.

Targeting Highly Conserved Regions with Nucleic Acid Molecules

In some embodiments, the present disclosure provides nucleic acid molecules having substantial complementarity to a highly conserved region of amino acid residues. Such nucleic acid molecules are capable of disrupting the transcription and/or translation of a viral protein comprising the base sequence.

Exemplary nucleic acid molecules that can modulate protein function include antisense oligonucleotides and RNA interference molecules (e.g., small interfering RNA (siRNA), microRNA (miRNA) and shRNA).

Antisense oligonucleotides are capable of blocking or decreasing the expression of a desired target gene by targeting nucleic acids encoding the gene or subunit thereof. Methods are known to those of ordinary skill in the art for the preparation of antisense oligonucleotide molecules that will specifically bind one or more target gene(s) without cross-reacting with other polynucleotides. Exemplary sites of targeting include, but are not limited to, the initiation codon, the 5' regulatory regions, including promoters or enhancers, the coding sequence, including any conserved consensus regions, and the 3' untranslated region. In some embodiments, the antisense oligonucleotides are about 10 to about 100 nucleotides in length, about 15 to about 50 nucleotides in length, about 18 to about 25 nucleotides in length, or more. In certain embodiments, the oligonucleotides further comprise chemical modifications to increase nuclease resistance and the like, such as, for example, phosphorothioate linkages and 2'-O-sugarmodifications known to those of ordinary skill in the art.

RNA interference (RNAi) is a biological process in which RNA molecules inhibit gene expression or translation by neutralizing targeted mRNA molecules. Specifically, RNAi refers to a post-transcriptional silencing mechanism initiated by small double-stranded RNA molecules that suppress expression of genes with sequence homology. Key to the mechanism of RNAi are small interfering RNA (siRNA) strands, which have complementary nucleotide sequences to a targeted messenger RNA (mRNA) molecule. siRNAs are short, single-stranded nucleic acid molecules capable of inhibiting or down-regulating gene expression in a sequence-specific manner; see, for example, Zamore et al., Cell 101:25 33 (2000); Bass, Nature 411:428-429(2001); Elbashir et al., Nature 411:494-498 (2001); and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914. Methods of preparing a siRNA molecule for use in gene silencing are described in U.S. Pat. No. 7,078,196, which is hereby incorporated by reference. Generally, one would prepare siRNA molecules that will specifically target one or more mRNAs without cross-reacting with other polynucleotides. siRNA molecules can be generated by methods known in the art, such as by typical solid phase oligonucleotide synthesis, and often will incorporate chemical modifications to increase half-life and/or efficacy of the siRNA agent, and/or to allow for a more robust delivery formulation. Alternatively, siRNA molecules are delivered using a vector encoding an expression cassette for intracellular transcription of siRNA.

Nucleic Acids Encoding Influenza Polypeptides

In some aspects, the polypeptides described herein are encoded by a nucleic acid molecule (e.g., DNA, RNA).

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence. Transcription and translation of coding sequences are typically regulated by "control elements," including, but not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

A "promoter" is a nucleotide sequence which initiates transcription of a polypeptide-encoding polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. In addition, such promoters can also have tissue specificity, for example, the CD80 promoter is only inducible in certain immune cells, and the myoD promoter is only inducible in muscle cells. It is intended that the term "promoter" or "control element" includes full-length promoter regions and functional (e.g., controls transcription or translation) segments of these regions. A promoter is "derived from" a gene encoding a co-stimulatory molecule if it has the same or substantially the same basepair sequence as a region of the promoter region of the co-stimulatory molecule, complements thereof, or if it displays sequence identity as described below.

A "vector" is capable of transferring gene sequences to target cells (e.g., viral vectors, non-viral vectors, particulate carriers, and liposomes). Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as viral vectors.

Nucleotide sequences selected for use in the present disclosure can be derived from known sources, for example, by isolating the same from cells containing a desired gene or nucleotide sequence using standard techniques. Similarly, the nucleotide sequences can be generated synthetically using standard modes of polynucleotide synthesis that are well known in the art. See, e.g., Edge et al. (1981) Nature 292:756-762; Nambair et al. (1994) Science 223:1299-1301: Jay et al. (1984) J. Biol. Chem. 259:6311-6317. Generally, synthetic oligonucleotides can be prepared by either the phosphotriester method as described by Edge et al., supra, and Duckworth et al. (1981) Nucleic Acids Res. 9:1691-1706, or the phosphoramidite method as described by Beaucage et al. (1981) Tet. Letts. 22:1859, and Matteucci et al. (1981) J. Am. Chem. Soc.103:3185.

Another method for obtaining nucleic acid sequences for use herein is by recombinant means. Thus, a desired nucleotide sequence can be excised from a plasmid carrying the same using standard restriction enzymes and procedures. Site specific DNA cleavage is performed by treating with the suitable restriction enzyme (or enzymes) under conditions which are generally understood in the art, and the particulars of which are specified by manufacturers of commercially available restriction enzymes. If desired, size separation of the cleaved fragments may be performed by polyacrylamide gel or agarose gel electrophoresis using standard techniques.

Yet another convenient method for isolating specific nucleic acid molecules is by the polymerase chain reaction (PCR). Mullis et al. (1987) Methods Enzymol. 155:335-350. This technique uses DNA polymerase, usually a thermostable DNA polymerase, to replicate a desired region of DNA. The region of DNA to be replicated is identified by oligonucleotides of specified sequence complementary to opposite ends and opposite strands of the desired DNA to prime the replication reaction. The product of the first round of replication is itself a template for subsequent replication, thus repeated successive cycles of replication result in geometric amplification of the DNA fragment delimited by the primer pair used. This method also allows for the facile addition of nucleotide sequences onto the ends of the DNA product by incorporating these added sequences onto the oligonucleotide primers (see, e.g., PCR Protocols, A Guide to Methods and Applications, Innis et al (eds) Harcourt Brace Jovanovich Publishers, NY (1994)). PCR conditions used for each amplification reaction are empirically determined. A number of parameters influence the success of a reaction. Among them are annealing temperature and time, extension time, Mg2+ and ATP concentration, pH, and the relative concentration of primers, templates, and deoxyribonucleotides.

Once coding sequences for desired proteins have been prepared or isolated, such sequences can be cloned into any suitable vector or replicon. Numerous cloning vectors are known to those of skill in the art, and the selection of an appropriate cloning vector is a matter of choice. Ligations to other sequences are performed using standard procedures, known in the art.

In some aspects, a nucleic acid molecule described herein is provided in an expression vector. In some embodiments, the vector comprises the nucleic acid molecule that codes for the peptides operatively linked to appropriate expression control sequences. Methods of affecting this operative linking, either before or after the nucleic acid molecule is inserted into the vector, are well known. Expression control sequences include promoters, activators, enhancers, operators, ribosomal nuclease domains, start signals, stop signals, cap signals, polyadenylation signals, and other signals involved with the control of transcription or translation.

Viral vectors that are suitable for use include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

A number of viral based systems have been used for gene delivery. For example, retroviral systems are known and generally employ packaging lines which have an integrated defective provirus (the "helper") that expresses all of the genes of the virus but cannot package its own genome due to a deletion of the packaging signal, known as the psi sequence. Thus, the cell line produces empty viral shells. Producer lines can be derived from the packaging lines which, in addition to the helper, contain a viral vector which includes sequences required in cis for replication and packaging of the virus, known as the long terminal repeats (LTRs). The gene of interest can be inserted in the vector and packaged in the viral shells synthesized by the retroviral helper. The recombinant virus can then be isolated and delivered to a subject. (See, e.g., U.S. Pat. No. 5,219,740.) Representative retroviral vectors include but are not limited to vectors such as the LHL, N2, LNSAL, LSHL and LHL2 vectors described in e.g., U.S. Pat. No. 5,219,740, incorporated herein by reference in its entirety, as well as derivatives of these vectors, such as the modified N2 vector described herein. Retroviral vectors can be constructed using techniques well known in the art. See, e.g., U.S. Pat. No. 5,219,740; Mann et al. (1983) Cell 33:153-159.

Adenovirus based systems have been developed for gene delivery and are suitable for delivering the nucleic acid molecules described herein. Human adenoviruses are double-stranded DNA viruses which enter cells by receptor-mediated endocytosis. These viruses are particularly well suited for gene transfer because they are easy to grow and manipulate and they exhibit a broad host range in vivo and in vitro. For example, adenoviruses can infect human cells of hematopoietic, lymphoid and myeloid origin. Furthermore, adenoviruses infect quiescent as well as replicating target cells. Unlike retroviruses which integrate into the host genome, adenoviruses persist extrachromosomally thus minimizing the risks associated with insertional mutagenesis. The virus is easily produced at high titers and is stable so that it can be purified and stored. Even in the replication-competent form, adenoviruses cause only low level morbidity and are not associated with human malignancies. Accordingly, adenovirus vectors have been developed which make use of these advantages. For a description of adenovirus vectors and their uses see, e.g., Haj-Ahmad and Graham (1986) J. Virol. 57:267-274; Bett et al. (1993) J. Virol. 67:5911-5921; Mittereder et al. (1994) Human Gene Therapy 5:717-729; Seth et al. (1994) J. Virol. 68:933-940; Barr et al. (1994) Gene Therapy 1:51-58; Berkner, K. L. (1988) BioTechniques 6:616-629; Rich et al. (1993) Human Gene Therapy 4:461-476. Adeno-associated viral vector (AAV) can also be used to administer the polynucleotides described herein. AAV vectors can be derived from any AAV serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes, but retain one or more functional flanking inverted terminal repeat (ITR) sequences. Functional ITR sequences are necessary for the rescue, replication and packaging of the AAV virion. Thus, an AAV vector includes at least those sequences required in cis for replication and packaging (e.g., functional ITRs) of the virus. The ITR sequence need not be the wild-type nucleotide sequence, and may be altered, e.g., by the insertion, deletion or substitution of nucleotides, so long as the sequence provides for functional rescue, replication and packaging.

AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is bounded (5' and 3') with functional AAV ITR sequences. Suitable AAV constructs can be designed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179:1867-1875.

Models for Assessing Prophylactic and Therapeutic Efficacy

In Vitro Models

In some embodiments, in vitro evaluation are utilized to screen vaccine candidates. See e.g., Tapia-Calle, G., et al., Vaccines (Basel) 5(3) pii: E21 (2017). doi: 10.3390/vaccines5030021. Dendritic cells (DCs) play an important in the development of innate and adaptive immune responses. In a study, a DC line (MUT-3) and primary monocyte-derived DCs (Mo-DCs) were employed to screen whole inactivated and subunit influenza vaccines. The Mo-DCs were stimulated with both vaccines and showed upregulated protein expression of activation markers (MHC II, CD86 and CD40) and changes in cytokine secretion in response to whole inactivated vaccines. The Mo-DCs additionally showed increase in gene coding for surface markers of DC cells. The results show that Mo-DCs derived from either fresh or frozen/thawed PBMCs could be utilized to screen vaccine candidates.

In another embodiment, long-term cultures of unfractionated PBMCS were employed to assess recall T cell responses to vaccine candidates. See e.g., Tapia-Calle, G., et al., Vaccines (Basel) 7(4). pii: E181 (2019). doi: 10.3390/vaccines7040181. After stimulation with whole inactivated and subunit influenza vaccines. T cell-mediated immune responses, e.g., activation, proliferation, increase in cytotoxic potential and IFN-γ responses were evaluated. CD4+ and CD8+ phenotyping showed that effector and central memory T cells were activated. Additionally, vaccine induced follicular T helper cell responses ($T_{FH}$) were also elicited.

In some embodiments, long-term cultures human precision-cut lung slices (PCLS) from human donors are used as an ex vivo model to evaluate immune response to stimulation by influenza vaccine. See e.g., Temann, A., et al., Hum Vac Immunother 13(2):351-358 (2017). Upon stimulation with influenza vaccines, PCLS showed upregulation of cytokine secretions, e.g., IFN-γ, TNF-α and IL-2.

In Vivo Models

Various animal models for evaluating influenza vaccines are known in the art. Margine, I., Krammer, F., Pathogens 3(4):845-874 (2014). Immunogenicity and protective efficacy of candidate influenza vaccines have been tested in e.g., chicken, mouse, ferret, pigs, and non-human primates models.

Ferrets were the first species to be successfully infected with human influenza isolates, and is susceptible to a wide range of human isolates without prior adaptation. Ferrets display clinical symptoms similar to human disease when infected with human influenza, although the presence and severity of symptoms vary depending on the challenge viral strain and route of administration.

Wild mice are not natural hosts of the influenza viruses. However, mice are widely used in influenza research due to their small size, low cost, availability of immunological reagents, availability of laboratory mice strains that can be infected with certain influenza, and availability of transgenic mice strains with targeted gene disruptions to study host responses. Generally, influenza viruses require adaption in mice to be able to infect mice and replicate. The process of adaptation, i.e., repeated in vivo passage in mouse lungs will cause antigenic and phenotypic changes in the adapted virus. However, several pathogenic pandemic influenza strains, such as H1N1, H5N1, and H7, are able to cause disease in mice without prior adaption.

Pigs are an attractive model for influenza research as they are naturally infected by both human and avian influenza viruses. Innate and adaptive B- and T-cell immunity against influenza have been characterized in the pig model. Holzer, B., et al., Front. Immunol. 10:98 (2019). doi: 10.3389/fimmu.2019.00098.

Immunogenicity and challenge influenza studies have been conducted in pigs. For example cold adapted 2017-2018 Northern Hemisphere LAIV vaccine Fluenz Tetra (AstraZeneca) containing two type A viruses: H1N1 A/Slovenia/2903/2015, MEDI 279432 107.0±0.5 FFU [A/Michigan/45/2015 (H1N1) pdm09-like strain]; H3N2 A/New Caledonia/71/2014, MEDI 263122 107.0±0.5 FFU [A/Hong Kong/4801/2014 (H3N2)-like strain] and two type B (IBV) viruses; (B/Brisbane/60/2008, MEDI 228030) 107.0±0.5

FFU (B/Brisbane/60/2008-like strain) and B/Phuket/3073/2013, MEDI 254977) 107.0±0.5 FFU (B/Phuket/3073/2013-like strain) were administered intranasally to pigs. Holzer, B., et al., *Front. Immunol* 10:2625 (2019). doi: 10.3389/fimmu.2019.02625. Four weeks after immunization, the pigs were challenged intranasally with wild-type viruses contained in the LAIV vaccine.

Nasal swabs were collected to test virus load. Serum and bronchoalveolar lavage (BAL) fluid were collected and tested for antibody and neutralizing antibody titers in ELISA and microneutralization (MN) assays, respectively. Cellular response were tested in IFN-γ ELISPOT and intracellular cytokine staining of cells collected from peripheral blood, trachea bronchial lymph nodes (TBLNs) and BALs.

Nonhuman primates are naturally infected by human influenza virus, and are considered good models of human responses to influenza infection and vaccination. Although ethical and economical considerations limit the use of nonhuman primates in influenza vaccine research, their use is challenge experiments are useful in testing pandemic influenza virus strains.

In some embodiments, the immunogenic compositions herein are tested in immunogenicity and/or challenge studies in animal models.

Immunogenic Compositions

Also provided herein are immunogenic compositions (e.g., vaccines) comprising combinations or cocktails of the recombinant viral proteins and/or polypeptides described herein. In some embodiments, the immunogenic compositions comprise a nucleic acid molecule encoding the recombinant viral proteins and/or polypeptides described herein. In some embodiments, the compositions further comprise a pharmaceutically acceptable carrier.

In some embodiments, immunogenic compositions described herein further comprise one or more adjuvants. For example, alum, aluminum salts (Baylor et al., 2002, Vaccine, 20:S18; incorporated herein by reference) and monophosphoryl lipid A (MPL; Ribi et al., 1986, Immunology and Immunopharmacology of Bacterial Endotoxins, Plenum Publ. Corp., NY, p. 407; incorporated herein by reference) can be used as adjuvants in human vaccines. Alternatively or additionally, new compounds are currently being tested as adjuvants in human vaccines, such as: MF59 (See, e.g., Ott et al., "MF59—Design and Evaluation of a Safe and Potent Adjuvant for Human Vaccines" in Vaccine Design: The Subunit and Adjuvant Approach (Powell, M. F. and Newman, M. J. eds.) Plenum Press, New York, 1995, pp. 277-296; incorporated herein by reference); CpG oligodeoxynudeotide (ODN) adjuvants such as CPG 7909 (Cooper et al., 2004, Vaccine, 22:3136; incorporated herein by reference); Monophosphoryl lipid A (MPL) adjuvants and lipid A mimetis including AS04 (Didierlaurent, A. M. et al, J. Immunol., 2009, 183: 6186-6197; incorporated by reference herein), monophosphoryl lipid A (MPL, GSK) and glucopyranosyl lipid A GLA (Immune Design Corporation, IDC); AF03 (Klucker, M. F. et al, J. Pharm Sci., 2012, 101: 4490-4500; incorporated herein by reference); the TLR-3 ligand polyinosinic:polycytidylic acid [poly(I:C)]; TLR9 adjuvants such as IC31 (Riedl, K. et al., Vaccine, 2008, 26: 3461-3468; incorporated herein by reference); imidazoquinolines (double cyclic organic molecules that act as TLR-7/8 agonists) such as imiquimod (R837) or resiquimod (R848); saponins such as QS21 (Ghochikyan et al., 2006, Vaccine, 24:2275; incorporated herein by reference), ISCOMATRIX adjuvant (Duewell, P., et al., J. Immunol, 2011, 187: 55-63; incorporated herein by reference), and Matrix-M™ (Novavax).

Additionally, some adjuvants are known in the art to enhance the immunogenicity of influenza vaccines, such as poly[di(carboxylatophenoxy)phosphazene] (PCCP; Payne et al., 1998, Vaccine, 16:92; incorporated herein by reference), interferon-.gamma. (Cao et al., 1992, Vaccine, 10:238; incorporated herein by reference), block copolymer P1205 (CRL1005; Katz et al., 2000, Vaccine, 18:2177; incorporated herein by reference), interleukin-2 (IL-2; Mbwuike et al., 1990, Vaccine, 8:347; incorporated herein by reference), and polymethyl methacrylate (PMMA; Kreuter et al., 1981, J. Pharm. Sci., 70:367; incorporated herein by reference).

In some embodiments, the immunogenic compositions include one or more inactive agents such as a sterile, biocompatible carrier including, but not limited to, sterile water, saline, buffered saline, or dextrose solution. In some embodiments, the composition contains any of a variety of additives, such as stabilizers, buffers, excipients (e.g., sugars, amino acids, etc.), or preservatives. Pharmaceutically acceptable carriers used in particular embodiments include, but are not limited to, saline, buffered saline, dextrose, water, glycerol, ethanol, and combinations thereof. In some embodiments, the carrier and composition are sterile, and the formulation suits the mode of administration. In some embodiments, an immunogenic composition contains minor amounts of wetting or emulsifying agents, or pH buffering agents. In some embodiments, a pharmaceutical composition is a liquid solution, suspension, emulsion, tablet, pill, capsule, sustained release formulation, or powder. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

In some embodiments, an immunogenic composition is formulated for intradermal injection, intranasal administration or intramuscular injection. In some embodiments, injectables are prepared in conventional forms, either as liquid solutions or suspensions, solid forms suitable for solution or suspension in liquid prior to injection, or as emulsions. In some embodiments, injection solutions and suspensions are prepared from sterile powders, granules, and. General considerations in the formulation and manufacture of pharmaceutical agents for administration by these routes may be found, for example, in Remington's Pharmaceutical Sciences, 19.sup.th ed., Mack Publishing Co., Easton, Pa., 1995; incorporated herein by reference. At present the oral or nasal spray or aerosol route (e.g., by inhalation) are most commonly used to deliver therapeutic agents directly to the lungs and respiratory system. In some embodiments, compositions in accordance with the invention are administered using a device that delivers a metered dosage of composition (e.g., of an optimized HA polypeptide). Suitable devices for use in delivering intradermal pharmaceutical compositions described herein include short needle devices such as those described in U.S. Pat. Nos. 4,886,499, 5,190,521, 5,328,483, 5,527,288, 4,270,537, 5,015,235, 5,141,496, 5,417,662 (all of which are incorporated herein by reference).

Intradermal compositions may also be administered by devices which limit the effective penetration length of a needle into the skin, such as those described in WO1999/34850, incorporated herein by reference, and functional equivalents thereof. Also suitable are jet injection devices which deliver liquid vaccines to the dermis via a liquid jet injector or via a needle which pierces the stratum corneum and produces a jet which reaches the dermis. Jet injection devices are described for example in U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO1997/37705, and WO1997/13537 (all of which are incorporated herein by reference). Also suitable are ballistic powder/particle delivery devices which use compressed gas to accelerate vaccine in powder form through the outer layers of the skin to the dermis. Additionally, conventional syringes may be used in the classical mantoux method of intradermal administration.

Preparations for parenteral administration include sterile aqueous or nonaqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

In some embodiments, the compositions are administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Methods of Use

In some embodiments, the polypeptides described herein are capable of eliciting an immune response against an influenza virus. In some embodiments, the polypeptides can be used as vaccines to protect individuals against influenza infection. In some embodiments, the nucleic acid molecules encoding polypeptides described herein are capable of eliciting an immune response against an influenza virus. In some embodiments, the nucleic acid molecules can be used as vaccines to protect individuals against influenza infection.

In some embodiments, the disclosure provides a method of vaccinating a subject against influenza, in particular, against various strains of influenza. Such methods employ the immunogenic compositions of the present disclosure. Accordingly, in some embodiments, the method comprises administering an immunogenic composition to a subject such that an immune response against influenza virus is produced in the subject. In some embodiments, the polypeptides described herein are capable of eliciting neutralizing antibodies to influenza. In some embodiments, the nucleic acid molecules encoding polypeptides described herein are capable of eliciting neutralizing antibodies to influenza.

Immunogenic compositions of the present disclosure can be used to vaccinate individuals using a prime/boost protocol. Such a protocol is described in U.S. Patent Publication No. 2011/0177122, which is incorporated herein by reference in its entirety. In such a protocol, a first immunogenic composition may be administered to the individual (prime) and then after a period of time, a second immunogenic composition may be administered to the individual (boost). Administration of the boosting composition is generally weeks or months after administration of the priming composition, preferably about 2-3 weeks or 4 weeks, or 8 weeks, or 16 weeks, or 20 weeks, or 24 weeks, or 28 weeks, or 32 weeks. In one embodiment, the boosting composition is formulated for administration about 1 week, or 2 weeks, or 3 weeks, or 4 weeks, or 5 weeks, or 6 weeks, or 7 weeks, or 8 weeks, or 9 weeks, or 16 weeks, or 20 weeks, or 24 weeks, or 28 weeks, or 32 weeks after administration of the priming composition.

In some embodiments, the subject is at risk for infection with influenza. In some embodiments, the subject has been exposed to influenza. For example, the subject may be an elderly individual, a child, an infant or an immunocompromised individual. As used herein, the terms exposed, exposure, and the like, indicate the subject has come in contact with a person or animal that is known to be infected with influenza. Immunogenic compositions of the present disclosure may be administered using techniques well known to those in the art and described herein.

In some embodiments, the polypeptides and immunogenic compositions of the present disclosure is used to protect a subject against infection by antigenically divergent influenza. In some embodiments, the nucleic acid molecules and immunogenic compositions of the present disclosure is used to protect a subject against infection by antigenically divergent influenza.

Methods of preparing and administering immunogenic compositions to a subject in need thereof are well known in the art or readily determined by those skilled in the art. The dosage and frequency of administration may depend on whether the treatment is prophylactic or therapeutic.

The immunogenic composition and polypeptides of the disclosure are suitable for administration to mammals (e.g., primates, (e.g., humans, chimpanzees, monkeys, baboons), rats (e.g., cotton rats), mice, cows (e.g., calves), guinea pigs, ferrets and hamsters). In some embodiments, the disclosure provides a method of inducing an immune response in a mammal, comprising the step of administering a composition (e.g., an immunogenic composition) of the disclosure to the mammal. The compositions (e.g., an immunogenic composition) can be used to produce a vaccine formulation for immunizing a mammal. The mammal is typically a human, and the immunogenic composition typically comprises a polypeptide comprising an amino acid sequence of an influenza viral protein. In some embodiments, the mammal is a human, and the immunogenic composition comprises a nucleic acid molecule encoding a polypeptide comprising an amino acid sequence of an influenza viral protein.

The disclosure also provides a composition of for use as a medicament, e.g., for use in immunizing a patient against influenza infection.

The disclosure also provides the use of a polypeptide as described above in the manufacture of a medicament for raising an immune response in a patient. In some embodiments, the disclosure provides the use of a nucleic acid molecule described herein in the manufacture of a medicament for raising an immune response in a patient.

The immune response raised by these methods and uses will generally include an antibody response, preferably a protective antibody response. Methods for assessing antibody responses after influenza vaccination are well known in the art.

Compositions of the invention can be administered in a number of suitable ways, such as intramuscular injection (e.g., into the arm or leg), subcutaneous injection, intranasal administration, oral administration, intradermal administration, transcutaneous administration, transdermal administration, and the like. The appropriate route of administration will be dependent upon the age, health and other characteristics of the mammal A clinician will be able to determine an appropriate route of administration based on these and other factors.

Immunogenic compositions, and vaccine formulations, may be used to treat both children and adults, including pregnant women. Thus a subject may be less than 1 year old, 1-5 years old, 5-15 years old, 15-55 years old, or at least 55 years old. Preferred subjects for receiving the vaccines are the elderly (e.g., >50 years old, >60 years old, >65 years, and preferably >75 years), the young (e.g., <6 years old, such as 4-6 years old, <5 years old), and pregnant women. The vaccines are not limited to these groups, however, and may be used more generally in a population.

Treatment can be by a single dose schedule or a multiple dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Administration of more than one dose (typically two doses) is particularly useful in immunologically naive patients. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, and the like.)

Vaccine formulations produced using a composition of the disclosure may be administered to patients at substantially the same time as (e.g., during the same medical consultation or visit to a healthcare professional or vaccination center) other vaccines.

In some embodiments, the immunogenic compositions, polypeptides or nucleic acid molecules described herein are administered as a therapeutic to a subject infected with influenza.

Kits

The immunogenic composition or polypeptide of the disclosure can be provided in a kit. In some embodiments, a nucleic acid molecule of the disclosure is provided in a kit. In some embodiments, the kit includes (a) a container that contains a composition that includes one or more unit doses of the immunogenic composition or polypeptide, and optionally (b) instructions for use. In some embodiments, the kit includes (a) a container that contains a composition that includes one or more unit doses of the immunogenic composition or nucleic acid molecule, and optionally (b) instructions for use. The unit doses of the immunogenic composition or polypeptide are sufficient to cause an immunogenic response (e.g., antibody production) in a subject. In some embodiments, the unit doses of the immunogenic composition or nucleic acid molecule are sufficient to cause an immunogenic response (e.g., antibody production) in a subject. The kit can also include reagents and instructions useful in the testing (assaying) for an immunogenic response. Such methods of assaying for an immunogenic response include, but are not limited to, any of the testing methods described herein. In one embodiment, the kit includes one or more additional agents for treating influenza. For example, the kit includes a first container that contains a composition that includes the immunogenic composition, and a second container that includes the one or more additional agents.

In some embodiments, the instructions provide methods of administering the immunogenic composition, e.g., in a suitable dose, dosage form, or mode of administration (e.g., a dose, dosage form, or mode of administration described herein), to treat a subject who is infected with influenza, or who is at risk of being infected with influenza.

In addition to the immunogenic composition or polypeptide, the composition in the kit can include other ingredients, such as a solvent or buffer, a stabilizer, or a preservative. The agent can be provided in any form, e.g., liquid, dried or lyophilized form, preferably substantially pure and/or sterile. When the agents are provided in a liquid solution, the liquid solution preferably is an aqueous solution. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the polypeptide and the second agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

Definitions

Terms used in the claims and specification are defined as set forth below unless otherwise specified.

It must be noted that, as used in the specification and the appended claims, the singular forms "a," "an" and "the" include plural referents unless the context clearly dictates otherwise. Further, unless otherwise required by context, singular terms shall include pluralities and plural terms shall include the singular.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

As used herein, the term "alanine scanning" refers to a technique used to determine the contribution of a specific wild-type residue to the stability or function(s) (e.g., binding affinity) of a given protein or polypeptide. The technique involves the substitution of an alanine residue for a wild-type residue in a polypeptide, followed by an assessment of the stability or function(s) (e.g., binding affinity) of the alanine-substituted derivative or mutant polypeptide and comparison to the wild-type polypeptide. Techniques to substitute alanine for a wild-type residue in a polypeptide are known in the art.

The term "ameliorating" refers to any therapeutically beneficial result in the treatment of a disease state, e.g., infection, lessening in the severity or progression, remission, or cure thereof.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

As used herein, an "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions," can also be made, e.g., insertion of about three to about five or even up to about ten, fifteen, or twenty amino acid residues. The inserted residue(s) can be naturally occurring or non-naturally occurring as disclosed above. An "amino acid deletion" refers to the removal of at least one amino acid residue from a predetermined amino acid sequence. The following table provides exemplary and preferred substitutions for all 20 amino acids.

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |

-continued

| Original Residues | Exemplary Substitutions | Preferred Substitutions |
|---|---|---|
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, met, Leu, Phe, Ala, norleucine | Leu |

The term "antigen presenting cell" or "APC" is a cell that displays foreign antigen complexed with MHC on its surface. T cells recognize this complex using T cell receptor (TCR). Examples of APCs include, but are not limited to, dendritic cells (DCs), peripheral blood mononuclear cells (PBMC), monocytes (such as THP-1), B lymphoblastoid cells (such as C1R.A2, 1518 B-LCL) and monocyte-derived dendritic cells (DCs). Some APCs internalize antigens either by phagocytosis or by receptor-mediated endocytosis.

The term "antigen presentation" refers to the process by which APCs capture antigens and enables their recognition by T cells, e.g., as a component of an MHC-I and/or MHC-II conjugate.

As used herein, the term "base pair" refers to two nucleobases on opposite complementary nucleic acid strands that interact via the formation of specific hydrogen bonds. As used herein, the term "Watson-Crick base pairing", used interchangeably with "complementary base pairing", refers to a set of base pairing rules, wherein a purine always binds with a pyrimidine such that the nucleobase adenine (A) forms a complementary base pair with thymine (T) and guanine (G) forms a complementary base pair with cytosine (C) in DNA molecules. In RNA molecules, thymine is replaced by uracil (U), which, similar to thymine (T), forms a complementary base pair with adenine (A). The complementary base pairs are bound together by hydrogen bonds and the number of hydrogen bonds differs between base pairs. As in known in the art, guanine (G)-cytosine (C) base pairs are bound by three (3) hydrogen bonds and adenine (A)-thymine (T) or uracil (U) base pairs are bound by two (2) hydrogen bonds. Base pairing interactions that do not follow these rules can occur in natural, non-natural, and synthetic nucleic acids and are referred to herein as "non-Watson-Crick base pairing" or alternatively "non-complementary base pairing".

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence. Polypeptides derived from another peptide can have one or more mutations relative to the starting polypeptide, e.g., one or more amino acid residues which have been substituted with another amino acid residue or which has one or more amino acid residue insertions or deletions.

A polypeptide can comprise an amino acid sequence which is not naturally occurring. Such variants necessarily have less than 100% sequence identity or similarity with the starting molecule. In certain embodiments, the variant has an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

In some embodiments, there is one amino acid difference between a starting polypeptide sequence and the sequence derived there from. Identity or similarity with respect to this sequence is defined herein as the percentage of amino acid residues in the candidate sequence that are identical (i.e., same residue) with the starting amino acid residues, after aligning the sequences and introducing gaps, if necessary, to achieve the maximum percent sequence identity. In certain embodiments, a polypeptide consists of, consists essentially of, or comprises an amino acid sequence selected from a sequence set forth in the sequence listing table. In certain embodiments, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence selected from a sequence set forth in the sequence listing table. In certain embodiments, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence selected from a sequence set forth in the sequence listing table. In certain embodiments, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence selected from a sequence set forth in the sequence listing table.

In certain embodiments, the polypeptides of the disclosure are encoded by a nucleotide sequence. Nucleotide sequences of the disclosure can be useful for a number of applications, including: cloning, gene therapy, protein expression and purification, mutation introduction, DNA vaccination of a host in need thereof, antibody generation for, e.g., passive immunization, PCR, primer and probe generation, and the like. In certain embodiments, the nucleotide sequence of the invention comprises, consists of, or consists essentially of, a nucleotide sequence selected from a sequence set forth in the sequence listing table. In certain embodiments, a nucleotide sequence includes a nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence selected from a sequence set forth in the sequence listing table. In certain embodiments, a nucleotide sequence includes a contiguous nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous nucleotide sequence selected from a sequence set forth in the sequence listing table. In certain embodiments, a nucleotide sequence includes a nucleotide sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous nucleotides of a nucleotide sequence selected from a sequence set forth in the sequence listing table.

It will also be understood by one of ordinary skill in the art that the polypeptides suitable for use in the compositions and methods disclosed herein can be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues can be made. Mutations can be introduced by standard techniques, such as site-directed mutagenesis and PCR-mediated mutagenesis.

The polypeptides suitable for use in the compositions and methods disclosed herein can, in some embodiments, comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a polypeptide is preferably replaced with another amino acid residue from the same side chain family. In some embodiments, a string of amino acids can be replaced with a structurally similar string that differs in order and/or composition of side chain family members. Alternatively, in some embodiments, mutations can be introduced randomly along all or part of a coding sequence, such as by saturation mutagenesis, and the resultant mutants can be incorporated into polypeptides of the disclosure and screened for their ability to induce an immune response.

As used herein, the term antigen "cross-presentation" refers to presentation of exogenous protein antigens to T cells via MEW class I and class II molecules on APCs.

As used herein, the term "cytotoxic T lymphocyte (CTL) response" refers to an immune response induced by cytotoxic T cells. CTL responses are mediated primarily by $CD8^+$ T cells.

As used herein, the term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

As used herein, the term "epitope" or "antigenic determinant" refers to a determinant or site on an antigen (e.g., hemagglutinin) to which an antigen-binding protein (e.g., an immunoglobulin, antibody, or antigen-binding fragment) specifically binds. The epitopes of protein antigens can be demarcated into "linear epitopes" and "conformational epitopes". As used herein, the term "linear epitope" refers to an epitope formed from a contiguous, linear sequence of linked amino acids. Linear epitopes of protein antigens are typically retained upon exposure to chemical denaturants (e.g., acids, bases, solvents, cross-linking reagents, chaotropic agents, disulfide bond reducing agents) or physical denaturants (e.g. thermal heat, radioactivity, or mechanical shear or stress). In some embodiments, an epitope is non-linear, also referred to as an interrupted epitope. As used herein, the term "conformational epitope" or "non-linear epitope" refers to an epitope formed from noncontiguous amino acids juxtaposed by tertiary folding of a polypeptide. Conformational epitopes are typically lost upon treatment with denaturants. An epitope typically includes at least 3, 4, 5, 6, 7, 8, 9, 10, 11, 12, 13, 14 or 15 amino acids in a unique spatial conformation. In some embodiments, an epitope includes fewer than 25, 24, 23, 22, 21, 20, 19, 18, 17, 16, 15, 14, 13, 12, 11, 10, 9, 8, 7, 6 or 5 amino acids in a unique spatial conformation. An epitope that is recognized by a T cell receptor is generally referred to as a T-cell epitope. An epitope that is recognized by an antibody or a B cell receptor is generally referred to as a B-cell epitope. Generally, an antibody, or antigen-binding fragment thereof, specific for a particular target molecule will preferentially recognize and bind to a specific epitope on the target molecule within a complex mixture of proteins and/or macromolecules. As used herein, the T and/or B cell epitopes comprises conserved amino acid residues, hypervariable amino acid residues, or combinations thereof of a viral protein. In other embodiments, the T and/or B cell epitopes comprises conserved amino acid residues of the viral proteins.

As used herein, the term "epitope mapping" refers to a process or method of identifying the binding site, or epitope, of an antibody, or antigen-binding fragment thereof, on its target protein antigen. Epitope mapping methods and techniques are provided herein.

As used herein, the term "fragment" in the context of an amino acid sequence refers to an amino acid sequence comprising a portion of consecutive amino acid residues from a parent sequence. In a specific embodiment, the term refers to an amino acid sequence of 8 to 15, 10 to 20, 2 to 30, 5 to 30, 10 to 60, 25 to 100, 150 to 300 or more consecutive amino acid residues from a parent sequence. In another embodiment, the term refers to an amino acid sequence of at least 5, 10, 15, 20, 25, 30, 35, 40, 45, 50, 55, 60, 65, 70, 75, 80, 85, 90, 95, 100, 110, 125, 150, 175, or 200 consecutive amino acid residues of a parent sequence.

As used herein, the term "hemagglutinin protein" (or "HA protein') refers to a protein or polypeptide whose amino acid sequence includes at least one characteristic sequence of an influenza type A or B HA. A wide variety of HA sequences from influenza isolates are known in the art; indeed, the National Center for Biotechnology Information (NCBI) maintains a database (http://www.ncbi.nlm.nih.gov/genomes/FLU/) that, as of the filing of the present application includes approximately 40,000 HA sequences (for type A and B viruses). Those of ordinary skill in the art, referring to this database, can readily identify sequences that are characteristic of HA polypeptides generally, and/or of particular HA polypeptides (e.g., H1, H2, H3, H4, H5, H6, H7, H8, H9, H10, H11, H12, H13, H14, H15, or H16 polypeptides; or of HAs that mediate infection of particular hosts, e.g., human, avian, seal etc.). For example, in some embodiments, an HA polypeptide includes one or more characteristic sequence elements found between about residues 97 and about 185, about 324 and about 340, about 96 and about 100, and/or about 130 and about 230 of an HA protein found in a natural isolate of an influenza virus.

As used herein, "conserved" or "highly conserved regions" are influenza virus sequences from different strains, or consensus sequences, which have been employed to provide an antigen with broad protective properties. Sequence alignments are relied on to yield a "consensus" sequence, where many genetic sequences are incorporated into a single sequence. A consensus sequence may thus minimize the genetic distance between vaccine strains and viruses and so may elicit more cross-reactive immune responses than an immunogen derived from any single influenza virus.

As used herein, the term "hybridization" refers to the process of a first single-stranded nucleic acid, or a portion, fragment, or region thereof, annealing to a second single-stranded nucleic acid, or a portion, fragment, or region thereof, either from the same or separate nucleic acid molecules, mediated by Watson-Crick base pairing to form a secondary and/or tertiary structure. Complementary strands of linked nucleobases able to undergo hybridization can be from either the same or separate nucleic acids. Due to the thermodynamically favorable hydrogen bonding interaction between complementary base pairs, hybridization is a fundamental property of complementary nucleic acid sequences. Such hybridization of nucleic acids, or a portion or fragment thereof, may occur with "near" or "substantial" complementarity, as well as with exact complementarity.

As used herein, the term "hypervariable" refers to amino acid residues and/or protein regions that are abundant and surface exposed, and is a primary target of the immune response against the standard influenza vaccine. The immune response to influenza is overwhelmingly driven against the hypervariable regions of the virus. Thus, in traditional influenza vaccination or natural infections, the protective immune response is overwhelmingly directed at a limited number of continuously evolving, strain-specific, primary antigenic determinants on the surface of the influenza proteins, and there is minimal cross reaction with or protection against other serotypes of influenza.

As used herein, the term "non-hypervariable" or "hypervariable-substitute" refers to an amino acid residue that is substituted for a hypervariable amino acid residue, wherein the substitution eliminates or substantially reduces a strain-specific immune response (e.g., antibody response) against the region containing the hypervariable amino acid residue. In some embodiments, the non-hypervariable residue is one that when substituted for the hypervariable amino acid residue, provides surface epitope with reduced antigenicity. In some embodiments, the non-hypervariable residue is selected from is a nonpolar, aliphatic R group amino acid, e.g., alanine, glycine, valine, leucine, isoleucine, and methionine. In some embodiments, the non-hypervariable residue is conserved at the same position in a plurality of influenza strains.

As used herein, the term "immune response" refers to a response of a cell of the immune system, such as a B cell, T cell, dendritic cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate and/or adaptive immune response. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

The terms "inducing an immune response" and "enhancing an immune response" are used interchangeably and refer to the stimulation of an immune response (i.e., either passive or adaptive) to a particular antigen. The term "induce" as used with respect to inducing CDC or ADCC refer to the stimulation of particular direct cell killing mechanisms.

As used herein, the term "influenza strains" is based upon, e.g., the ability of influenza to agglutinate red blood cells (RBCS or erythrocytes). Influenza strains are typically categorized based upon their immunologic or antigenic profile. An HA1 titer is typically defined as the highest dilution of a serum that completely inhibits hemagglutination. See, e.g., Schild, et al., Bull. Wld Hlth Org., 1973, 48:269-278, etc. Those of skill in the art will be quite familiar with categorization and classification of influenza into strains and the methods to do so. Antibodies specific for particular influenza strains can bind to the virus and, thus, prevent such agglutination. Assays determining strain types based on such inhibition are typically known as hemagglutinin inhibition assays (HI assays or HA1 assays) and are standard and well known methods in the art to characterize influenza strains. Of course, those of skill in the art will be familiar with other assays, e.g., ELISA, indirect fluorescent antibody assays, immunohistochemistry, Western blot assays, etc. with which to characterize influenza strains and the use of and discussion herein of HI assays should not be necessarily construed as limiting.

As used herein "influenza types and subtypes" are influenza A and B virus typically associated with influenza outbreaks in human populations. The type A viruses are categorized into subtypes based upon differences within their hemagglutinin and neuraminidase surface glycoprotein antigens. Hemagglutinin in type A viruses has 14 known subtypes and neuraminidase has 9 known subtypes. In humans, currently only about 3 different hemagglutinin and 2 different neuraminidase subtypes are known, e.g., H1, H2, H3, N1, and N2. In particular, two major subtypes of influenza A have been active in humans, namely, H1N1 and H3N2. H1N2, however has recently been of concern.

As used herein, the term "influenza vaccine" refers to an immunogenic composition capable of stimulating an immune response, administered for the prevention, amelioration, or treatment of influenza virus infection. An influenza vaccine may include, for example, attenuated or killed influenza virus, virus-like particles (VLPs) and/or antigenic polypeptides (e.g., the engineered hemagglutinins described herein) or DNA derived from them, or any recombinant versions of such immunogenic materials.

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with an immunogenic composition).

The term "in vivo" refers to processes that occur in a living organism.

As used herein, "immunogenic composition" refers to a composition that comprises at least one antigen which elicits an immunological response in the host to which the immunogenic composition is administered. Such immunological responses can be a cellular and/or antibody-mediated immune response to the immunogenic composition.

As used herein, the terms "linked," "operably linked," "fused", or "fusion", are used interchangeably. These terms refer to the joining together of two more elements or components or domains, by whatever means including chemical conjugation or recombinant means. Methods of chemical conjugation (e.g., using heterobifunctional cross-linking agents) are known in the art.

As used herein, "MHC molecules" refers to two types of molecules, MHC class I and MHC class II. MHC class I molecules present antigen to specific CD8+ T cells and MHC class II molecules present antigen to specific CD4+ T cells. Antigens delivered exogenously to APCs are processed primarily for association with MHC class II. In contrast, antigens delivered endogenously to APCs are processed primarily for association with MHC class I.

As used herein, the terms "NA" and "neuraminidase" refer to any influenza neuraminidase, such as an influenza A neuraminidase, an influenza B neuraminidase, or an influenza C neuraminidase. A typical neuraminidase comprises domains known to those of skill in the art including a cytoplasmic domain, a transmembrane domain, a stalk domain, and a globular head domain. As used herein, the terms "neuraminidase" and "NA" encompass neuraminidase polypeptides that are modified by post-translational processing such as disulfide bond formation, glycosylation (e.g., N-linked glycosylation), As used herein, the term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "nucleic acid" is used in its broadest sense and encompasses any compound and/or substance that includes a polymer of nucleotides. These polymers are often referred to as polynucleotides. Exemplary nucleic acids or polynucleotides of the disclosure include, but are not limited to, ribonucleic acids (RNAs), deoxyribonucleic acids (DNAs), DNA-RNA hybrids, RNAi-inducing agents, RNAi agents, siRNAs, shRNAs, miRNAs, antisense RNAs, ribozymes, catalytic DNA, RNAs that induce triple helix formation, threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, the term "nucleoside" refers to a compound containing a sugar molecule (e.g., a ribose in RNA or a deoxyribose in DNA), or derivative or analog thereof, covalently linked to a nucleobase (e.g., a purine or pyrimidine), or a derivative or analog thereof (also referred to herein as "nucleobase"), but lacking an internucleoside linking group (e.g., a phosphate group). As used herein, the term "nucleotide" refers to a nucleoside covalently bonded to an internucleoside linking group (e.g., a phosphate group), or any derivative, analog, or modification thereof that confers improved chemical and/or functional properties (e.g., binding affinity, nuclease resistance, chemical stability) to a nucleic acid or a portion or segment thereof.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

As used herein, "parenteral administration," "administered parenterally," and other grammatically equivalent phrases, refer to modes of administration other than enteral and topical administration, usually by injection, and include, without limitation, intravenous, intranasal, intraocular, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

As used herein, the term "patient" includes human and other mammalian subjects that receive either prophylactic or therapeutic treatment.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra). In some embodiments, alignment of sequences is conducted by the Dawn method (Ricke, D. O. & Shcherbina, A. 2015 *IEEE High Performance Extreme Computing Conference* (*HPEC*), doi:10.1109.HPEC.2015.7322463 (2015)).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

As used herein, the terms "polypeptide," "peptide", and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, the term "preventing" when used in relation to a condition, refers to administration of a composition which reduces the frequency of, or delays the onset of, symptoms of a medical condition in a subject relative to a subject which does not receive the composition.

As used herein, the term "purified" or "isolated" as applied to any of the proteins described herein refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

As used herein, the term "recombinant influenza vaccine" refers to influenza-specific immunogenic composition comprising one or more of engineered influenza viral proteins described herein (e.g., hemaglutinin, neuraminidase), including, but not limited to whole influenza virus, subunit preparations thereof, virus-like particles, recombinant protein (i.e., preparations composed of recombinant HA purified to varying degree), and DNA- and viral vector-based vaccines. Recombinant influenza vaccines as described herein may optionally contain one or more adjuvants.

As used herein, the term "subject" includes any human or non-human animal. For example, the methods and compositions of the present invention can be used to treat a subject with an immune disorder. The term "non-human animal" includes all vertebrates, e.g., mammals and non-mammals, such as non-human primates, sheep, dog, cow, chickens, amphibians, reptiles, etc.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See www.ncbi.nlm.nih.gov.

The term "T cell" refers to a type of white blood cell that can be distinguished from other white blood cells by the presence of a T cell receptor on the cell surface. There are several subsets of T cells, including, but not limited to, T helper cells (a.k.a. $T_H$ cells or $CD4^+$ T cells) and subtypes, including $T_H1$, $T_H2$, $T_H3$, $T_H17$, $T_H9$, and $T_{FH}$ cells, cytotoxic T cells (i.e., Tc cells, $CD8^+$ T cells, cytotoxic T lymphocytes, T-killer cells, killer T cells), memory T cells and subtypes, including central memory T cells ($T_{CM}$ cells), effector memory T cells ($T_{EM}$ and $T_{EMRA}$ cells), and resident memory T cells ($T_{RM}$ cells), regulatory T cells (a.k.a. $T_{reg}$ cells or suppressor T cells) and subtypes, including $CD4^+$ $FOXP3^+$ $T_{reg}$ cells, $CD4^+$ $FOXP3^-$ $T_{reg}$ cells, Tr1 cells, Th3 cells, and $T_{reg}17$ cells, natural killer T cells (a.k.a. NKT cells), mucosal associated invariant T cells (MAITs), and gamma delta T cells (γδ T cells), including Vγ9/Vδ2 T cells. Any one or more of the aforementioned or unmentioned T cells may be the target cell type for a method of use of the invention.

As used herein, the terms "T cell activation" or "activation of T cells" refers to a cellular process in which mature T cells, which express antigen-specific T cell receptors on their surfaces, recognize their cognate antigens and respond by entering the cell cycle, secreting cytokines or lytic enzymes, and initiating or becoming competent to perform cell-based effector functions. T cell activation requires at least two signals to become fully activated. The first occurs after engagement of the T cell antigen-specific receptor (TCR) by the antigen-major histocompatibility complex (MEW), and the second by subsequent engagement of co-stimulatory molecules (e.g., CD28). These signals are transmitted to the nucleus and result in clonal expansion of T cells, upregulation of activation markers on the cell surface, differentiation into effector cells, induction of cytotoxicity or cytokine secretion, induction of apoptosis, or a combination thereof.

As used herein, the term "T cell-mediated response" refers to any response mediated by T cells, including, but not limited to, effector T cells (e.g., $CD8^+$ cells) and helper T cells (e.g., $CD4^+$ cells). T cell mediated responses include, for example, T cell cytotoxicity and proliferation.

As used herein, the terms "therapeutically effective amount" or "therapeutically effective dose," or similar terms used herein are intended to mean an amount of an agent (e.g., a nucleic acid molecule) that will elicit the desired biological or medical response (e.g., an improvement in one or more symptoms of an infection).

The terms "treat," "treating," and "treatment," as used herein, refer to therapeutic or preventative measures described herein. The methods of "treatment" employ administration to a subject, in need of such treatment, a human antibody of the present disclosure, for example, a subject in need of an enhanced immune response against a particular antigen or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

As used herein, the term "vaccination" refers to the administration of an immunogenic composition intended to generate an immune response, for example to a disease-causing agent such as influenza. Vaccination can be administered before, during, and/or after exposure to a disease-causing agent, and/or to the development of one or more symptoms, and in some embodiments, before, during, and/or shortly after exposure to the agent. Vaccines may elicit both prophylactic (preventative) and therapeutic responses. Methods of administration vary according to the vaccine, but may include inoculation, ingestion, inhalation or other forms of administration. Inoculations can be delivered by any of a number of routes, including parenteral, such as intravenous, subcutaneous or intramuscular. Vaccines may be administered with an adjuvant to boost the immune response. In some embodiments, vaccination includes multiple administrations, appropriately spaced in time, of an immunogenic composition.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

EXAMPLES

Example 1: Identification of Residues in H1N1

To identify highly conserved amino acid residues between strains of a particular type and/or subtype of influenza virus, amino acid sequences were obtained and aligned. Specifically, the Dawn method, described in Ricke, D. O & Shcherbina, A., *IEEE High Performance Extreme Computing Conference* (*HPEC*), doi:1031109/HPEC.2015.7322463 (2015), herein incorporated by reference, was used to align 52,443 influenza A H1N1 hemagglutinin amino acid sequences and 51,784 influenza A H1N1 neuraminidase amino acid sequences. FIG. 1 shows an alignment of a section of amino acid residues in the H1N1 HA protein from strains in years 2009-2019.

SEQ ID NO: 1 provides the amino acid sequence for hemagglutinin from the A/Michigan/45/2015 H1N1 strain. SEQ ID NO: 2 provides the amino acid sequence for neuraminidase from the A/Michigan/45/2015 strain H1N1 strain.

Highly variable residues were identified for both proteins, along with residues having low variability. The following sequence for hemagglutinin indicates hypervariable residues in bold and conserved regions are underlined.

(SEQ ID NO: 1)

MKAILVVLLYTFTTANADTLCIGYHANNSTDT

VDTVLEKNVTVTHSVNLLEDKHNGKLCKLRGV

APLHLGKCNIAGWILGNPECESLSTASSWSYI

VETSNSDNGTCYPGDFINYEELREQLSSVSSF

ERFEIFPKTSSWPNHDSNKGVTAACPHAGAKS

FYKNLIWLVKKGNSYPKLNQSYINDKGKEVLV

LWGIHHPSTTADQQSLYQNADAYVFVGTSRYS

KKFKPEIATRPKVRDQEGRMNYYWTLVEPGDK

ITFEATGNLVVPRYAFTMERNAGSGIIISDTP

VHDCNTTCQTPEGAINTSLPFQNIHPITIGKC

PKYVKSTKLRLATGLRNVPSIQSRGLFGAIAG

FIEGGWTGMVDGWYGYHHQNEQGSGYAADLKS

TQNAIDKITNKVNSVIEKMNTQFTAVGKEFNH

LEKRIENLNKKVDDGFLDIWTYNAELLVLLEN

ERTLDYHDSNVKNLYEKVRNQLKNNAKEIGNG

CFEFYHKCDNTCMESVKNGTYDYPKYSEEAKL

NREKIDGVKLESTRIYQILAIYSTVASSLVLV

VSLGAISFWMCSNGSLQCRICI

FIG. 2 provides the amino acid sequence and nucleic acid sequences for the H1N1 hemagglutinin protein with the nucleic acid sequences underlined for highly conserved regions and shown by boxes for the hypervariable amino acid residues.

The following sequence for neuraminidase indicates hypervariable residues in bold and conserved regions are underlined.

(SEQ ID NO: 2)

MNPNQKIITIGSICMTIGMANLILQIGNIISI

WVSHSIQIGNQSQIETCNQSVITYENNTWVNQ

TYVNISNINFAAGQSVVSVKLAGNSSLCPVSG

WAIYSKDNSVRIGSKGDVFVIREPFISCSPLE

CRTFFLTQGALLNDKHSNGTIKDRSPYRTLMS

CPIGEVPSPYNSRFESVAWSASACHDGINWLT

IGISGPDSGAVAVLKYNGIITDTIKSWRNNIL

RTQESECACVNGSCFTIMIDGPSDGQASYKIF

RIEKGKIIKSVEMKAPNYHYEECSCYPDSSEI

TCVCRDNWHGSNRPWVSFNQNLEYQMGYICSG

VTGDNPRPNDKTGSCGPVSSNGANGVKGFSFK

YGNGVWIGRTKSISSRKGFEMIWDPNGWTGTD

NKFSIKQDIVGINEWSGYSGSFVQHPELTGLD

CIRPCFWVELIRGRPEENTIWTSGSSISFCGV

NSDTVGWSWPDGAELPFTIDK

Example 2: Identification of Residues in H3N2

Using the same method described in Example 1, hypervariable amino acid residues and highly conserved regions were identified in the hemagglutinin and neuraminidase proteins of H3N2. Specifically, 42,653 hemagglutinin amino acid sequences and 29,491 neuraminidase amino acid sequences were aligned using the Dawn method.

SEQ ID NO: 3 provides the amino acid sequence for hemagglutinin from the A/Mississippi/27/2013 H3N2 strain. SEQ ID NO: 4 provides the amino acid sequence for neuraminidase from the Neuraminidase A/Miyagi/N1289/2005 H3N2 strain.

Highly variable residues were identified for both proteins, along with residues having low variability. The following sequence for hemagglutinin indicates hypervariable residues in bold and conserved regions are underlined.

(SEQ ID NO: 3)

MKTIIALSYILCLVFAQKLPPYGNSTATLCLG

HHALPNGTIVKTITNDRIEVTNATELVQNSSI

GEICDSPHQILDGENCTLIDALLGDPQCDGFQ

NKKWDLFVERSKAYSNCYPYDVPDYASLRSLV

ASSGTLEFNNESFNWTGVTQNGTSSACIRRSN

SSFFSRLNWLTHLNFKYPAINVIMPNNEQFDK

LYIWGVHHPGTDKDQIFLYAQSSGRITVSTKR

-continued

```
SQQAVIPNIGSRPRIRNIPSRISIYWTIVKPG
DILLINSTGNLIAPRGYFKIRSGKSSIMRSDA
PIGKCKSECITPNGSIPNDKPFQNVNRITYGA
CPRYVKQSTLKLATGMRNVPEKQTRGIFGAIA
GFIENGWEGMVDGWYGFRHQNSEGRGQAADLK
STQAAIDQINGKLNRLIGKTNEKFHQIEKEFS
EVEGRIQDLEKYVEDTKIDLWSYNAELLVALE
NQHTIDLTDSEMNKLFEKTKKQLRENAEDMGN
GCFKIYHKCDNACIGSIRNGTYDHNVYRDEAL
NNRFQIKGVELKSGYKDWILWISFAISCFLLC
VAIKGFIMWACQKGNIRCNIRCNICI
```

The following sequence for neuraminidase indicates hypervariable residues in bold and conserved regions are underlined.

(SEQ ID NO: 4)

```
MNPNQKIITIGSVSLTISTICFFMQIAILITT
VTLHFKQYEFNSPPNNQVMLCEPTIIERNITE
IVYLTNTTIEKEICPKLAEYRKWSKPQCNITG
FAPFSKDNSIRLSAGGDIWVTREPYVSCDPDK
CYQFALGQGTTLNNVHSNDIVRDRTPYRTLLM
NELGVPFHLGTKQVCIAWSSSSCHDGKAWLHV
CVTGDDKNATASFIYNGRLVDSIVSWSKEILR
TQESECVCINGTCTVVMTDGSASGKADTKILF
IEEGKIVHTSTLSGSAQHVEECSCYPRYPGVR
CVCRDNWKGSNRPIVDINIKDYSIVSSYVCSG
LVGDTPRKNDSSSSSHCLDPNNEEGGHGVKGW
AFDDGNDVWMGRTISEKLRSGYETFXVIEGWS
NPNSKLQINRQVIVDRGNRSGYSGIFSVEGKS
CINRCFYVELIRGRKEETEVLWTSNSIVVFCG
TSGTYGTGSWPDGADINLMPI
```

Example 3: Identification of Residues in Influenza B

Using the same method described in Example 1, hypervariable amino acid residues and highly conserved regions were identified in the hemagglutinin and neuraminidase proteins of influenza B. Specifically, 20,906 hemagglutinin amino acid sequences and 14,546 neuraminidase amino acid sequences were aligned using the Dawn method.

SEQ ID NO: 5 provides the amino acid sequence for hemagglutinin from the B/Brisbane/60/2008 influenza B strain. SEQ ID NO: 6 provides the amino acid sequence for neuraminidase from the B/Wisconsin/05/2016 influenza B strain.

Highly variable residues were identified for both proteins, along with residues having low variability. The following sequence for hemagglutinin indicates hypervariable residues in bold and conserved regions are underlined.

(SEQ ID NO: 5)

```
MKAIIVLLMVVTSNADRICTGITSSNSPHVVK
TATQGEVNVTGVIPLTTTPTKSHFANLKGTET
RGKLCPKCLNCTDLDVALGRPKCTGKIPSARV
SILHEVRPVTSGCFPIMHDRTKIRQLPNLLRG
YEHIRLSTHNVINAENAPGGPYKIGTSGSCPN
ITNGNGFFATMAWAVPKNDKNKTATNPLTIEV
PYICTEGEDQITVWGFHSDDETQMAKLYGDSK
PQKFTSSANGVTTHYVSQIGGFPNQTEDGGLP
QSGRIVVDYMVQKSGKTGTITYQRGILLPQKV
WCASGRSKVIKGSLPLIGEADCLHEKYGGLNK
SKPYYTGEHAKAIGNCPIWVKTPLKLANGTKY
RPPAKLLKERGFFGAIAGFLEGGWEGMIAGWH
GYTSHGAHGVAVAADLKSTQEAINKITKNLNS
LSELEVKNLQRLSGAMDELHNEILELDEKVDD
LRADTISSQIELAVLLSNEGIINSEDEHLLAL
ERKLKKMLGPSAVEIGNGCFETKHKCNQTCLD
RIAAGTFDAGEFSLPTFDSLNITAASLNDDGL
DNHTILLYYSTAASSLAVTLMIAIFVVYMVSR
DNVSCSICL
```

The following sequence for neuraminidase indicates hypervariable residues in bold and conserved regions are underlined.

(SEQ ID NO: 6)

```
MLPSTIQTLTLFLTSGGVLLSLYVSASLSYLL
YSDILLKFSPTEITAPTMPLDCANASNVQAVN
RSATKGVTLLLLPEPEWTYPRLSCPGSTFQKA
LLISPHRFGETKGNSAPLIIREPFVACGPNEC
KHFALTHYAAQPGGYYNGTRGDRNKLRHLISV
KLGKIPTVENSIFHMAAWSGSACHDGKEWTYI
GVDGPDNNALLKVKYGEAYTDTYHSYANNILR
TQESACNCIGGNCYLMITDGSASGVSECRFLK
IREGRIIKEIFPTGRVKHTEECTCGFASNKTI
ECACRDNRYTAKRPFVKLNVETDTAEIRLMCT
DTYLDTPRPNDGSITGPCESDGDKGSGGIKGG
FVHQRMKSKIGRWYSRTMSKTERMGMGLYVKY
GGDPWADSDALAFSGVMVSMKEPGWYSFGFEI
KDKKCDVPCIGIEMVHDGGKETWHSAATAIYC
LMGSGQLLWDTVTGVDMAL
```

Example 4: Production of B Cell Immune Response

Figure 3:
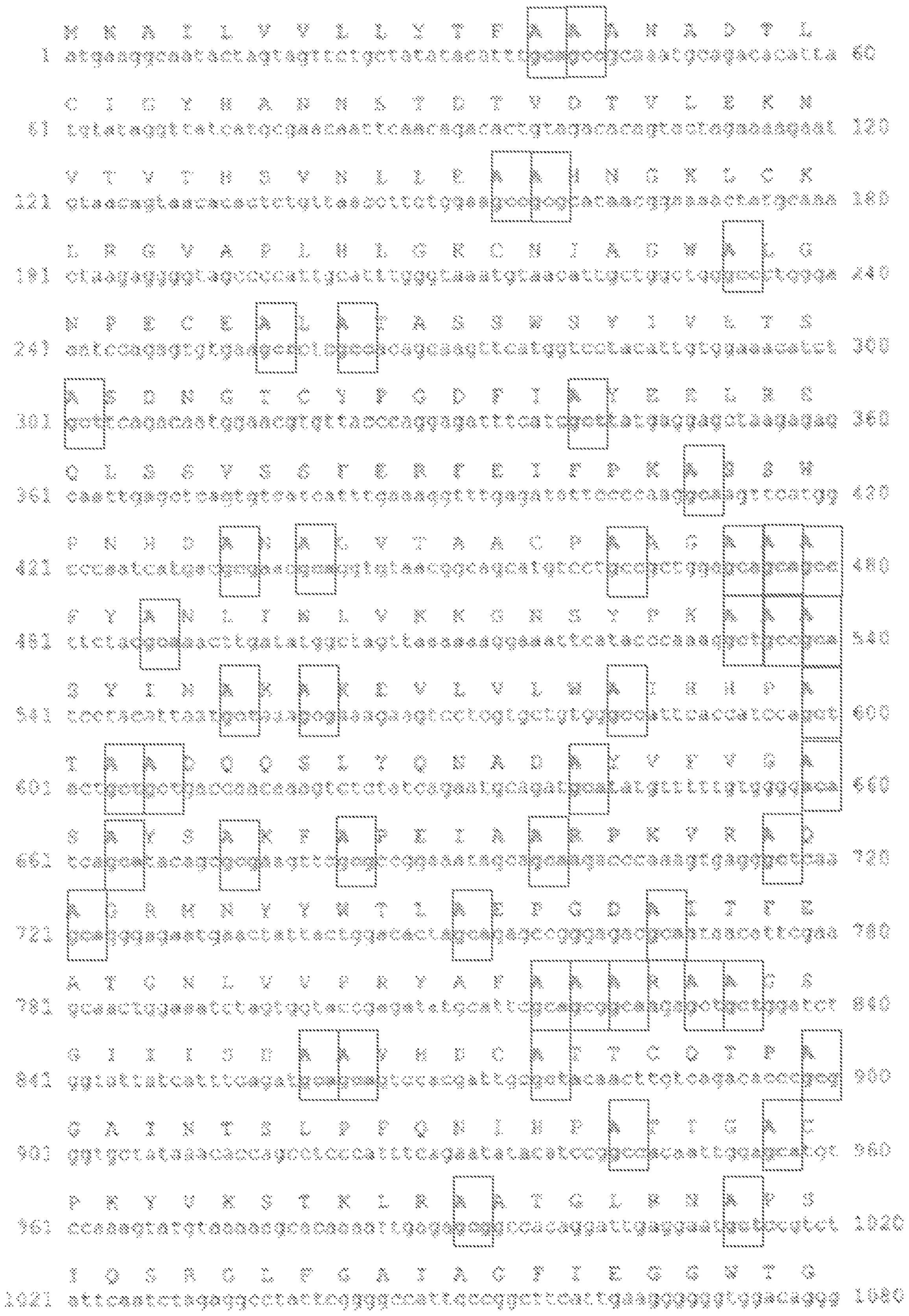
FIG. 3 provides the amino acid sequence (SEQ ID NO: 157) and nucleic acid sequence (SEQ ID NO: 170) of influenza A hemagglutinin where hypervariable residues have been replaced with alanine (shown using a box).

To determine whether the hypervariable residues identified in HA and NA proteins as described in Examples 1-3, alanine scanning of each residue and combinations of residues is performed. FIG. 3 shows an exemplary sequence wherein each hypervariable residue identified in the H1N1 HA protein described in Example 1 is replaced with an alanine.

Each mutated HA and NA protein comprising an alanine is subjected to in vitro and in vivo testing to determine what mutations will elicit an immune response to highly conserved amino acid regions and provide protection against influenza infection.

In one study, mutated HA or NA proteins, or combinations thereof, are administered to a subject (e.g., a pig). Serum, BAL, and TBLN samples are collected and tested in ELISA or neutralization assays to determine antibodies titers to the highly conserved amino acid regions. Generation of such antibodies indicates the immune response has been directed to such regions and thus the mutated proteins are suitable as a universal influenza vaccine. In another study, after administration of the mutated HA or NA proteins, or combinations thereof, subjects are challenged with various influenza virus strains and infection levels are monitored. The ability of the mutated HA or NA proteins to prevent infection by different influenza strains indicates the mutated proteins are suitable as a universal influenza vaccine.

Example 5: Production of T Cell Immune Response

To determine whether the highly conserved regions of amino acids identified in Examples 1-3 are capable of eliciting a T cell immune response, immunogenic compositions comprising polypeptides having amino acid sequences of the conserved regions are generated and administered to subjects. In some studies, polypeptides comprising different regions are combined by operably linking the polypeptides together.

PBMCS are collected at various time points after immunization, and are cultured with 15-mer peptide pools encompassing the sequence of the polypeptide or operably linked polypeptides. T cell activation is measured by assessing proliferation, production of cytokines and/or the cytotoxic ability of the cells against different influenza virus strains. The ability of the polypeptide or operably linked polypeptides to induce cytokine induction or induce killing of different strains by T cells indicates the polypeptide(s) are suitable as a universal influenza vaccine.

In another study, polypeptide(s) or operably linked polypeptides are administered to a subject (e.g., a pig) which is then challenged with various influenza virus strains and infection levels are monitored. The ability of the polypeptide(s) to prevent infection by different influenza strains indicates they are suitable as a universal influenza vaccine.

Example 6: Therapeutic Efficacy of Nucleic Acids Targeting Highly Conserved Regions To determine whether targeting the highly conserved regions identified in Examples 1-3 provides therapeutic efficacy, nucleic acid molecules (e.g., siRNA or miRNA) having substantial complementarity to nucleotide sequences encoding the highly conserved regions are generated.

In one study, a nucleic acid molecule targeting a highly conserved region is contacted with various influenza virus strains. Ability of the viruses to infect cells is assessed after contact. If the nucleic acid molecule disrupts the life cycle of the virus and prevents infection, the nucleic acid molecule may be suitable for treating influenza infection.

SEQUENCE LISTING TABLE

| SEQ ID NO | Description | Sequence |
|---|---|---|
| 1 | H1N1 Hemagglutinin A/Michigan/45/2015 strain (amino acid) GenBank: MK622940.1 | MKAILVVLLYTFTTANADTLCIGYHANNSTDT<br>VDTVLEKNVTVTHSVNLLEDKHNGKLCKLRGV<br>APLHLGKCNIAGWILGNPECESLSTASSWSYI<br>VETSNSDNGTCYPGDFINYEELREQLSSVSSF<br>ERFEIFPKTSSWPNHDSNKGVTAACPHAGAKS<br>FYKNLIWLVKKGNSYPKLNQSYINDKGKEVLV<br>LWGIHHPSTTADQQSLYQNADAYVFVGTSRYS<br>KKFKPEIATRPKVRDQEGRMNYYWTLVEPGDK<br>ITFEATGNLVVPRYAFTMERNAGSGIIISDTP<br>VHDCNTTCQTPEGAINTSLPFQNIHPITIGKC<br>PKYVKSTKLRLATGLRNVPSIQSRGLFGAIAG<br>FIEGGWTGMVDGWYGYHHQNEQGSGYAADLKS<br>TQNAIDKITNKVNSVIEKMNTQFTAVGKEFNH<br>LEKRIENLNKKVDDGFLDIWTYNAELLVLLEN<br>ERTLDYHDSNVKNLYEKVRNQLKNNAKEIGNG<br>CFEFYHKCDNTCMESVKNGTYDYPKYSEEAKL<br>NREKIDGVKLESTRIYQILAIYSTVASSLVLV<br>VSLGAISFWMCSNGSLQCRICI<br>(underline = highly conserved;<br>bold = hypervariable) |
| 2 | H1N1 Neuraminidase A/Michigan/45/2015 strain (amino acid) GenBank: MK622934.1 | MNPNQKIITIGSICMTIGMANLILQIGNIISI<br>WVSHSIQIGNQSQIETCNQSVITYENNTWVNQ<br>TYVNISNINFAAGQSVVSVKLAGNSSLCPVSG<br>WAIYSKDNSVRIGSKGDVFVIREPFISCSPLE<br>CRTFFLTQGALLNDKHSNGTIKDRSPYRTLMS<br>CPIGEVPSPYNSRFESVAWSASACHDGINWLT<br>IGISGPDSGAVAVLKYNGIITDTIKSWRNNIL<br>RTQESECACVNGSCFTIMIDGPSDGQASYKIF<br>RIEKGKIIKSVEMKAPNYHYEECSCYPDSSEI<br>TCVCRDNWHGSNRPWVSFNQNLEYQMGYICSG<br>VTGDNPRPNDKTGSCGPVSSNGANGVKGFSFK<br>YGNGVWIGRTKSISSRKGFEMIWDPNGWTGTD |

-continued

SEQUENCE LISTING TABLE

| SEQ ID NO | Description | Sequence |
| --- | --- | --- |
| | | NKFSIKQDIVGINEWSGYSGSFVQHPELTGLD<br>CIRPCFWVELIRGRPEENTIWTSGSSISFCGV<br>NSDTVGWSWPDGAELPFTIDK<br>(underline = highly conserved;<br>bold = hypervariable) |
| 3 | H3N2<br>Hemagglutinin<br>A/Mississippi/<br>27/2013 strain<br>(amino acid)<br>GenBank:<br>AIK26600.1 | MKTIIALSYILCLVFAQKLPPYGNSTATLCLG<br>HHALPNGTIVKTITNDRIEVTNATELVQNSSI<br>GEICDSPHQILDGENCTLIDALLGDPQCDGFQ<br>NKKWDLFVERSKAYSNCYPYDVPDYASLRSLV<br>ASSGTLEFNNESFNWTGVTQNGTSSACIRRSN<br>SSFFSRLNWLTHLNFKYPAINVIMPNNEQFDK<br>LYIWGVHHPGTDKDQIFLYAQSSGRITVSTKR<br>SQQAVIPNIGSRPRIRNIPSRISIYWTIVKPG<br>DILLINSTGNLIAPRGYFKIRSGKSSIMRSDA<br>PIGKCKSECITPNGSIPNDKPFQNVNRITYGA<br>CPRYVKQSTLKLATGMRNVPEKQTRGIFGAIA<br>GFIENGWEGMVDGWYGFRHQNSEGRGQAADLK<br>STQAAIDQINGKLNRLIGKTNEKFHQIEKEFS<br>EVEGRIQDLEKYVEDTKIDLWSYNAELLVALE<br>NQHTIDLTDSEMNKLFEKTKKQLRENAEDMGN<br>GCFKIYHKCDNACIGSIRNGTYDHNVYRDEAL<br>NNRFQIKGVELKSGYKDWILWISFAISCFLLC<br>VAIKGFIMWACQKGNIRCNIRCNICI<br>(underline = highly conserved;<br>bold = hypervariable) |
| 4 | H3N2<br>Neuraminidase<br>A/Miyagi/N12<br>89/2005 strain<br>(amino acid)<br>GenBank:<br>AB271522.1 | MNPNQKIITIGSVSLTISTICFFMQIAILITT<br>VTLHFKQYEFNSPPNNQVMLCEPTIIERNITE<br>IVYLTNTTIEKEICPKLAEYRKWSKPQCNITG<br>FAPFSKDNSIRLSAGGDIWVTREPYVSCDPDK<br>CYQFALGQGTTLNNVHSNDIVRDRTPYRTLLM<br>NELGVPFHLGTKQVCIAWSSSSCHDGKAWLHV<br>CVTGDDKNATASFIYNGRLVDSIVSWSKEILR<br>TQESECVCINGTCTVVMTDGSASGKADTKILF<br>IEEGKIVHTSTLSGSAQHVEECSCYPRYPGVR<br>CVCRDNWKGSNRPIVDINIKDYSIVSSYVCSG<br>LVGDTPRKNDSSSSSHCLDPNNEEGGHGVKGW<br>AFDDGNDVWMGRTISEKLRSGYETFXVIEGWS<br>NPNSKLQINRQVIVDRGNRSGYSGIFSVEGKS<br>CINRCFYVELIRGRKEETEVLWTSNSIVVFCG<br>TSGTYGTGSWPDGADINLMPI<br>(underline = highly conserved;<br>bold = hypervariable) |
| 5 | Influenza B<br>Hemagglutinin<br>B/Brisbane/60/<br>2008 strain<br>(amino acid)<br>GenBank:<br>KX058884.1 | MKAIIVLLMVVTSNADRICTGITSSNSPHVVK<br>TATQGEVNVTGVIPLTTTPTKSHFANLKGTET<br>RGKLCPKCLNCTDLDVALGRPKCTGKIPSARV<br>SILHEVRPVTSGCFPIMHDRTKIRQLPNLLRG<br>YEHIRLSTHNVINAENAPGGPYKIGTSGSCPN<br>ITNGNGFFATMAWAVPKNDKNKTATNPLTIEV<br>PYICTEGEDQITVWGFHSDDETQMAKLYGDSK<br>PQKFTSSANGVTTHYVSQIGGFPNQTEDGGLP<br>QSGRIVVDYMVQKSGKTGTITYQRGILLPQKV<br>WCASGRSKVIKGSLPLIGEADCLHEKYGGLNK<br>SKPYYTGEHAKAIGNCPIWVKTPLKLANGTKY<br>RPPAKLLKERGFFGAIAGFLEGGWEGMIAGWH<br>GYTSHGAHGVAVAADLKSTQEAINKITKNLNS<br>LSELEVKNLQRLSGAMDELHNEILELDEKVDD<br>LRADTISSQIELAVLLSNEGIINSEDEHLLAL<br>ERKLKKMLGPSAVEIGNGCFETKHKCNQTCLD<br>RIAAGTFDAGEFSLPTFDSLNITAASLNDDGL<br>DNHTILLYYSTAASSLAVTLMIAIFVVYMVSR<br>DNVSCSICL<br>(underline = highly conserved;<br>bold = hypervariable) |
| 6 | Influenza B<br>Neuraminidase<br>B/Wisconsin/<br>05/2016 strain<br>(amino acid)<br>GenBank: | MLPSTIQTLTLFLTSGGVLLSLYVSASLSYLL<br>YSDILLKFSPTEITAPTMPLDCANASNVQAVN<br>RSATKGVTLLLLPEPEWTYPRLSCPGSTFQKA<br>LLISPHRFGETKGNSAPLIIREPFVACGPNEC<br>KHFALTHYAAQPGGYYNGTRGDRNKLRHLISV<br>KLGKIPTVENSIFHMAAWSGSACHDGKEWTYI |

-continued

SEQUENCE LISTING TABLE

| SEQ ID NO | Description | Sequence |
|---|---|---|
| | KX007164.1 | GVDGPD**N**NALLK**V**KYGEAYTDTYHSYA**NN**ILR<br>TQESACNCIGG**N**CYLMITDG**S**ASG**V**SECRFLK<br>IREGRIIKEIFPTGRVKHTEECTCGFASNKTI<br>ECACRDN**R**YTAKRPFVKLNVETDTAEIRLMCT<br>**D**TYLDTPRP**N**DGSITGPCES**D**G**DK**GSGGIKGG<br>FVHQRM**K**SKIGRWYSRTMS**K**T**E**RMGMGLYVKY<br>**G**GDPW**A**DSDAL**AF**SGVM**VS**M**K**EPGWYSFGFEI<br>KDKKCDVPCIGIEMVHDGGK**E**TWHSAATAIYC<br>LMGSGQLLWDTVTGV**D**M**A**L<br>(underline = highly conserved;<br>bold = hypervariable) |
| 7 | H1N1 Hemagglutinin conserved region (amino acid) | GYHANNST |
| 8 | H1N1 Hemagglutinin conserved region (nucleic acid) | ggttatcatgcgaacaattcaaca |
| 9 | H1N1 Hemagglutinin conserved region (amino acid) | NVTVTHS |
| 10 | H1N1 Hemagglutinin conserved region (nucleic acid) | aatgtaacagtaacacactct |
| 11 | H1N1 Hemagglutinin conserved region (amino acid) | SWSYIVE |
| 12 | H1N1 Hemagglutinin conserved region (nucleic acid) | tcatggtcctacattgtggaa |
| 13 | H1N1 Hemagglutinin conserved region (amino acid) | QSRGLFGAIAGF |
| 14 | H1N1 Hemagglutinin conserved region (nucleic acid) | caatctagaggcctattcggggccattgccggcttc |
| 15 | H1N1 Hemagglutinin conserved region (amino acid) | QGSGYAAD |

-continued

SEQUENCE LISTING TABLE

| SEQ ID NO | Description | Sequence |
|---|---|---|
| 16 | H1N1 Hemagglutinin conserved region (nucleic acid) | caggggtcaggatatgcagccgac |
| 17 | H1N1 Hemagglutinin conserved region (amino acid) | ITNKVNS |
| 18 | H1N1 Hemagglutinin conserved region (nucleic acid) | attactaacaaagtaaattct |
| 19 | H1N1 Hemagglutinin conserved region (amino acid) | WTYNAELL |
| 20 | H1N1 Hemagglutinin conserved region (nucleic acid) | tggacttacaatgccgaactgttg |
| 21 | H1N1 Hemagglutinin conserved region (amino acid) | GCFEFYH |
| 22 | H1N1 Hemagglutinin conserved region (nucleic acid) | gcctgctttgaattttaccac |
| 23 | H1N1 Hemagglutinin conserved region (amino acid) | LGNPEC |
| 24 | H1N1 Hemagglutinin conserved region (nucleic acid) | ctgggaaatccagagtgt |
| 25 | H1N1 Hemagglutinin conserved region (amino acid) | EGGWTG |

-continued

SEQUENCE LISTING TABLE

| SEQ ID NO | Description | Sequence |
|---|---|---|
| 26 | H INI Hemagglutinin conserved region (nucleic acid) | gaaggggggtggacaggg |
| 27 | H1N1 Hemagglutinin conserved region (amino acid) | LLENER |
| 28 | H1N1 Hemagglutinin conserved region (nucleic acid) | ctattggaaaatgaaaga |
| 29 | H1N1 Neuraminidase conserved region (amino acid) | MNPNQKI1TIGS |
| 30 | H1N1 Neuraminidase conserved region (nucleic acid) | atgaatccaaaccaaaagataataaccattggttcg |
| 31 | H1N1 Neuraminidase conserved region (amino acid) | RIGSKGDVFV |
| 32 | H1N1 Neuraminidase conserved region (nucleic acid) | agaatcggttccaagggggatgtgtttgtc |
| 33 | H1N1 Neuraminidase conserved region (amino acid) | REPFISCS |
| 34 | H1N1 Neuraminidase conserved region (nucleic acid) | agggaaccattcatatca |
| 35 | H1N1 Neuraminidase conserved region (amino acid) | TFFLTQGALLNDKHSNGT |
| 36 | H1N1 Neuraminidase conserved region (nucleic acid) | accttcttcttgactcaaggggccttgctaaa tgacaaacattccaatggaacc |

-continued

SEQUENCE LISTING TABLE

| SEQ ID NO | Description | Sequence |
|---|---|---|
| 37 | H1N1 Neuraminidase conserved region (amino acid) | KDRSPYR |
| 38 | H1N1 Neuraminidase conserved region (nucleic acid) | aaagacaggagcccataccga |
| 39 | H1N1 Neuraminidase conserved region (amino acid) | FESVAWSASACHDG |
| 40 | H1N1 Neuraminidase conserved region (nucleic acid) | tttgagtcagtcgcttggtcagcaagtgcttgtcatgatggc |
| 41 | H1N1 Neuraminidase conserved region (amino acid) | WLTIGISGPD |
| 42 | H1N1 Neuraminidase conserved region (nucleic acid) | tggctaacaattggaatttctggcccagac |
| 43 | H1N1 Neuraminidase conserved region (amino acid) | ILRTQESEC |
| 44 | H1N1 Neuraminidase conserved region (nucleic acid) | atattgagaacacaagagtctgaatgt |
| 45 | H1N1 Neuraminidase conserved region (amino acid) | YEECSCYPD |
| 46 | H1N1 Neuraminidase conserved region (nucleic acid) | tatgaggaatgctcctgttaccctgat |

-continued

SEQUENCE LISTING TABLE

| SEQ ID NO | Description | Sequence |
|---|---|---|
| 47 | H1N1 Neuraminidase conserved region (amino acid) | CVCRDNWHGSNRPWVSFNQNL |
| 48 | H1N1 Neuraminidase conserved region (nucleic acid) | tgtgtgtgcagggataactggcatggctcga atcgaccgtgggtgtctttcaaccagaatctg |
| 49 | H1N1 Neuraminidase conserved region (amino acid) | NGVWIGRTKS |
| 50 | H1N1 Neuraminidase conserved region (nucleic acid) | aatggtgtttggatagggagaactaaaagc |
| 51 | H1N1 Neuraminidase conserved region (amino acid) | GFEMIWDPNGWT |
| 52 | H1N1 Neuraminidase conserved region (nucleic acid) | ggttttgagatgatttgggatccgaatggatggact |
| 53 | H1N1 Neuraminidase conserved region (amino acid) | WSGYSGSFVQHPELTGL |
| 54 | H1N1 Neuraminidase conserved region (nucleic acid) | tggtcagggtatagcgggagttttgttcagcatcc agaactaacagggctg |
| 55 | H1N1 Neuraminidase conserved region (amino acid) | RPCFWVEL |
| 56 | H1N1 Neuraminidase conserved region (nucleic acid) | agaccttgcttctgggttgaacta |

-continued

SEQUENCE LISTING TABLE

| SEQ ID NO | Description | Sequence |
|---|---|---|
| 57 | H1N1 Neuraminidase conserved region (amino acid) | WTSGSS1SFCGV |
| 58 | H1N1 Neuraminidase conserved region (nucleic acid) | tggactagcgggagcagcatatccttttgtggtgta |
| 59 | H1N1 Neuraminidase conserved region (amino acid) | WSWPDGAELPF |
| 60 | H1N1 Neuraminidase conserved region (nucleic acid) | tggtcttggccagacggtgctgagttgccattt |
| 61 | H3N2 Hemagglutinin conserved region (amino acid) | LCLGHHA |
| 62 | H3N2 Hemagglutinin conserved region (nucleic acid) | ctgtgccttgggcaccatgcatta |
| 63 | H3N2 Hemagglutinin conserved region (amino acid) | GNLIAPRGYF |
| 64 | H3N2 Hemagglutinin conserved region (nucleic acid) | gggaatctaattgctcctaggggttacttc |
| 65 | H3N2 Hemagglutinin conserved region (amino acid) | LKLATGMRN |
| 66 | H3N2 Hemagglutinin conserved region (nucleic acid) | ctgaaattggcaacaggaatgcgaaat |

-continued

SEQUENCE LISTING TABLE

| SEQ ID NO | Description | Sequence |
|---|---|---|
| 67 | H3N2 Hemagglutinin conserved region (amino acid) | FGAIAGFIENGWEG |
| 68 | H3N2 Hemagglutinin conserved region (nucleic acid) | tttggcgcaatagcaggtttcatagaaaatggttgggagggg |
| 69 | H3N2 Hemagglutinin conserved region (amino acid) | KFHQIEKEF |
| 70 | H3N2 Hemagglutinin conserved region (nucleic acid) | aaattccatcagattgaaaaagaattc |
| 71 | H3N2 Hemagglutinin conserved region (amino acid) | DLTDSEM |
| 72 | H3N2 Hemagglutinin conserved region (nucleic acid) | gatctaactgactcagaaatg |
| 73 | H3N2 Hemagglutinin conserved region (amino acid) | LRENAED |
| 74 | H3N2 Hemagglutinin conserved region (nucleic acid) | ctgagggaaaatgctgaggat |
| 75 | H3N2 Neuraminidase conserved region (amino acid) | QFALGQGTT |
| 76 | H3N2 Neuraminidase conserved region (nucleic acid) | caatttgcccttggacagggaacaaca |

-continued

SEQUENCE LISTING TABLE

| SEQ ID NO | Description | Sequence |
|---|---|---|
| 77 | H3N2 Neuraminidase conserved region (amino acid) | AWSSSSC |
| 78 | H3N2 Neuraminidase conserved region (nucleic acid) | gcatggtccagctcaagttgt |
| 79 | H3N2 Neuraminidase conserved region (amino acid) | LRTQESEC |
| 80 | H3N2 Neuraminidase conserved region (nucleic acid) | ctcaggacccaggagtcagaatgc |
| 81 | H3N2 Neuraminidase conserved region (amino acid) | EECSCYP |
| 82 | H3N2 Neuraminidase conserved region (nucleic acid) | gaggagtgctcctgctatcct |
| 83 | H3N2 Neuraminidase conserved region (amino acid) | CSGLVGDTPR |
| 84 | H3N2 Neuraminidase conserved region (nucleic acid) | tgctcaggacttgttggagacacacccaga |
| 85 | H3N2 Neuraminidase conserved region (amino acid) | GVKGWAFD |
| 86 | H3N2 Neuraminidase conserved region (nucleic acid) | ggagtgaaaggctgggcctttgat |

-continued

SEQUENCE LISTING TABLE

| SEQ ID NO | Description | Sequence |
|---|---|---|
| 87 | H3N2 Neuraminidase conserved region (amino acid) | NRCFYVELIRG |
| 88 | H3N2 Neuraminidase conserved region (nucleic acid) | aatcggtgcttttatgtggagttgataaggga |
| 89 | H3N2 Neuraminidase conserved region (amino acid) | VFCGTSGTYG |
| 90 | H3N2 Neuraminidase conserved region (nucleic acid) | gtgttttgtggcacctcaggtacatatgga |
| 91 | H3N2 Neuraminidase conserved region (amino acid) | GSWPDGA |
| 92 | H3N2 Neuraminidase conserved region (nucleic acid) | ggctcatggcctgatggggcg |
| 93 | Influenza B Hemagglutinin conserved region (amino acid) | VKTATQEVNVTG |
| 94 | Influenza B Hemagglutinin conserved region (nucleic acid) | gtcaaaactgctactcaaggggaggtcaatgtgactggt |
| 95 | Influenza B Hemagglutinin conserved region (amino acid) | NCTDLDVAL |
| 96 | Influenza B Hemagglutinin conserved region (nucleic acid) | aactgcacagatctggacgtagccttg |
| 97 | Influenza B Hemagglutinin conserved | TSGCFPIMHDRTKIRQL |

-continued

SEQUENCE LISTING TABLE

| SEQ ID NO | Description | Sequence |
|---|---|---|
| | region (amino acid) | |
| 98 | Influenza B Hemagglutinin conserved region (nucleic acid) | acatctgggtgctttcctataatgcacgac agaacaaaaattagacagctg |
| 99 | Influenza B Hemagglutinin conserved region (amino acid) | NLLRGYE |
| 100 | Influenza B Hemagglutinin conserved region (nucleic acid) | aaccttctccgaggatacgaa |
| 101 | Influenza B Hemagglutinin conserved region (amino acid) | TMAWAVP |
| 102 | Influenza B Hemagglutinin conserved region (nucleic acid) | acaatggcttgggccgtccca |
| 103 | Influenza B Hemagglutinin conserved region (amino acid) | EDGGLPQSGRIVVDYM |
| 104 | Influenza B Hemagglutinin conserved region (nucleic acid) | gaagacggaggactaccacaaagtggta gaattgttgttgattacatg |
| 105 | Influenza B Hemagglutinin conserved region (amino acid) | LPLIGEADCLHE |
| 106 | Influenza B Hemagglutinin conserved region (nucleic acid) | ttgcctttaattggagaagcagattgcctccacgaa |
| 107 | Influenza B Hemagglutinin conserved region (amino acid) | YGGLNKSKPYYTG |

-continued

SEQUENCE LISTING TABLE

| SEQ ID NO | Description | Sequence |
|---|---|---|
| 108 | Influenza B Hemagglutinin conserved region (nucleic acid) | tacggtggattaaacaaaagcaagccttactacacaggg |
| 109 | Influenza B Hemagglutinin conserved region (amino acid) | CPIWVKTPL |
| 110 | Influenza B Hemagglutinin conserved region (nucleic acid) | tgcccaatatgggtgaaaacacccttg |
| 111 | Influenza B Hemagglutinin conserved region (amino acid) | GFFGAIAGFLEGGWEGM |
| 112 | Influenza B Hemagglutinin conserved region (nucleic acid) | ggtttcttcggagctattgctggtttcttag aaggaggatgggaaggaatg |
| 113 | Influenza B Hemagglutinin conserved region (amino acid) | AGWHGYTSHGAHG |
| 114 | Influenza B Hemagglutinin conserved region (nucleic acid) | gcaggttggcacggatacacatcccatggggcacatgga |
| 115 | Influenza B Hemagglutinin conserved region (amino acid) | AVAADLKSTQEA |
| 116 | Influenza B Hemagglutinin conserved region (nucleic acid) | gcggtggcagcagaccttaagagcactcaagaggcc |
| 117 | Influenza B Hemagglutinin conserved region (amino acid) | KITKNLNSLSELE |

-continued

SEQUENCE LISTING TABLE

| SEQ ID NO | Description | Sequence |
|---|---|---|
| 118 | Influenza B Hemagglutinin conserved region (nucleic acid) | aagataacaaaaaatctcaactctttgagtgagctggaa |
| 119 | Influenza B Hemagglutinin conserved region (amino acid) | KNLQRLS |
| 120 | Influenza B Hemagglutinin conserved region (nucleic acid) | aagaatcttcaaagactaagc |
| 121 | Influenza B Hemagglutinin conserved region (amino acid) | EILELDEKVDDLRADTISSQIELAVLLSNEGIINSED EHLLALERKLKKMLGPSA |
| 122 | Influenza B Hemagglutinin conserved region (nucleic acid) | gaaatactagaactagatgagaaagtggatga tctcagagctgatacaataagctcacaaatag aactcgcagtcctgctttccaatgaaggaata ataaacagtgaagatgaacatctcttggcgct tgaaagaaagctgaagaaaatgctgggcccct ctgct |
| 123 | Influenza B Hemagglutinin conserved region (amino acid) | IGNGCFETKHKCNQTCLD |
| 124 | Influenza B Hemagglutinin conserved region (nucleic acid) | atagggaatggatgctttgaaaccaaac acaagtgcaaccagacctgtctcgac |
| 125 | Influenza B Hemagglutinin conserved region (amino acid) | AGEFSLPTFDSLNITAASL |
| 126 | Influenza B Hemagglutinin conserved region (nucleic acid) | gcaggagaattttctctccccacctttg attcactgaatattactgctgcatcttta |
| 127 | Influenza B Hemagglutinin conserved region (amino acid) | HTILLYYSTAASSLAVTLM |
| 128 | Influenza B Hemagglutinin conserved | catactatactgctttactactcaactgc tgcctccagtttggctgtaacactgatg |

-continued

SEQUENCE LISTING TABLE

| SEQ ID NO | Description | Sequence |
|---|---|---|
| | region (nucleic acid) | |
| 129 | Influenza B Neuraminidase conserved region (amino acid) | ALLISPHRFGE |
| 130 | Influenza B Neuraminidase conserved region (nucleic acid) | gcactcctaattagccctcatagattcggagaa |
| 131 | Influenza B Neuraminidase conserved region (amino acid) | HFALTHYAAQPG |
| 132 | Influenza B Neuraminidase conserved region (nucleic acid) | cactttgctttaacccattatgcagcccaaccaggg |
| 133 | Influenza B Neuraminidase conserved region (amino acid) | DRNKLRHL |
| 134 | Influenza B Neuraminidase conserved region (nucleic acid) | gacagaaacaagctgaggcatcta |
| 135 | Influenza B Neuraminidase conserved region (amino acid) | AWSGSACHDG |
| 136 | Influenza B Neuraminidase conserved region (nucleic acid) | gcatggagcgggtccgcgtgccatgatggt |
| 137 | Influenza B Neuraminidase conserved region (amino acid) | KYGEAYTDTYHSY |
| 138 | Influenza B Neuraminidase conserved region (nucleic acid) | aaatatggagaagcatatactgacacataccattcctat |

-continued

SEQUENCE LISTING TABLE

| SEQ ID NO | Description | Sequence |
|---|---|---|
| 139 | Influenza B Neuraminidase conserved region (amino acid) | LRTQESACNCI |
| 140 | Influenza B Neuraminidase conserved region (nucleic acid) | ctaagaacacaagaaagtgcctgcaattgcatc |
| 141 | Influenza B Neuraminidase conserved region (amino acid) | CRFLKIREGR |
| 142 | Influenza B Neuraminidase conserved region (nucleic acid) | tgcagatttcttaagattcgagagggccga |
| 143 | Influenza B Neuraminidase conserved region (amino acid) | HTEECTCGFA |
| 144 | Influenza B Neuraminidase conserved region (nucleic acid) | cacactgaggaatgcacatgcggatttgcc |
| 145 | Influenza B Neuraminidase conserved region (amino acid) | YTAKRPFVKL |
| 146 | Influenza B Neuraminidase conserved region (nucleic acid) | tacacagcaaaaagaccttttgtcaaatta |
| 147 | Influenza B Neuraminidase conserved region (amino acid) | KGGFVHQR |
| 148 | Influenza B Neuraminidase conserved region (nucleic acid) | aagggaggatttgttcatcaaaga |

-continued

SEQUENCE LISTING TABLE

| SEQ ID NO | Description | Sequence |
|---|---|---|
| 149 | Influenza B Neuraminidase conserved region (amino acid) | GRWYSRT |
| 150 | Influenza B Neuraminidase conserved region (nucleic acid) | ggaaggtggtactctcgaacg |
| 151 | Influenza B Neuraminidase conserved region (amino acid) | EPGWYSFGFE |
| 152 | Influenza B Neuraminidase conserved region (nucleic acid) | gaacctggttggtattcctttggcttcgaa |
| 153 | Influenza B Neuraminidase conserved region (amino acid) | EMVHDGG |
| 154 | Influenza B Neuraminidase conserved region (nucleic acid) | gagatggtacatgatggtgga |
| 155 | H1N1 Neuraminidase conserved region (amino acid) | GAVAVLKY |
| 156 | H1N1 Neuraminidase conserved region (nucleic acid) | ggggcagtggctgtgttaaagtac |
| 157 | Variant of H1N1 Hemagglutinin A/Michigan/45/ 2015 strain (amino acid) GenBank: MK622940.1 Hypervariable residues substituted with Ala | MKAILVVLLYTFAAANADTLCIGYH ANNSTDTVDTVLEKNVTVTHSVNLL EAAHNGKLCKLRGVAPLHLGKCNIA GWALGNPECEALATASSWSYIVETS ASDNGTCYPGDFIAYEELREQLSSV SSFERFEIFPKASSWPNHDANAGVT AACPAAGAAAFYANLIWLVKKGNSY PKAAASYINAKAKEVLVLWAIHHPA TAADQQSLYQNADAYVFVGASAYSA KFAPEIAARPKVRAQAGRMNYYWTL AEPGDAITFEATGNLVVPRYAFAAA RAAGSGIIISDAAVHDCATTCQTPA GAINTSLPFQNIHPATIGACPKYVK STKLRAATGLRNAPSIQSRGLFGAI AGFIEGGWTGMADGWYGYHHQNEQG SGYAADAKSTQNAIDAITNKVNSVI EKMNTQFTAVGKEFAHLEARIENLN |

-continued

| SEQUENCE LISTING TABLE | | |
|---|---|---|
| SEQ ID NO | Description | Sequence |
| | | KKVDDGFLDIWTYNAELLVLLENER TLDYHDSNVKNLYEKVRAQLKNNAK EIGNGCFEFYHKCDAACMESVKNGT YDYPKYSEEAKLNREAIDGVKLEST RIYQILAIYSTVASSLVLAVSLGAI SFWMCSNGSLQCRICI* |
| 158 | Influenza A H1N1 Hemagglutinin 2009 residues 145-229 | SNKGVTAACPHAGAKSFYKNLIWLVKKGNSYPKLSKSYIN DKGKEVLVLWGIHHPSTSADQQSLYQNADAYVFVGSSRYS KKFKP |
| 159 | Influenza A H1N1 Hemagglutinin 2010 residues 145-229 | SNKGVTAACPHAGAKSFYKNLIWLVKKGNSYPKLSKSYIN DKGKEVLVLWGIHHPPTSADQQSLYQNADAYVFVGTSRYS KKFKP |
| 160 | Influenza A H1N1 Hemagglutinin 2011 residues 145-229 | TTRGTTVACSHSGANSFYRNLLWIVKKGNSYPKLSKSYTNN KGKEVLVIWGVHHPPTDSDQQTLYQNNHTYVSVGSSKYYK RLTP |
| 161 | Influenza A H1N1 Hemagglutinin 2012 residues 145-229 | SNKGVTAACPHAGAKGFYKNLIWLVKKGNSYPKLSKSYIN DKGKEVLVLWGIHHPSTTADQQSLYQNADTYWVGTSRYS KKFKP |
| 162 | Influenza A H1N1 Hemagglutinin 2013 residues 145-229 | SNKGVTAACPHAGAKSFYKNLIWLVKKGNSYPKLSKSYIN DKGKEVLVLWGIHHPSTTADQQSLYQNANAYVFVGTSKYS KKFKP |
| 163 | Influenza A H1N1 Hemagglutinin 2014 residues 145-229 | SNKGVTAACPHAGAKSFYKNLIWLVKKGNSYPKLSKSYIN DKGKEVLVLWGIHHPSTSADQQSLYQNADAYVFVGTSRYS KKFKP |
| 164 | Influenza A H1N1 Hemagglutinin 2015 residues 145-229 | SNKGVTAACPHAGAKSFYKNLIWLVKKGNSYPKLSKSYIN DKGKEVLVLWGIHHPSTSADQQSLYQNADAYWVGTSRYS KKFKP |
| 165 | Influenza A H1N1 Hemagglutinin 2016 residues 145-229 | SNKGVTAACPHAGAKSFYKNLIWLVKKGNSYPKLNQSYIN DKGKEVLVLWGIHHPSTTADQQSLYQNADAYVFVGTSRYS KKFKP |
| 166 | Influenza A H1N1 Hemagglutinin 2017 residues 145-229 | SNKGVTAACPHAGAKSFYKNLIWLVKKGNSYPKLNQTYIN DKGKEVLVLWGIHHPPTTADQQSLYQNADAYVFVGTSRYS KKFKP |
| 167 | Influenza A HIN1 Hemagglutinin 2018 residues 145-229 | SDKGVTAACPHAGAKSFYKNLIWLVKKGNSYPKLNQTYIN DKGKEVLVLWGIHHPPTIADQQSLYQNADAYVFVGTSRYS KKFKP |
| 168 | Influenza A H1N1 Hemagglutinin 2019 residues 145-229 | SNKGVTAACPHAGAKSFYKNLIWLVKKGNSYPKINQTYIND KGKEVLVLWGIHHPPTTADQQSLYQNADAYVFVGTSRYSK KFKP |

-continued

SEQUENCE LISTING TABLE

| SEQ ID NO | Description | Sequence |
|---|---|---|
| 169 | H1N1 Hemagglutinin A/Michigan/ 45/2015 strain (nucleotide) GenBank: MK622940.1 | atgaaggcaatactagtagttctgctatat acatttacaaccgcaaatgcagacacatta tgtataggttatcatgcgaacaattcaaca gacactgtagacacagtactagaaaagaat gtaacagtaacacactctgttaaccttctg gaagacaagcataacggaaaactatgcaaa ctaagaggggtagccccattgcatttgggt aaatgtaacattgctggctggatcctggga aatccagagtgtgaatcrctctccacagca agttcatggtcctacattgtggaaacatct aattcagacaatggaacgtgttacccagga gatttcatcaattatgaggagctaagagag caattgagctcagtgtcatcatttgaaagg tttgagatattccccaagacaagttcatgg cccaatcatgactcgaacaaaggtgtaacg gcagcatgtcctcacgctggagcaaaaagc ttctacaaaaacttgatatggctagttaaa aaaggaaattcatacccaaagcttaaccaa tcctacattaatgataaagggaaagaagtc ctcgtgctgtggggcattcaccatccatct actactgctgaccaacaaagtctctatcag aatgcagatgcatatgtttttgtggggaca tcaagatacagcaagaagttcaagccggaa atagcaacaagacccaaagtgagggatcaa gaagggagaatgaactattactggacacta gtagagccgggagacaaaataacattcgaa gcaactggaaatctagtggtaccgagatat gcattcacaatggaaagaaatgctggatct ggtattatcatttcagatacaccagtccac gattgcaatacaacttgtcagacacccgag ggtgctataaacaccagcctcccatttcag aatatacatccgatcacaattggaaaatgt ccaaagtatgtaaaaagcacaaaattgaga ctggccacaggattgaggaatgttccgtct attcaatctagaggcctattcggggccatt gccggcttcattgaagggggtggacaggg atggtagatggatggtacggttatcaccat caaaatgagcaggggtcaggatatgcagcc gacctgaagagcacacaaaatgccattgac aagattactaacaaagtaaattctgttatt gaaaagatgaatacacagttcacagcagtg ggtaaagagttcaaccacctggaaaaaaga atagagaatctaaataaaaaagttgatgat ggtttcctggacatttggacttacaatgcc gaactgttggttctattggaaaatgaaaga actttggactatcacgattcaaatgtgaag aacttgtatgaaaaagtaagaaaccagtta aaaaacaatgccaaggaaattggaaacggc tgctttgaattttaccacaaatgcgataac acgtgcatggaaagtgtcaaaaatgggact tatgactacccaaaatactcagaggaagca aaattaaacagagaaaaaatagatggggta aagctggaatcaacaaggatttaccagatt ttggcgatctattcaactgtcgccagttca ttggtactggtagtctccctgggggcaatc agcttctggatgtgctctaatgggtctcta cagtgtagaatatgtatttaa |
| 170 | Variant of H1N1 Hemagglutinin A/Michigan/ 45/2015 strain (nucleotide) GenBank: MK622940.1 Hypervariable residues substituted with Ala | atgaaggcaatactagtagttctgctatat acatttgcagccgcaaatgcagacacatta tgtataggttatcatgcgaacaattcaaca gacactgtagacacagtactagaaaagaat gtaacagtaacacactctgttaaccttctg gaagccgcgcataacggaaaactatgcaaa ctaagaggggtagccccattgcatttgggt aaatgtaacattgctggctgggccctggga aatccagagtgtgaagcrctcgccacagca agttcatggtcctacattgtggaaacatct gcttcagacaatggaacgtgttacccagga gatttcatcgcttatgaggagctaagagag caattgagctcagtgtcatcatttgaaagg tttgagatattccccaaggcaagttcatgg cccaatcatgacgcgaacgcaggtgtaacg |

-continued

SEQUENCE LISTING TABLE

| SEQ ID NO | Description | Sequence |
|---|---|---|
| | | gcagcatgtcctgccgctggagcagcagcc<br>ttctacgcaaacttgatatggctagttaaa<br>aaaggaaattcatacccaaaggctgccgca<br>tcctacattaatgctaaagcgaaagaagtc<br>ctcgtgctgtgggccattcaccatccagct<br>actgctgctgaccaacaaagtctctatcag<br>aatgcagatgcatatgtttttgtggggaca<br>tcagcatacagcgcgaagttcgcgccggaa<br>atagcagcaagacccaaagtgagggctcaa<br>gcagggagaatgaactattactggacacta<br>gcagagccgggagacgcaataacattcgaa<br>gcaactggaaatctagtggtaccgagatat<br>gcattcgcagcggcaagagctgctggatct<br>ggtattatcatttcagatgcagcagtccac<br>gattgcgctacaacttgtcagacacccgcg<br>ggtgctataaacaccagcctcccatttcag<br>aatatacatccggccacaattggagcatgt<br>ccaaagtatgtaaaaagcacaaaattgaga<br>gcggccacaggattgaggaatgctccgtct<br>attcaatctagaggcctattcggggccatt<br>gccggcttcattgaagggggggtggacaggg<br>atggcagatggatggtacggttatcaccat<br>caaaatgagcaggggtcaggatatgcagcc<br>gacgcgaagagcacacaaaatgccattgac<br>gcgattactaacaaagtaaattctgttatt<br>gaaaagatgaatacacagttcacagcagtg<br>ggtaaagagttcgcccacctggaagcaaga<br>atagagaatctaaataaaaaagttgatgat<br>ggtttcctggacatttggacttacaatgcc<br>gaactgttggttctattggaaaatgaaaga<br>actttggactatcacgattcaaatgtgaag<br>aacttgtatgaaaaagtaagagcccagtta<br>aaaaacaatgccaaggaaattggaaacggc<br>tgctttgaattttaccacaaatgcgatgcc<br>gcgtgcatggaaagtgtcaaaaatgggact<br>tatgactacccaaaatactcagaggaagca<br>aaattaaacagagaagcaatagatggggta<br>aagctggaatcaacaaggatttaccagatt<br>ttggcgatctattcaactgtcgccagttca<br>ttggtactggcagtctccctgggggcaatc<br>agcttctggatgtgctctaatgggtctcta<br>cagtgtagaatatgtatttaa |
| 171 | H3N2 M1 Protein | MSLLTEVETYVLSIVPSGPLKAEIAQRLEDVFAGKNTDLEAL<br>MEWLKTRPILSPLTKGILGFVFTLTVPSERGLQRRRFVQNAL<br>NGNGDPNNMDKAVKLYRKLKREITFHGAKEIALSYSAGAL<br>ASCMGLIYNRMGAVTTEVAFGLVCATCEQIADSQHRSHRQ<br>MVATTNPLIKHENRMVLASTTAKAMEQMAGSSEQAAEAM<br>EIASQARQMVQAMRAIGTHPSSSTGLRDDLLENLQTYQKR<br>MGVQMQRFK<br>(underline = highly conserved;<br>bold = hypervariable) |
| 172 | H3N2 NEP Protein | MDSNTVSSFQDILLRMSKMQLGSSSEDLNGMITQFESLKIY<br>RDSLGEAVMRMGDLHLLQNRNGKWREQLGQKFEEIRWLIE<br>EVRHRLRTTENSFEQITFMQALQLLFEVEQEIRTFSFQLI<br>(underline = highly conserved;<br>bold = hypervariable) |
| 173 | H3N2 NP Protein | MASQGTKRSYEQMETDGDRQNATEIRASVGKMIDGIGRFYI<br>QMCTELKLSDHEGRLIQNSLTIEKMVLSAFDERRNKYLEEH<br>PSAGKDPKKTGGPIYRRVDGKWMRELVLYDKEEIRRIWRQ<br>ANNGEDATSGLTHIMIWHSNLNDATYQRTRALVRTGMDPR<br>MCSLMQGSTLPRRSGAAGAAVKGIGTMVMELIRMVKRGIN<br>DRNFWRGENGRKTRSAYERMCNILKGKFQTAAQRAMVDQ<br>VRESRNPGNAEIEDLIFLARSALILRGSVAHKSCLPACAYGP<br>AVSSGYDFEKEGYSLVGIDPFKLLQNSQIYSLIRPNENPAHK<br>SQLVWMACHSAAFEDLRLLSFIRGTKVSPRGKLSTRGVQIA<br>SNENMDNMGSSTLELRSGYWAIRTRSGGNTNQQRASAGQ |

-continued

SEQUENCE LISTING TABLE

| SEQ ID NO | Description | Sequence |
|---|---|---|
| | | TSVQPTFSVQRNLPFEKSTIMAAFTGNTEGRTSDMRAEIIR<br>MMEGAKPEEVSFRGRGVFELSDEKATNPIVPSFDMSNEGSY<br>FFGDNAEEYDN<br>(underline = highly conserved;<br>bold = hypervariable) |
| 174 | H3N2 NS1 Protein | MDSNTVSSFQVDCFLWHIRKQVVDQKLSDAPFLDRLRRDQ<br>RSLRGRGNTLGLDIKAATHVGKQIVEKILKEESDEALKMT<br>MVSTPASRYITDMTIEELSRNWFMLMPKQKVEGPLCIRMD<br>QAIMEKNIMLKANFNVIFGRLETIVLLRAFTEEGAIVGEISPL<br>PSFPGHTIEDVKNAIGVLIGGLEWNDNTVRVSKNLQRFAWR<br>SSNENGGPPLTPK<br>(underline = highly conserved;<br>bold = hypervariable) |
| 175 | H3N2 NS2 Protein | MDSNTVSSFQDILLRMSKMQLGSSSEDLNGMITQFESLKIYR<br>DSLGEAVMRMGDLHLLQNRNGKWREQLGQKFEEIRWLIEE<br>VRHRLKTTENSFEQITFMQALQLLFEVEQEIRTFSFQLI<br>(underline = highly conserved;<br>bold = hypervariable) |
| 176 | H3N2 PA Protein | MEDFVRQCFNPMIVELAEKAMKEYGEDLKIETNKFAAICTH<br>LEVCFMYSDFHFINEQGESIVVELDDPNALLKHRFEIIEGRD<br>RTMAWTVVNSICNTTGAGKPKFLPDLYDYKENRFIEIGVTR<br>REVHIYYLEKANKIKSENTHIHIFSFTGEEMATKADYTLDEE<br>SRARIKTRLFTIRQEMANRGLWDSFRQSERGEETIEEKFEITG<br>TMRRLADQSLPPNFSCLENFRAYVDGFEPNGCIEGKLSQMS<br>KEVNAQIEPFLKTTPRPIKLPSGPPCYQRSKFLLMDALKLSIE<br>DPSHEGEGIPLYDAIKCIKTFFGWKEPYIVKPHEKGINSNYLL<br>SWKQVLSELQDIENEEKIPRTKNMKKTSQLKWALGENMAP<br>EKVDFENCRDISDLKQYDSEEPELRSLSSWIQSEFNKACELT<br>DSVWIELDEIGEDVAPIEHIASMRRNYFTAEVSHCRATEYIM<br>KGVYINTALLNASCAAMDDFQLIPMISKCRTKEGRRKTNLY<br>GFIIKGRSHLRNDTDVVNFVSMEFSLTDPRLEPHKWEKYCV<br>LEIGDMLLRSAIGQISRPMFLYVRTNGTSKVKMKWGMEMR<br>RCLLQSLQQIESMIEAESSVKEKDMTKEFFENKSEAWPIGES<br>PKGVEEGSIGKVCRTLLAKSVFNSLYASPQLEGFSAESRKLL<br>LIVQALRDKLEPGTFDLGGLYEAIEECLINDPWVLLNASWF<br>NSFLTHALK<br>(underline = highly conserved;<br>bold = hypervariable) |
| 177 | H3N2 PA-X Protein | MEDFVRQCFNPMIVELAEKAMKEYGEDLKIETNKFAAICTH<br>LEVCFMYSDFHFINEQGESIVVELDDPNALLKHRFEIIEGRD<br>RTMAWTVVNSICNTTGAGKPKFLPDLYDYKENRFIEIGVTR<br>REVHIYYLEKANKIKSENTHIHIFSFTGEEMATKADYTLDEE<br>SRARIKTRLFTIRQEMANRGLWDSFVSPKEAKKQLKKNLKS<br>QELCAGLPTKVSHRTSPALRILEPMWMDSNRTAALRASFLK<br>CPKK<br>(underline = highly conserved;<br>bold = hypervariable) |
| 178 | H3N2 PB1 Protein | MDVNPTLLFLKVPAQNAISTTFPYTGDPPYSHGTGTGYTMD<br>TVNRTHQYSERGKWTTNTETGAPQLNPIDGPLPEDNEPSGY<br>AQTDCVLEAMAFLEESHPGIFENSCLETMEAVQQTRVDKLT<br>QGRQTYDWTLNRNQPAATALANTIEVFRSNGLTANESGRLI<br>DFLKDVMESMDKEEMEITTHFQRKRRVRDNMTKKMVTQR<br>TIGKKKQRVNKRGYLIRALTLNTMTKDAERGKLKRRAIATP<br>GMQIRGFVYFVETLARSICEKLEQSGLPVGGNEKKAKLANV<br>VRKMMTNSQDTELSFTITGDNTKWNENQNPRMFLAMITYIT<br>KNQPEWFRNILSIAPIMFSNKMARLGKGYMFESKRMKLRT<br>QIPAEMLASIDLKYFNESTRKKIEKIRPLLIDGTASLSPGMM<br>MGMFNMLSTVLGVSILNLGQKKYTKTTYWWDGLQSSDDF<br>ALIVNAPNHEGIQAGVDRFYRTCKLVGINMSKKKSYINKTG<br>TFEFTSFFYRYGFVANFSMELPSFGVSGINESADMSIGVTVIK<br>NNMINNDLGPATAQMALQLFIKDYRYTYRCHRGDTQIQTR<br>RSFEIKKLWDQTQSRTGLLVSDGGPNLYNIRNLHIPEVCLK<br>WELMDENYRGRLCNPLNPFVSHKEIESVNNAVVMPAHGPA<br>KSMEYDAVATTHSWIPKRNRSILNTSQRGILEDEQMYQKCC<br>NLFEKFFPSSSYRRPIGISSMVEAMVSRARIDARIDFESGRIK<br>KEEFSEIMKICSTIEELRRQK<br>(underline = highly conserved;<br>bold = hypervariable) |

-continued

SEQUENCE LISTING TABLE

| SEQ ID NO | Description | Sequence |
|---|---|---|
| 179 | H3N2 PB2 Protein | MERIKELRNLMSQSRTREILTKTTVDHMAIIKKYTSGRQEKN<br>PSLRMKWMMAMKYPITADKRITEMVPERNEQGQTLWSK<br>MSDAGSDRVMVSPLAVTWWNRNGPVTSTVHYPKVYKTYF<br>DKVERLKHGTFGPVHFRNQVKIRRRVDINPGHADLSAKEA<br>QDVIMEVVFPNEVGARILTSESQLTITKEKKEELRDCKISPL<br>MVAYMLERELVRKTRFLPVAGGTSSIYIEVLHLTQGTCWEQ<br>MYTPGGGVRNDDVDQSLIIAARNIVRRAAVSADPLASLLEM<br>CHSTQIGGTRMVDILRQNPTEEQAVDICKAAMGLRISSSFSF<br>GGFTFKRTSGSSVKKEEEVLTGNLQTLRIRVHEGYEEFTMV<br>GKRATAILRKATRRLVQLIVSGRDEQSIAEAIIVAMVFSQED<br>CMIKAVRGDLNFVNRANQRLNPMHQLLRHFQKDAKVLFQ<br>NWGVEHIDSVMGMVGVLPDMTPSTEMSMRGIRVSKMGVD<br>EYSSTERVVVSIDRFLRVRDQRGNVLLSPEEVSETQGTERLT<br>ITYSSSMMWEINGPESVLVNTYQWIIRNWEAVKIQWSQNPA<br>MLYNKMEFEPFQSLVPKATRSQYSGFVRTLFQQMRDVLGT<br>FDTAQIIKLLPFAAAPPKQSRMQFSSLTVNVRGSGMRILVRG<br>NSPVFNYNKTTKRLTILGKDAGTLIEDPDESTSGVESAVLRG<br>FLIIGKEDRRYGPALSINELSNLAKGEKANVLIGQGDVVLV<br>MKRKRDSSILTDSQTATKRIRMAIN<br>(underline = highly conserved;<br>bold = hypervariable |
| 180 | Influenza B bm2 Protein | MLEPFQILSICSFILSALHFMAWTIGHLNQIKRGVNMKIRIKG<br>PNKETINREVSILRHSYQKEIQAKEAMKEVLSDNMEVLSDHI<br>VIEGLSAEEIIKMGETVLEVEELH<br>(underline = highly conserved;<br>bold = hypervariable) |
| 181 | Influenza B bm1 Protein | MSLFGDTIAYLLSLTEDGEGKAELAEKLHCWFGGKEFDLDS<br>ALEWIKNKRCLTDIQKALIGASICFLKPKDQERKRRFITEPLS<br>GMGTTATKKKGLILAERKMRKCVSFHEAFEIAEGHESSALL<br>YCLMVMYLNPGNYSMQVKLGTLCALCEKQASHSHRAHSR<br>AARSSVPGVRREMQMVSAMNTAKTMNGMGKGEDVQKLA<br>EELQSNIGVLRSLGASQKNGEGIAKDVMEVLKQSSMGNSAL<br>VKKYL<br>(underline = highly conserved;<br>bold = hypervariable) |
| 182 | Influenza B nep Protein | MADNMTTTQIEWRMKKMAIGSSIHSSSVLMKDIQSQFEQL<br>KLRWESYPNLVKSTDYHQKRETIRLVTEELYLLSKRIDDNIL<br>FHKTVIANSSIIADMVVSLSLLETLYEMKDVVEVYSRQCL<br>(underline = highly conserved;<br>bold = hypervariable) |
| 183 | Influenza B ns1 Protein | MADNMTTTQIEVGPGATNATINFEAGILECYERLSWQRALD<br>YPGQDRLNRLKRKLESRIKTHNKSEPESKRMSLEERKAIGV<br>KMMKVLLFMNPSAGIEGFEPYCMKSSSNSNCPKYNWTDYP<br>STPGRCLDDIEEEPDDVDGPTEIVLRDMNNKDARQKIKEEV<br>NTQKEGKFRLTIKRDMRNVLSLRVLVNGTFLKHPNGYKSLS<br>TLHRLNAYDQSGRLVAKLVATDDLTVEDEEDGHRILNSLFE<br>RLNEGHSKPIRAAETAVGVLSQFGQEHRLSPEEGDN<br>(underline = highly conserved;<br>bold = hypervariable) |
| 184 | Influenza B ns2 Protein | MADNMTTTQIEVVRMKKMAIGSSTHSSSVLMKDIQSQFEQL<br>KLRWESYPNLVKSTDYHQKRETIRLVTEELYLLSKRIDDNIL<br>FHKTVIANSSIIADMVVSLSLLETLYEMKDVVEVYSRQCL<br>(underline = highly conserved;<br>bold = hypervariable) |
| 185 | Influenza B pa Protein | MDTFITRNFQTTIIQKAKNTMAEFSEDPELQPAMLFNICVHL<br>EVCYVISDMNFLDEEGKAYTALEGQGKEQNLRPQYEVIEG<br>MPRTIAVVMVQRSLAQEHGIETPKYLADLFDYKTKRFIEVGI<br>TKGLADDYFWKKKEKLGNSMELMIFSYNQDYSLSNESSLD<br>EEGKGRVLSRLTELQAELSLKNLWQVLIGEEDVEKGIDFKL<br>GQTISRLRDISVPAGFSNFEGMRSYIDNIDPKGAIERNLARMS<br>PLVSVTPKKLKWEDLRPIGPHIYNHELPEVPYNAFLLMSDEL<br>GLANMTEGKSKKPKTLAKECLEKYSTLRDQTDPILIMKSEK<br>ANENFLWKLWRDCVNTISNEEMSNELQKTNYAKWATGDG<br>LTYQKIMKEVAIDDETMCQEEPKIPNKCRVAAWVQTEMNL<br>LSTLTSKRALDLPEIGPDVAPVEHVGSERRKYFVNEINYCKA<br>STVMMKYVLFHTSLLNESNASMGKYKVIPITNRVVNEKGES |

-continued

SEQUENCE LISTING TABLE

| SEQ ID NO | Description | Sequence |
|---|---|---|
| | | FDMLYGLAVKGQSHLRGDTDVVTVVTFEFSSTDPRVDSGK<br>WPKYTVFRIGSLFVSGREKSVYLYCRVNGTNKIQMKWGME<br>ARRCLLQSMQQMEAIVEQESSIQGYDMTKACFKGDRVNSP<br>KTFSIGTQEGKLVKGSFGKALRVIFTKCLMHYVFGNAQLEG<br>FSAESRRLLLLIQALKDRKGPWVFDLEGMYSGIEECISNNPW<br>VIQSAYWFNEWLGFEKEGSKVLESVDEIMDE<br>(underline = highly conserved;<br>bold = hypervariable) |
| 186 | Influenza B pb1 Protein | MNINPYFLFIDVPIQAAISTTFPYTGVPPYSHGTGTGYTIDTVI<br>RTHEYSNKGKQYVSDITGCTMVDPTNGPLPEDNEPSAYAQL<br>DCVLEALDRMDEEHPGLFQAASQNAMEALMVTTVDKLTQ<br>GRQTFDWTVCRNQPAATALNTTITSFRLNDLNGADKGGLV<br>PFCQDIIDSLDKPEMTFFSVKNIKKKLPAKNRKGFLIKRIPMK<br>VKDRISRVEYIKRALSLNTMTKDAERGKLKRRAIATAGIQIR<br>GFVLVVENLAKNICENLEQSGLPVGGNEKKAKLSNAVAKM<br>LSNCPPGGISMTVTGDNTKWNECLNPRIFLAMTERITRDSPI<br>WFRDFCSIAPVLFSNKIARLGKGFMITSKTKRLKAQIPCPDLF<br>SIPLERYNEETRAKLKKLKPFFNEEGTASLSPGMMMGMFN<br>MLSTVLGVAALGIKNIGNKEYLWDGLQSSDDFALFVNAKD<br>EETCMEGINDFYRTCKLLGINMSKKKSYCNETGMFEFTSMF<br>YRDGFVSNFAMEIPSFGVAGVNESADMAIGMTIIKNNMINN<br>GMGPATAQTAIQLFIADYRYTYKCHRGDSKVEGKRMKIIKE<br>LWENTKGRDGLLVADGGPNIYNLRNLHIPEIVLKYNLMDPE<br>YKGRLLHPQNPFVGHLSIEGIKEADITPAHGPVKKMDYDAV<br>SGTHSWRTKRNRSILNTDQRNMIEEEQCYAKCCNLFEACFN<br>SASYRKPVGQHSMLEAMAHRLRMDARLDYESGRMSKDDF<br>EKAMAHLGEIGYT<br>(underline = highly conserved;<br>bold = hypervariable) |
| 187 | Influenza B pb2 Protein | MTLAKIELLKQLLRDNEAKTVLKQTTVDQYNIIRKFNTSRIE<br>KNPSLRMKWAMCSNFPLALTKGDMANRIPLEYKGIQLKTN<br>AEDIGTKGQMCSIAAVTWWNTYGPIGDTEGFEKVYESFFLR<br>KMRLDNATWGRITFGPVERVRKRVLLNPLTKEMPPDEASN<br>VIMEILFPKEAGIPRESTWIHRELIKEKREKLKGTMITPIVLAY<br>MLERELVARRRFLPVAGATSAEFIEMLHCLQGENWRQIYHP<br>GGNKLTESRSQSMIVACRKIIRRSIVASNPLELAVEIANKTVI<br>DTEPLKSCLTAIDGGDVACDIIRAALGLKIRQRQRFGRLELK<br>RISGRGFKNDEEILIGNGTIQKIGIWDGEEEFHVRCGECRGIL<br>KKSKMRMEKLLINSAKKEDMKDLIILCMVFSQDTRMFQGV<br>RGEINFLNRAGQLLSPMYQLQRYFLSRSNDLFDQWGYEESP<br>KASELHGINELMNASDYTLKGVVVTKNVIDDFSSTETEKVS<br>ITKNLSLIKRTGEVIMGANDVSELESQAQLMITYDTPKMWE<br>MGTTKELVQNTYQWVLKNLVTEKAQFLLGKEDMFQWDAF<br>EAFESIIPQKMAGQYSGFARAVLKQMRDQEVMKTDQFIKLL<br>PFCFSPPKLRSNGEPYQFLRLVLKGGGENFIEVRKGSPLFSY<br>NPQTEVLTICGRMMSLKGKIEDEERNRSMGNAVLAGFLVSG<br>KYDPDLGDFKTIEELEKLKPGEKANILLYQGKPVKVVKRKR<br>YSALSNDISQGIKRQRMTVESMGWALS<br>(underline = highly conserved;<br>bold = hypervariable) |
| 188 | H1N1 M Protein | MSLLTEVETYVLSIIPSGPLKAEIAQRLESVFAGKNTDLEAL<br>MEWLKTRPILSPLTKGILGFVFTLTVPSERGLQRRRFIQNAL<br>NGNGDPNNMDRAVKLYKKLKREITFHGAKEVSLSYSTGAL<br>ASCMGLIYNRMGTVTTEAAFGLVCATCEQIADSQHRSHRQ<br>MATTTNPLIRHENRMVLASTTAKAMEQVAGSSEQAAEAME<br>VANQTRQMVHAMRTIGTHPSSSAGLRDDLLENLQAYQKR<br>MGVQMQRFK<br>(underline = highly conserved;<br>bold = hypervariable) |
| 189 | H1N1 ns1 Protein | MDSNTMSSFQVDCFLWHIRKRFADNGLGDAPFLDRLRRDQ<br>KSLKGRGNTLGLDIETATLVGKQIVEWILKEESSETLRMTI<br>ASVPTSRYLSDMTLEEMSRDWFMLMPRQKIIGPLCVRLDQ<br>AIMEKNIVLKANFSVIFNRLETLILLRAFTEEGAIVGEISP<br>LPSLPGHTYEDVKNAVGVLIGGLEWNGNTVRVSENIQRFA<br>WRNCDENGRPSLPPEQK<br>(underline = highly conserved;<br>bold = hypervariable) |

-continued

SEQUENCE LISTING TABLE

| SEQ ID NO | Description | Sequence |
|---|---|---|
| 190 | H1N1 pa Protein | MEGFVRQCFNPMI**V**ELAEKAMKEYGED**P**KIETNKFAAICTH<br>LEVCFMYSDFHFI**DER**GESIIVES**G**DPNALLKHRFEIIEGRDR**I**<br>MAWTVVNSICNTTG**V**EKPKFLPDLYDYKENRFIEIGVTRRE<br>VHIYYLEKANKIKSEKTHIHIFSFTGEEMATKADYTLDEESR<br>ARIKTRLFTIRQEMASRSLWDSFRQSERGEETIEE**K**FEI**T**GTM<br>R**K**LADQSLPPNFSS**L**ENFRAYVDGFEPNG**C**IEGKLSQMSKE<br>VNA**K**IEPFL**RT**TPRP**LR**LP**D**GP**L**C**H**QRSKFLLMD**A**LKLSIED<br>P**S**HEGEGIPLYDAIKCM**K**TFFGWKEP**NIV**KPHEKG**I**NPNYL<br>**MT**WKQVL**A**ELQDI**E**NEEKIP**R**TKNMK**R**TSQLKWALGENM<br>APEKVDF**D**DCKD**VG**DLKQYDSDEPE**P**RS**LA**SW**V**Q**N**EFNKA<br>CELTDSSWIELDEIGEDVAPIEHIASMRRNYFTAEVSHCRAT<br>EYIMKGVYINTALLNASCAAMDDFQLIPMISKCRTKEGRRK<br>TNLYGFI**I**KGRSHLRNDTDVVNFVSMEFSLTDPRLEPHKWE<br>KYCVLEIGDM**L**LR**T**AIGQVSRPMFLYVRTNGTSKIKMKWG<br>MEMRRCLLQSLQQIESMIEAESSVKEKDMTKEFFENKSETW<br>PIGESPRGVEEGSIGKVCRTLLAKSVFNSLYASPQLEGFSAES<br>RKLLLIVQALRDNLEPGTFDLGGLYEAIEECLINDPWVLLNA<br>SWFNSFLTHALK<br>(underline = highly conserved;<br>bold = hypervariable) |
| 191 | H1N1 pb1 Protein | MDVNPTLLFLKIPAQNAISTTFPYTGDPPYSHGTGTGYTMDT<br>VNRTHQYSEKGKWTTNTETGAPQLNPIDGPLPEDNEPSGYA<br>QTDCVLEAMAFLEESHPGIFENSCLETMEVVQQTRVDKLTQ<br>GRQTYDWTLNRNQPAATALANTIEVFRSNGLTANESGRLID<br>FLKDVMESMNKEEIEITTHFQRKRRVRDNMTKKMVTQRTI<br>GKKKQRLNKRGYLIRALTLNTMTKDAHRGKLKRRAIATPG<br>MQIRGFVYFVETLARSICEKLEQSGLPVGGNEKKAKLANVV<br>RKMMTNSQDTEISFTITGDNTKWNENQNPRMFLAMITYITR<br>NQPEWFRNILSMAPIMFSNKMARLGRGYMFESKRMKIRTQI<br>PAEMLASIDLKYFNESTKKKIEKIRPLLIDGTASLSPGMMMG<br>MFNMLSTVLGVSILNLGQKKYTKTIYWWDGLQSSDDFALI<br>VNAPNHEGIQAGVDRFYRTCKLVGINMSKKKSYINKTGTFE<br>FTSFFYRYGFVANFSMELPSFGVSGVNESADMSIGVTVIKNN<br>MINNDLGPATAQMALQLFIKDYRYTYRCHRGDTQIQTRRSF<br>ELKKLWDQTQSKVGLLVSDGGPNLYNIRNLHIPEVCLKWEL<br>MDDDYRGRLCNPLNPFVSHKEIDSVNNAVVMPAHGPAKSM<br>EYDAVATTHSWIPKRNRSILN<br>TSQRGILEDEQMYQKCCNLFEKFFPSSSYRRPVGISSMVEAM<br>VSRARIDARVDFESGRIKKEEFSEIMKICSTIEELRRQK<br>(underline = highly conserved;<br>bold = hypervariable) |
| 192 | H1N1 pb2 Protein | AMGLRISSSFSFGGFTFKRTSGSSVKREEEVLTGNLQTLKLT<br>VHEGYEEFTMVGKRATAILRKATRRLIQLIVSGRDEQSIVEA<br>IVVAMVFSQEDCMVKAVRGDLNFVNRANQRLNPMHQLLR<br>HFQKDAKVLFLNWGVEPIDNVMGMIGILPDMTPSTEMSMR<br>GVRVSKMGVDEYSNAERVVVSIDRFLRVRDQRGNVLLSPE<br>EVSETQGTEKLTITYSSSMMWEINGPESVLINTYQWIIRNWE<br>TVKIQWSQNPTMLYNKMEFEPFQSLVPKAIRGQYSGFVRTL<br>FQQMRDVLGTFDTTQIIKLLPFAAAPPKQSRMQFSSLTVNVR<br>GSGMKILVRGNSPVFNYNKTTKRLTVLGKDAGTLTEDPDE<br>GTAGVESAVLRGFLILGKEDRRYGPALSINELSNLAKGEKA<br>NVLIGQGDVVLVMKRKRDSSILTDSQTATKRIRMAIN<br>(underline = highly conserved;<br>bold = hypervariable) |
| 193 | H1N1 NS2 Protein | MD**SN**T**M**SSFQDIL**M**RMSKMQLGSSS**ED**LNGM**V**T**R**FESLK**I**<br>YRDSLGE**T**VMR**M**GDLH**Y**LQ**S**RN**E**KWREQL**G**QKFEEIRWLI<br>EE**M**RH**R**LK**A**TENSFEQITFMQALQLL**L**EVEQE**I**RAFSFQLI<br>(underline = highly conserved;<br>bold = hypervariable) |

The invention claimed is:

1. An immunogenic composition comprising one or more polypeptides comprising an amino acid sequence at least 80% identical to the amino acid sequence of SEQ ID NO:1, wherein the one or more polypeptides each comprise mutations to alanine or glycine at each of residues 159, 415, 419, 490, and 491 relative to the amino acid sequence of SEQ ID NO:1.

2. The immunogenic composition of claim 1, wherein the one or more polypeptides comprise an amino acid sequence at least 90% identical to the amino acid sequence of SEQ ID NO:1.

3. The immunogenic composition of claim 1, wherein the one or more polypeptides comprise an amino acid sequence at least 95% identical to the amino acid sequence of SEQ ID NO:1.

4. The immunogenic composition of claim 1, wherein the one or more polypeptides further comprise a mutation to alanine or glycine at one or more residue selected from the group consisting of 53, 114, 220, 275, and 277 relative to SEQ ID NO:1.

5. The immunogenic composition of claim 4, wherein the one or more polypeptides comprise a mutation to alanine or glycine at each residue selected from the group consisting of 53, 114, 220, 275, and 277 relative to SEQ ID NO:1.

6. The immunogenic composition of claim 4, wherein the one or more polypeptides further comprise a mutation to alanine or glycine at one or more residue selected from the group consisting of 147, 180, 225, 228, 300, and 319 relative to SEQ ID NO:1.

7. The immunogenic composition of claim 6, wherein the one or more polypeptides comprise a mutation to alanine or glycine at each residue selected from the group consisting of 147, 180, 225, 228, 300, and 319 relative to SEQ ID NO:1.

8. The immunogenic composition of claim 1, wherein the one or more polypeptides each comprise mutations to alanine at each of residues 159, 415, 419, 490, and 491 relative to the amino acid sequence of SEQ ID NO:1.

9. The immunogenic composition of claim 2, wherein the one or more polypeptides each comprise mutations to alanine at each of residues 159, 415, 419, 490, and 491 relative to the amino acid sequence of SEQ ID NO:1.

10. The immunogenic composition of claim 3, wherein the one or more polypeptides each comprise mutations to alanine at each of residues 159, 415, 419, 490, and 491 relative to the amino acid sequence of SEQ ID NO:1.

11. The immunogenic composition of claim 1, wherein the one or more polypeptides further comprise a mutation to alanine at one or more residue selected from the group consisting of 53, 114, 220, 275, and 277 relative to SEQ ID NO:1.

12. The immunogenic composition of claim 1, wherein the one or more polypeptides further comprise a mutation to alanine at each residue selected from the group consisting of 53, 114, 220, 275, and 277 relative to SEQ ID NO:1.

13. The immunogenic composition of claim 1, wherein the one or more polypeptides further comprise a mutation to alanine at one or more residue selected from the group consisting of 147, 180, 225, 228, 300, and 319 relative to SEQ ID NO:1.

14. The immunogenic composition of claim 1, wherein the one or more polypeptides further comprise a mutation to alanine at each residue selected from the group consisting of 147, 180, 225, 228, 300, and 319 relative to SEQ ID NO:1.

15. A method for immunizing a subject against infection with an influenza virus, inducing an immune response against influenza virus, or reducing an influenza virus infection in a subject in need thereof, comprising administering the immunogenic composition of claim 1.

16. A method for immunizing a subject against infection with an influenza virus, inducing an immune response against influenza virus, or reducing an influenza virus infection in a subject in need thereof, comprising administering the immunogenic composition of claim 2.

17. A method for immunizing a subject against infection with an influenza virus, inducing an immune response against influenza virus, or reducing an influenza virus infection in a subject in need thereof, comprising administering the immunogenic composition of claim 3.

18. A method for immunizing a subject against infection with an influenza virus, inducing an immune response against influenza virus, or reducing an influenza virus infection in a subject in need thereof, comprising administering the immunogenic composition of claim 4.

* * * * *

SEQUENCE LISTING

<160> NUMBER OF SEQ ID NOS: 194

<210> SEQ ID NO 1
<211> LENGTH: 566

```
<212> TYPE: PRT
<213> ORGANISM: Influenza A virus
<220> FEATURE:
<221> NAME/KEY: misc_feature
<222> LOCATION: (1)..(566)
<223> OTHER INFORMATION: H1N1 Hemagglutinin A/Michigan/45/2015 strain
      (amino acid) GenBank: MK622940.1

<400> SEQUENCE: 1

Met Lys Ala Ile Leu Val Val Leu Leu Tyr Thr Phe Thr Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Asn Ser Asp Asn Gly Thr Cys Tyr Pro Gly Asp Phe
            100                 105                 110

Ile Asn Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Asn Gln Ser Tyr Ile Asn Asp Lys Gly Lys Glu Val Leu Val
            180                 185                 190

Leu Trp Gly Ile His His Pro Ser Thr Thr Ala Asp Gln Gln Ser Leu
        195                 200                 205

Tyr Gln Asn Ala Asp Ala Tyr Val Phe Val Gly Thr Ser Arg Tyr Ser
    210                 215                 220

Lys Lys Phe Lys Pro Glu Ile Ala Thr Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Thr Met Glu Arg Asn Ala Gly Ser Gly Ile Ile Ile Ser Asp Thr Pro
        275                 280                 285

Val His Asp Cys Asn Thr Thr Cys Gln Thr Pro Glu Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365
```

-continued

His His Gln Asn Glu Gln Gly Ser Gly Tyr Ala Ala Asp Leu Lys Ser
    370                 375                 380

Thr Gln Asn Ala Ile Asp Lys Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Asn Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Lys Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 2
<211> LENGTH: 469
<212> TYPE: PRT
<213> ORGANISM: Influenza A virus
<220> FEATURE:
<221> NAME/KEY: misc_feature
<222> LOCATION: (1)..(469)
<223> OTHER INFORMATION: H1N1 Neuraminidase A/Michigan/45/2015 strain
      (amino acid) GenBank: MK622934.1

<400> SEQUENCE: 2

Met Asn Pro Asn Gln Lys Ile Ile Thr Ile Gly Ser Ile Cys Met Thr
1               5                   10                  15

Ile Gly Met Ala Asn Leu Ile Leu Gln Ile Gly Asn Ile Ile Ser Ile
            20                  25                  30

Trp Val Ser His Ser Ile Gln Ile Gly Asn Gln Ser Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145 150 155 160

Cys Pro Ile Gly Glu Val Pro Ser Pro Tyr Asn Ser Arg Phe Glu Ser
165 170 175

Val Ala Trp Ser Ala Ser Ala Cys His Asp Gly Ile Asn Trp Leu Thr
180 185 190

Ile Gly Ile Ser Gly Pro Asp Ser Gly Ala Val Ala Val Leu Lys Tyr
195 200 205

Asn Gly Ile Ile Thr Asp Thr Ile Lys Ser Trp Arg Asn Asn Ile Leu
210 215 220

Arg Thr Gln Glu Ser Glu Cys Ala Cys Val Asn Gly Ser Cys Phe Thr
225 230 235 240

Ile Met Thr Asp Gly Pro Ser Asp Gly Gln Ala Ser Tyr Lys Ile Phe
245 250 255

Arg Ile Glu Lys Gly Lys Ile Ile Lys Ser Val Glu Met Lys Ala Pro
260 265 270

Asn Tyr His Tyr Glu Glu Cys Ser Cys Tyr Pro Asp Ser Ser Glu Ile
275 280 285

Thr Cys Val Cys Arg Asp Asn Trp His Gly Ser Asn Arg Pro Trp Val
290 295 300

Ser Phe Asn Gln Asn Leu Glu Tyr Gln Met Gly Tyr Ile Cys Ser Gly
305 310 315 320

Val Phe Gly Asp Asn Pro Arg Pro Asn Asp Lys Thr Gly Ser Cys Gly
325 330 335

Pro Val Ser Ser Asn Gly Ala Asn Gly Val Lys Gly Phe Ser Phe Lys
340 345 350

Tyr Gly Asn Gly Val Trp Ile Gly Arg Thr Lys Ser Ile Ser Ser Arg
355 360 365

Lys Gly Phe Glu Met Ile Trp Asp Pro Asn Gly Trp Thr Gly Thr Asp
370 375 380

Asn Lys Phe Ser Ile Lys Gln Asp Ile Val Gly Ile Asn Glu Trp Ser
385 390 395 400

Gly Tyr Ser Gly Ser Phe Val Gln His Pro Glu Leu Thr Gly Leu Asp
405 410 415

Cys Ile Arg Pro Cys Phe Trp Val Glu Leu Ile Arg Gly Arg Pro Glu
420 425 430

Glu Asn Thr Ile Trp Thr Ser Gly Ser Ser Ile Ser Phe Cys Gly Val
435 440 445

Asn Ser Asp Thr Val Gly Trp Ser Trp Pro Asp Gly Ala Glu Leu Pro
450 455 460

Phe Thr Ile Asp Lys
465

<210> SEQ ID NO 3
<211> LENGTH: 570
<212> TYPE: PRT
<213> ORGANISM: Influenza A virus
<220> FEATURE:
<221> NAME/KEY: misc_feature
<222> LOCATION: (1)..(570)
<223> OTHER INFORMATION: H3N2 Hemagglutinin A/Mississippi/27/2013 strain
(amino acid) GenBank: AIK26600.1

<400> SEQUENCE: 3

Met Lys Thr Ile Ile Ala Leu Ser Tyr Ile Leu Cys Leu Val Phe Ala
1 5 10 15

-continued

```
Gln Lys Leu Pro Pro Tyr Gly Asn Ser Thr Ala Thr Leu Cys Leu Gly
            20                  25                  30

His His Ala Leu Pro Asn Gly Thr Ile Val Lys Thr Ile Thr Asn Asp
        35                  40                  45

Arg Ile Glu Val Thr Asn Ala Thr Glu Leu Val Gln Asn Ser Ser Ile
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Ser Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ser Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Lys Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
```

```
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asn Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Lys Gly Phe Ile Met Trp Ala Cys Gln Lys Gly Asn Ile
545                 550                 555                 560

Arg Cys Asn Ile Arg Cys Asn Ile Cys Ile
                565                 570


<210> SEQ ID NO 4
<211> LENGTH: 469
<212> TYPE: PRT
<213> ORGANISM: Influenza A virus
<220> FEATURE:
<221> NAME/KEY: misc_feature
<222> LOCATION: (1)..(469)
<223> OTHER INFORMATION: H3N2 Neuraminidase A/Miyagi/N1289/2005 strain
      (amino acid) GenBank: AB271522.1
<220> FEATURE:
<221> NAME/KEY: misc_feature
<222> LOCATION: (378)..(378)
<223> OTHER INFORMATION: Xaa can be any naturally occurring amino acid

<400> SEQUENCE: 4

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Lys Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asp Ile Val Arg Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190
```

```
Cys Val Thr Gly Asp Asp Lys Asn Ala Thr Ala Ser Phe Ile Tyr Asn
        195                 200                 205

Gly Arg Leu Val Asp Ser Ile Val Ser Trp Ser Lys Glu Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Leu Arg Ser Gly Tyr Glu Thr Phe Xaa Val Ile Glu Gly Trp Ser
    370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465
```

```
<210> SEQ ID NO 5
<211> LENGTH: 585
<212> TYPE: PRT
<213> ORGANISM: Influenza B virus
<220> FEATURE:
<221> NAME/KEY: misc_feature
<222> LOCATION: (1)..(585)
<223> OTHER INFORMATION: Influenza B Hemagglutinin B/Brisbane/60/2008
      strain (amino acid) GenBank: KX058884.1

<400> SEQUENCE: 5

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60
```

-continued

```
Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asp Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
```

```
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu Asn Asp Asp Gly Leu
    530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585


<210> SEQ ID NO 6
<211> LENGTH: 467
<212> TYPE: PRT
<213> ORGANISM: Influenza B virus
<220> FEATURE:
<221> NAME/KEY: misc_feature
<222> LOCATION: (1)..(467)
<223> OTHER INFORMATION: Influenza B Neuraminidase B/Wisconsin/05/2016
      strain (amino acid) GenBank: KX007164.1

<400> SEQUENCE: 6

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Pro Thr Glu Ile Thr Ala Pro
        35                  40                  45

Thr Met Pro Leu Asp Cys Ala Asn Ala Ser Asn Val Gln Ala Val Asn
    50                  55                  60

Arg Ser Ala Thr Lys Gly Val Thr Leu Leu Leu Leu Pro Glu Pro Glu
65                  70                  75                  80

Trp Thr Tyr Pro Arg Leu Ser Cys Pro Gly Ser Thr Phe Gln Lys Ala
                85                  90                  95

Leu Leu Ile Ser Pro His Arg Phe Gly Glu Thr Lys Gly Asn Ser Ala
            100                 105                 110

Pro Leu Ile Ile Arg Glu Pro Phe Val Ala Cys Gly Pro Asn Glu Cys
        115                 120                 125

Lys His Phe Ala Leu Thr His Tyr Ala Ala Gln Pro Gly Gly Tyr Tyr
    130                 135                 140

Asn Gly Thr Arg Gly Asp Arg Asn Lys Leu Arg His Leu Ile Ser Val
145                 150                 155                 160

Lys Leu Gly Lys Ile Pro Thr Val Glu Asn Ser Ile Phe His Met Ala
                165                 170                 175

Ala Trp Ser Gly Ser Ala Cys His Asp Gly Lys Glu Trp Thr Tyr Ile
            180                 185                 190

Gly Val Asp Gly Pro Asp Asn Asn Ala Leu Leu Lys Val Lys Tyr Gly
        195                 200                 205

Glu Ala Tyr Thr Asp Thr Tyr His Ser Tyr Ala Asn Asn Ile Leu Arg
    210                 215                 220

Thr Gln Glu Ser Ala Cys Asn Cys Ile Gly Gly Asn Cys Tyr Leu Met
225                 230                 235                 240

Ile Thr Asp Gly Ser Ala Ser Gly Val Ser Glu Cys Arg Phe Leu Lys
```

-continued

```
                245                 250                 255

Ile Arg Glu Gly Arg Ile Ile Lys Glu Ile Phe Pro Thr Gly Arg Val
            260                 265                 270

Lys His Thr Glu Glu Cys Thr Cys Gly Phe Ala Ser Asn Lys Thr Ile
        275                 280                 285

Glu Cys Ala Cys Arg Asp Asn Arg Tyr Thr Ala Lys Arg Pro Phe Val
    290                 295                 300

Lys Leu Asn Val Glu Thr Asp Thr Ala Glu Ile Arg Leu Met Cys Thr
305                 310                 315                 320

Asp Thr Tyr Leu Asp Thr Pro Arg Pro Asn Asp Gly Ser Ile Thr Gly
                325                 330                 335

Pro Cys Glu Ser Asp Gly Asp Lys Gly Ser Gly Gly Ile Lys Gly Gly
            340                 345                 350

Phe Val His Gln Arg Met Lys Ser Lys Ile Gly Arg Trp Tyr Ser Arg
        355                 360                 365

Thr Met Ser Lys Thr Glu Arg Met Gly Met Gly Leu Tyr Val Lys Tyr
    370                 375                 380

Gly Gly Asp Pro Trp Ala Asp Ser Asp Ala Leu Ala Phe Ser Gly Val
385                 390                 395                 400

Met Val Ser Met Lys Glu Pro Gly Trp Tyr Ser Phe Gly Phe Glu Ile
                405                 410                 415

Lys Asp Lys Lys Cys Asp Val Pro Cys Ile Gly Ile Glu Met Val His
            420                 425                 430

Asp Gly Gly Lys Glu Thr Trp His Ser Ala Ala Thr Ala Ile Tyr Cys
        435                 440                 445

Leu Met Gly Ser Gly Gln Leu Leu Trp Asp Thr Val Thr Gly Val Asp
    450                 455                 460

Met Ala Leu
465


<210> SEQ ID NO 7
<211> LENGTH: 8
<212> TYPE: PRT
<213> ORGANISM: Influenza A virus
<220> FEATURE:
<221> NAME/KEY: misc_feature
<222> LOCATION: (1)..(8)
<223> OTHER INFORMATION: H1N1 Hemagglutinin conserved region (amino
      acid)

<400> SEQUENCE: 7

Gly Tyr His Ala Asn Asn Ser Thr
1               5


<210> SEQ ID NO 8
<211> LENGTH: 24
<212> TYPE: DNA
<213> ORGANISM: Influenza A virus
<220> FEATURE:
<221> NAME/KEY: misc_feature
<222> LOCATION: (1)..(24)
<223> OTHER INFORMATION: H1N1 Hemagglutinin conserved region (nucleic
      acid)

<400> SEQUENCE: 8

ggttatcatg cgaacaattc aaca                                            24


<210> SEQ ID NO 9
<211> LENGTH: 7
<212> TYPE: PRT
```

<213> ORGANISM: Influenza A virus
<220> FEATURE:
<221> NAME/KEY: misc_feature
<222> LOCATION: (1)..(7)
<223> OTHER INFORMATION: H1N1 Hemagglutinin conserved region (amino acid)

<400> SEQUENCE: 9

Asn Val Thr Val Thr His Ser
1 5

<210> SEQ ID NO 10
<211> LENGTH: 21
<212> TYPE: DNA
<213> ORGANISM: Influenza A virus
<220> FEATURE:
<221> NAME/KEY: misc_feature
<222> LOCATION: (1)..(21)
<223> OTHER INFORMATION: H1N1 Hemagglutinin conserved region (nucleic acid)

<400> SEQUENCE: 10
aatgtaacag taacacactc t 21

<210> SEQ ID NO 11
<211> LENGTH: 7
<212> TYPE: PRT
<213> ORGANISM: Influenza A virus
<220> FEATURE:
<221> NAME/KEY: misc_feature
<222> LOCATION: (1)..(7)
<223> OTHER INFORMATION: H1N1 Hemagglutinin conserved region (amino acid)

<400> SEQUENCE: 11

Ser Trp Ser Tyr Ile Val Glu
1 5

<210> SEQ ID NO 12
<211> LENGTH: 21
<212> TYPE: DNA
<213> ORGANISM: Influenza A virus
<220> FEATURE:
<221> NAME/KEY: misc_feature
<222> LOCATION: (1)..(21)
<223> OTHER INFORMATION: H1N1 Hemagglutinin conserved region (nucleic acid)

<400> SEQUENCE: 12
tcatggtcct acattgtgga a 21

<210> SEQ ID NO 13
<211> LENGTH: 12
<212> TYPE: PRT
<213> ORGANISM: Influenza A virus
<220> FEATURE:
<221> NAME/KEY: misc_feature
<222> LOCATION: (1)..(12)
<223> OTHER INFORMATION: H1N1 Hemagglutinin conserved region (amino acid)

<400> SEQUENCE: 13

Gln Ser Arg Gly Leu Phe Gly Ala Ile Ala Gly Phe
1 5 10

<210> SEQ ID NO 14
<211> LENGTH: 36
<212> TYPE: DNA
<213> ORGANISM: Influenza A virus
<220> FEATURE:
<221> NAME/KEY: misc_feature
<222> LOCATION: (1)..(36)
<223> OTHER INFORMATION: H1N1 Hemagglutinin conserved region (nucleic acid)

<400> SEQUENCE: 14
caatctagag gcctattcgg ggccattgcc ggcttc 36

<210> SEQ ID NO 15
<211> LENGTH: 8
<212> TYPE: PRT
<213> ORGANISM: Influenza A virus
<220> FEATURE:
<221> NAME/KEY: misc_feature
<222> LOCATION: (1)..(8)
<223> OTHER INFORMATION: H1N1 Hemagglutinin conserved region (amino acid)

<400> SEQUENCE: 15

Gln Gly Ser Gly Tyr Ala Ala Asp
1 5

<210> SEQ ID NO 16
<211> LENGTH: 24
<212> TYPE: DNA
<213> ORGANISM: Influenza A virus
<220> FEATURE:
<221> NAME/KEY: misc_feature
<222> LOCATION: (1)..(24)
<223> OTHER INFORMATION: H1N1 Hemagglutinin conserved region (nucleic acid)

<400> SEQUENCE: 16
caggggtcag gatatgcagc cgac 24

<210> SEQ ID NO 17
<211> LENGTH: 7
<212> TYPE: PRT
<213> ORGANISM: Influenza A virus
<220> FEATURE:
<221> NAME/KEY: misc_feature
<222> LOCATION: (1)..(7)
<223> OTHER INFORMATION: H1N1 Hemagglutinin conserved region (amino acid)

<400> SEQUENCE: 17

Ile Thr Asn Lys Val Asn Ser
1 5

<210> SEQ ID NO 18
<211> LENGTH: 21
<212> TYPE: DNA
<213> ORGANISM: Influenza A virus
<220> FEATURE:
<221> NAME/KEY: misc_feature
<222> LOCATION: (1)..(21)
<223> OTHER INFORMATION: H1N1 Hemagglutinin conserved region (nucleic acid)

<400> SEQUENCE: 18
attactaaca aagtaaattc t 21

<210> SEQ ID NO 19
<211> LENGTH: 8
<212> TYPE: PRT
<213> ORGANISM: Influenza A virus
<220> FEATURE:
<221> NAME/KEY: misc_feature -continued
<222> LOCATION: (1)..(8)
<223> OTHER INFORMATION: H1N1 Hemagglutinin conserved region (amino acid)

<400> SEQUENCE: 19

Trp Thr Tyr Asn Ala Glu Leu Leu
1 5

<210> SEQ ID NO 20
<211> LENGTH: 24
<212> TYPE: DNA
<213> ORGANISM: Influenza A virus
<220> FEATURE:
<221> NAME/KEY: misc_feature
<222> LOCATION: (1)..(24)
<223> OTHER INFORMATION: H1N1 Hemagglutinin conserved region (nucleic acid)

<400> SEQUENCE: 20
tggacttaca atgccgaact gttg 24

<210> SEQ ID NO 21
<211> LENGTH: 7
<212> TYPE: PRT
<213> ORGANISM: Influenza A virus
<220> FEATURE:
<221> NAME/KEY: misc_feature
<222> LOCATION: (1)..(7)
<223> OTHER INFORMATION: H1N1 Hemagglutinin conserved region (amino acid)

<400> SEQUENCE: 21

Gly Cys Phe Glu Phe Tyr His
1 5

<210> SEQ ID NO 22
<211> LENGTH: 21
<212> TYPE: DNA
<213> ORGANISM: Influenza A virus
<220> FEATURE:
<221> NAME/KEY: misc_feature
<222> LOCATION: (1)..(21)
<223> OTHER INFORMATION: H1N1 Hemagglutinin conserved region (nucleic acid)

<400> SEQUENCE: 22
gcctgctttg aattttacca c 21

<210> SEQ ID NO 23
<211> LENGTH: 6
<212> TYPE: PRT
<213> ORGANISM: Influenza A virus
<220> FEATURE:
<221> NAME/KEY: misc_feature
<222> LOCATION: (1)..(6)
<223> OTHER INFORMATION: H1N1 Hemagglutinin conserved region (amino acid)

<400> SEQUENCE: 23

Leu Gly Asn Pro Glu Cys
1 5

<210> SEQ ID NO 24
<211> LENGTH: 18
<212> TYPE: DNA
<213> ORGANISM: Influenza A virus
<220> FEATURE:
<221> NAME/KEY: misc_feature
<222> LOCATION: (1)..(18)

<223> OTHER INFORMATION: H1N1 Hemagglutinin conserved region (nucleic acid)

<400> SEQUENCE: 24
ctgggaaatc cagagtgt 18

<210> SEQ ID NO 25
<211> LENGTH: 6
<212> TYPE: PRT
<213> ORGANISM: Influenza A virus
<220> FEATURE:
<221> NAME/KEY: misc_feature
<222> LOCATION: (1)..(6)
<223> OTHER INFORMATION: H1N1 Hemagglutinin conserved region (amino acid)

<400> SEQUENCE: 25

Glu Gly Gly Trp Thr Gly
1 5

<210> SEQ ID NO 26
<211> LENGTH: 18
<212> TYPE: DNA
<213> ORGANISM: Influenza A virus
<220> FEATURE:
<221> NAME/KEY: misc_feature
<222> LOCATION: (1)..(18)
<223> OTHER INFORMATION: H1N1 Hemagglutinin conserved region (nucleic acid)

<400> SEQUENCE: 26 gaagggggt ggacaggg 18

<210> SEQ ID NO 27
<211> LENGTH: 6
<212> TYPE: PRT
<213> ORGANISM: Influenza A virus
<220> FEATURE:
<221> NAME/KEY: misc_feature
<222> LOCATION: (1)..(6)
<223> OTHER INFORMATION: H1N1 Hemagglutinin conserved region (amino acid)

<400> SEQUENCE: 27

Leu Leu Glu Asn Glu Arg
1 5

<210> SEQ ID NO 28
<211> LENGTH: 18
<212> TYPE: DNA
<213> ORGANISM: Influenza A virus
<220> FEATURE:
<221> NAME/KEY: misc_feature
<222> LOCATION: (1)..(18)
<223> OTHER INFORMATION: H1N1 Hemagglutinin conserved region (nucleic acid)

<400> SEQUENCE: 28
ctattggaaa atgaaaga 18

<210> SEQ ID NO 29
<211> LENGTH: 12
<212> TYPE: PRT
<213> ORGANISM: Influenza A virus
<220> FEATURE:
<221> NAME/KEY: misc_feature
<222> LOCATION: (1)..(12)
<223> OTHER INFORMATION: H1N1 Neuraminidase conserved region (amino acid)

<400> SEQUENCE: 29

Met Asn Pro Asn Gln Lys Ile Ile Thr Ile Gly Ser
1               5                   10

<210> SEQ ID NO 30
<211> LENGTH: 36
<212> TYPE: DNA
<213> ORGANISM: Influenza A virus
<220> FEATURE:
<221> NAME/KEY: misc_feature
<222> LOCATION: (1)..(36)
<223> OTHER INFORMATION: H1N1 Neuraminidase conserved region (nucleic acid)

<400> SEQUENCE: 30
atgaatccaa accaaaagat aataaccatt ggttcg 36

<210> SEQ ID NO 31
<211> LENGTH: 10
<212> TYPE: PRT
<213> ORGANISM: Influenza A virus
<220> FEATURE:
<221> NAME/KEY: misc_feature
<222> LOCATION: (1)..(10)
<223> OTHER INFORMATION: H1N1 Neuraminidase conserved region (amino acid)

<400> SEQUENCE: 31

Arg Ile Gly Ser Lys Gly Asp Val Phe Val
1               5                   10

<210> SEQ ID NO 32
<211> LENGTH: 30
<212> TYPE: DNA
<213> ORGANISM: Influenza A virus
<220> FEATURE:
<221> NAME/KEY: misc_feature
<222> LOCATION: (1)..(30)
<223> OTHER INFORMATION: H1N1 Neuraminidase conserved region (nucleic acid)

<400> SEQUENCE: 32
agaatcggtt ccaaggggga tgtgtttgtc 30

<210> SEQ ID NO 33
<211> LENGTH: 8
<212> TYPE: PRT
<213> ORGANISM: Influenza A virus
<220> FEATURE:
<221> NAME/KEY: misc_feature
<222> LOCATION: (1)..(8)
<223> OTHER INFORMATION: H1N1 Neuraminidase conserved region (amino acid)

<400> SEQUENCE: 33

Arg Glu Pro Phe Ile Ser Cys Ser
1               5

<210> SEQ ID NO 34
<211> LENGTH: 18
<212> TYPE: DNA
<213> ORGANISM: Influenza A virus
<220> FEATURE:
<221> NAME/KEY: misc_feature
<222> LOCATION: (1)..(18)
<223> OTHER INFORMATION: H1N1 Neuraminidase conserved region (nucleic acid)

-continued

<400> SEQUENCE: 34
agggaaccat tcatatca 18

<210> SEQ ID NO 35
<211> LENGTH: 18
<212> TYPE: PRT
<213> ORGANISM: Influenza A virus
<220> FEATURE:
<221> NAME/KEY: misc_feature
<222> LOCATION: (1)..(18)
<223> OTHER INFORMATION: H1N1 Neuraminidase conserved region (amino acid)

<400> SEQUENCE: 35

Thr Phe Phe Leu Thr Gln Gly Ala Leu Leu Asn Asp Lys His Ser Asn
1 5 10 15

Gly Thr

<210> SEQ ID NO 36
<211> LENGTH: 54
<212> TYPE: DNA
<213> ORGANISM: Influenza A virus
<220> FEATURE:
<221> NAME/KEY: misc_feature
<222> LOCATION: (1)..(54)
<223> OTHER INFORMATION: H1N1 Neuraminidase conserved region (nucleic acid)

<400> SEQUENCE: 36
accttcttct tgactcaagg ggccttgcta aatgacaaac attccaatgg aacc 54

<210> SEQ ID NO 37
<211> LENGTH: 7
<212> TYPE: PRT
<213> ORGANISM: Influenza A virus
<220> FEATURE:
<221> NAME/KEY: misc_feature
<222> LOCATION: (1)..(7)
<223> OTHER INFORMATION: H1N1 Neuraminidase conserved region (amino acid)

<400> SEQUENCE: 37

Lys Asp Arg Ser Pro Tyr Arg
1 5

<210> SEQ ID NO 38
<211> LENGTH: 21
<212> TYPE: DNA
<213> ORGANISM: Influenza A virus
<220> FEATURE:
<221> NAME/KEY: misc_feature
<222> LOCATION: (1)..(21)
<223> OTHER INFORMATION: H1N1 Neuraminidase conserved region (nucleic acid)

<400> SEQUENCE: 38
aaagacagga gcccataccg a 21

<210> SEQ ID NO 39
<211> LENGTH: 14
<212> TYPE: PRT
<213> ORGANISM: Influenza A virus
<220> FEATURE:
<221> NAME/KEY: misc_feature
<222> LOCATION: (1)..(14)
<223> OTHER INFORMATION: H1N1 Neuraminidase conserved region (amino acid)

<400> SEQUENCE: 39

Phe Glu Ser Val Ala Trp Ser Ala Ser Ala Cys His Asp Gly
1 5 10

<210> SEQ ID NO 40
<211> LENGTH: 42
<212> TYPE: DNA
<213> ORGANISM: Influenza A virus
<220> FEATURE:
<221> NAME/KEY: misc_feature
<222> LOCATION: (1)..(42)
<223> OTHER INFORMATION: H1N1 Neuraminidase conserved region (nucleic acid)

<400> SEQUENCE: 40
tttgagtcag tcgcttggtc agcaagtgct tgtcatgatg gc 42

<210> SEQ ID NO 41
<211> LENGTH: 10
<212> TYPE: PRT
<213> ORGANISM: Influenza A virus
<220> FEATURE:
<221> NAME/KEY: misc_feature
<222> LOCATION: (1)..(10)
<223> OTHER INFORMATION: H1N1 Neuraminidase conserved region (amino acid)

<400> SEQUENCE: 41

Trp Leu Thr Ile Gly Ile Ser Gly Pro Asp
1 5 10

<210> SEQ ID NO 42
<211> LENGTH: 30
<212> TYPE: DNA
<213> ORGANISM: Influenza A virus
<220> FEATURE:
<221> NAME/KEY: misc_feature
<222> LOCATION: (1)..(30)
<223> OTHER INFORMATION: H1N1 Neuraminidase conserved region (nucleic acid)

<400> SEQUENCE: 42
tggctaacaa ttggaatttc tggcccagac 30

<210> SEQ ID NO 43
<211> LENGTH: 9
<212> TYPE: PRT
<213> ORGANISM: Influenza A virus
<220> FEATURE:
<221> NAME/KEY: misc_feature
<222> LOCATION: (1)..(9)
<223> OTHER INFORMATION: H1N1 Neuraminidase conserved region (amino acid)

<400> SEQUENCE: 43

Ile Leu Arg Thr Gln Glu Ser Glu Cys
1 5

<210> SEQ ID NO 44
<211> LENGTH: 27
<212> TYPE: DNA
<213> ORGANISM: Influenza A virus
<220> FEATURE:
<221> NAME/KEY: misc_feature
<222> LOCATION: (1)..(27)
<223> OTHER INFORMATION: H1N1 Neuraminidase conserved region (nucleic acid)

<400> SEQUENCE: 44
atattgagaa cacaagagtc tgaatgt 27

<210> SEQ ID NO 45
<211> LENGTH: 9
<212> TYPE: PRT
<213> ORGANISM: Influenza A virus
<220> FEATURE:
<221> NAME/KEY: misc_feature
<222> LOCATION: (1)..(9)
<223> OTHER INFORMATION: H1N1 Neuraminidase conserved region (amino acid)

<400> SEQUENCE: 45

Tyr Glu Glu Cys Ser Cys Tyr Pro Asp
1 5

<210> SEQ ID NO 46
<211> LENGTH: 27
<212> TYPE: DNA
<213> ORGANISM: Influenza A virus
<220> FEATURE:
<221> NAME/KEY: misc_feature
<222> LOCATION: (1)..(27)
<223> OTHER INFORMATION: H1N1 Neuraminidase conserved region (nucleic acid)

<400> SEQUENCE: 46
tatgaggaat gctcctgtta ccctgat 27

<210> SEQ ID NO 47
<211> LENGTH: 21
<212> TYPE: PRT
<213> ORGANISM: Influenza A virus
<220> FEATURE:
<221> NAME/KEY: misc_feature
<222> LOCATION: (1)..(21)
<223> OTHER INFORMATION: H1N1 Neuraminidase conserved region (amino acid)

<400> SEQUENCE: 47

Cys Val Cys Arg Asp Asn Trp His Gly Ser Asn Arg Pro Trp Val Ser
1 5 10 15

Phe Asn Gln Asn Leu
20

<210> SEQ ID NO 48
<211> LENGTH: 63
<212> TYPE: DNA
<213> ORGANISM: Influenza A virus
<220> FEATURE:
<221> NAME/KEY: misc_feature
<222> LOCATION: (1)..(63)
<223> OTHER INFORMATION: H1N1 Neuraminidase conserved region (nucleic acid)

<400> SEQUENCE: 48
tgtgtgtgca gggataactg gcatggctcg aatcgaccgt gggtgtcttt caaccagaat 60
ctg 63

<210> SEQ ID NO 49
<211> LENGTH: 10
<212> TYPE: PRT
<213> ORGANISM: Influenza A virus
<220> FEATURE:
<221> NAME/KEY: misc_feature
<222> LOCATION: (1)..(10)
<223> OTHER INFORMATION: H1N1 Neuraminidase conserved region (amino acid)

<400> SEQUENCE: 49

Asn Gly Val Trp Ile Gly Arg Thr Lys Ser
1 5 10

<210> SEQ ID NO 50
<211> LENGTH: 30
<212> TYPE: DNA
<213> ORGANISM: Influenza A virus
<220> FEATURE:
<221> NAME/KEY: misc_feature
<222> LOCATION: (1)..(30)
<223> OTHER INFORMATION: H1N1 Neuraminidase conserved region (nucleic acid)

<400> SEQUENCE: 50
aatggtgttt ggatagggag aactaaaagc 30

<210> SEQ ID NO 51
<211> LENGTH: 12
<212> TYPE: PRT
<213> ORGANISM: Influenza A virus
<220> FEATURE:
<221> NAME/KEY: misc_feature
<222> LOCATION: (1)..(12)
<223> OTHER INFORMATION: H1N1 Neuraminidase conserved region (amino acid)

<400> SEQUENCE: 51

Gly Phe Glu Met Ile Trp Asp Pro Asn Gly Trp Thr
1 5 10

<210> SEQ ID NO 52
<211> LENGTH: 36
<212> TYPE: DNA
<213> ORGANISM: Influenza A virus
<220> FEATURE:
<221> NAME/KEY: misc_feature
<222> LOCATION: (1)..(36)
<223> OTHER INFORMATION: H1N1 Neuraminidase conserved region (nucleic acid)

<400> SEQUENCE: 52
ggttttgaga tgatttggga tccgaatgga tggact 36

<210> SEQ ID NO 53
<211> LENGTH: 17
<212> TYPE: PRT
<213> ORGANISM: Influenza A virus
<220> FEATURE:
<221> NAME/KEY: misc_feature
<222> LOCATION: (1)..(17)
<223> OTHER INFORMATION: H1N1 Neuraminidase conserved region (amino acid)

<400> SEQUENCE: 53

Trp Ser Gly Tyr Ser Gly Ser Phe Val Gln His Pro Glu Leu Thr Gly
1 5 10 15

Leu

<210> SEQ ID NO 54
<211> LENGTH: 51
<212> TYPE: DNA
<213> ORGANISM: Influenza A virus
<220> FEATURE:
<221> NAME/KEY: misc_feature
<222> LOCATION: (1)..(51)

<223> OTHER INFORMATION: H1N1 Neuraminidase conserved region (nucleic
acid)

<400> SEQUENCE: 54
tggtcagggt atagcgggag ttttgttcag catccagaac taacagggct g 51

<210> SEQ ID NO 55
<211> LENGTH: 8
<212> TYPE: PRT
<213> ORGANISM: Influenza A virus
<220> FEATURE:
<221> NAME/KEY: misc_feature
<222> LOCATION: (1)..(8)
<223> OTHER INFORMATION: H1N1 Neuraminidase conserved region (amino
acid)

<400> SEQUENCE: 55

Arg Pro Cys Phe Trp Val Glu Leu
1 5

<210> SEQ ID NO 56
<211> LENGTH: 24
<212> TYPE: DNA
<213> ORGANISM: Influenza A virus
<220> FEATURE:
<221> NAME/KEY: misc_feature
<222> LOCATION: (1)..(24)
<223> OTHER INFORMATION: H1N1 Neuraminidase conserved region (nucleic
acid)

<400> SEQUENCE: 56
agaccttgct tctgggttga acta 24

<210> SEQ ID NO 57
<211> LENGTH: 12
<212> TYPE: PRT
<213> ORGANISM: Influenza A virus
<220> FEATURE:
<221> NAME/KEY: misc_feature
<222> LOCATION: (1)..(12)
<223> OTHER INFORMATION: H1N1 Neuraminidase conserved region (amino
acid)

<400> SEQUENCE: 57

Trp Thr Ser Gly Ser Ser Ile Ser Phe Cys Gly Val
1 5 10

<210> SEQ ID NO 58
<211> LENGTH: 36
<212> TYPE: DNA
<213> ORGANISM: Influenza A virus
<220> FEATURE:
<221> NAME/KEY: misc_feature
<222> LOCATION: (1)..(36)
<223> OTHER INFORMATION: H1N1 Neuraminidase conserved region (nucleic
acid)

<400> SEQUENCE: 58
tggactagcg ggagcagcat atccttttgt ggtgta 36

<210> SEQ ID NO 59
<211> LENGTH: 11
<212> TYPE: PRT
<213> ORGANISM: Influenza A virus
<220> FEATURE:
<221> NAME/KEY: misc_feature
<222> LOCATION: (1)..(11)
<223> OTHER INFORMATION: H1N1 Neuraminidase conserved region (amino
acid)

<400> SEQUENCE: 59

Trp Ser Trp Pro Asp Gly Ala Glu Leu Pro Phe
1 5 10

<210> SEQ ID NO 60
<211> LENGTH: 33
<212> TYPE: DNA
<213> ORGANISM: Influenza A virus
<220> FEATURE:
<221> NAME/KEY: misc_feature
<222> LOCATION: (1)..(33)
<223> OTHER INFORMATION: H1N1 Neuraminidase conserved region (nucleic acid)

<400> SEQUENCE: 60
tggtcttggc cagacggtgc tgagttgcca ttt 33

<210> SEQ ID NO 61
<211> LENGTH: 7
<212> TYPE: PRT
<213> ORGANISM: Influenza A virus
<220> FEATURE:
<221> NAME/KEY: misc_feature
<222> LOCATION: (1)..(7)
<223> OTHER INFORMATION: H3N2 Hemagglutinin conserved region (amino acid)

<400> SEQUENCE: 61

Leu Cys Leu Gly His His Ala
1 5

<210> SEQ ID NO 62
<211> LENGTH: 24
<212> TYPE: DNA
<213> ORGANISM: Influenza A virus
<220> FEATURE:
<221> NAME/KEY: misc_feature
<222> LOCATION: (1)..(24)
<223> OTHER INFORMATION: H3N2 Hemagglutinin conserved region (nucleic acid)

<400> SEQUENCE: 62
ctgtgccttg ggcaccatgc atta 24

<210> SEQ ID NO 63
<211> LENGTH: 10
<212> TYPE: PRT
<213> ORGANISM: Influenza A virus
<220> FEATURE:
<221> NAME/KEY: misc_feature
<222> LOCATION: (1)..(10)
<223> OTHER INFORMATION: H3N2 Hemagglutinin conserved region (amino acid)

<400> SEQUENCE: 63

Gly Asn Leu Ile Ala Pro Arg Gly Tyr Phe
1 5 10

<210> SEQ ID NO 64
<211> LENGTH: 30
<212> TYPE: DNA
<213> ORGANISM: Influenza A virus
<220> FEATURE:
<221> NAME/KEY: misc_feature
<222> LOCATION: (1)..(30)
<223> OTHER INFORMATION: H3N2 Hemagglutinin conserved region (nucleic acid)

-continued

<400> SEQUENCE: 64
gggaatctaa ttgctcctag gggttacttc 30

<210> SEQ ID NO 65
<211> LENGTH: 9
<212> TYPE: PRT
<213> ORGANISM: Influenza A virus
<220> FEATURE:
<221> NAME/KEY: misc_feature
<222> LOCATION: (1)..(9)
<223> OTHER INFORMATION: H3N2 Hemagglutinin conserved region (amino acid)

<400> SEQUENCE: 65

Leu Lys Leu Ala Thr Gly Met Arg Asn
1 5

<210> SEQ ID NO 66
<211> LENGTH: 27
<212> TYPE: DNA
<213> ORGANISM: Influenza A virus
<220> FEATURE:
<221> NAME/KEY: misc_feature
<222> LOCATION: (1)..(27)
<223> OTHER INFORMATION: H3N2 Hemagglutinin conserved region (nucleic acid)

<400> SEQUENCE: 66
ctgaaattgg caacaggaat gcgaaat 27

<210> SEQ ID NO 67
<211> LENGTH: 14
<212> TYPE: PRT
<213> ORGANISM: Influenza A virus
<220> FEATURE:
<221> NAME/KEY: misc_feature
<222> LOCATION: (1)..(14)
<223> OTHER INFORMATION: H3N2 Hemagglutinin conserved region (amino acid)

<400> SEQUENCE: 67

Phe Gly Ala Ile Ala Gly Phe Ile Glu Asn Gly Trp Glu Gly
1 5 10

<210> SEQ ID NO 68
<211> LENGTH: 42
<212> TYPE: DNA
<213> ORGANISM: Influenza A virus
<220> FEATURE:
<221> NAME/KEY: misc_feature
<222> LOCATION: (1)..(42)
<223> OTHER INFORMATION: H3N2 Hemagglutinin conserved region (nucleic acid)

<400> SEQUENCE: 68
tttggcgcaa tagcaggttt catagaaaat ggttgggagg gg 42

<210> SEQ ID NO 69
<211> LENGTH: 9
<212> TYPE: PRT
<213> ORGANISM: Influenza A virus
<220> FEATURE:
<221> NAME/KEY: misc_feature
<222> LOCATION: (1)..(9)
<223> OTHER INFORMATION: H3N2 Hemagglutinin conserved region (amino acid)

<400> SEQUENCE: 69

Lys Phe His Gln Ile Glu Lys Glu Phe
1 5

<210> SEQ ID NO 70
<211> LENGTH: 27
<212> TYPE: DNA
<213> ORGANISM: Influenza A virus
<220> FEATURE:
<221> NAME/KEY: misc_feature
<222> LOCATION: (1)..(27)
<223> OTHER INFORMATION: H3N2 Hemagglutinin conserved region (nucleic acid)

<400> SEQUENCE: 70
aaattccatc agattgaaaa agaattc 27

<210> SEQ ID NO 71
<211> LENGTH: 7
<212> TYPE: PRT
<213> ORGANISM: Influenza A virus
<220> FEATURE:
<221> NAME/KEY: misc_feature
<222> LOCATION: (1)..(7)
<223> OTHER INFORMATION: H3N2 Hemagglutinin conserved region (amino acid)

<400> SEQUENCE: 71

Asp Leu Thr Asp Ser Glu Met
1 5

<210> SEQ ID NO 72
<211> LENGTH: 21
<212> TYPE: DNA
<213> ORGANISM: Influenza A virus
<220> FEATURE:
<221> NAME/KEY: misc_feature
<222> LOCATION: (1)..(21)
<223> OTHER INFORMATION: H3N2 Hemagglutinin conserved region (nucleic acid)

<400> SEQUENCE: 72
gatctaactg actcagaaat g 21

<210> SEQ ID NO 73
<211> LENGTH: 7
<212> TYPE: PRT
<213> ORGANISM: Influenza A virus
<220> FEATURE:
<221> NAME/KEY: misc_feature
<222> LOCATION: (1)..(7)
<223> OTHER INFORMATION: H3N2 Hemagglutinin conserved region (amino acid)

<400> SEQUENCE: 73

Leu Arg Glu Asn Ala Glu Asp
1 5

<210> SEQ ID NO 74
<211> LENGTH: 21
<212> TYPE: DNA
<213> ORGANISM: Influenza A virus
<220> FEATURE:
<221> NAME/KEY: misc_feature
<222> LOCATION: (1)..(21)
<223> OTHER INFORMATION: H3N2 Hemagglutinin conserved region (nucleic acid)

<400> SEQUENCE: 74
ctgagggaaa atgctgagga t 21

<210> SEQ ID NO 75
<211> LENGTH: 9
<212> TYPE: PRT
<213> ORGANISM: Influenza A virus
<220> FEATURE:
<221> NAME/KEY: misc_feature
<222> LOCATION: (1)..(9)
<223> OTHER INFORMATION: H3N2 Neuraminidase conserved region (amino
acid)

<400> SEQUENCE: 75

Gln Phe Ala Leu Gly Gln Gly Thr Thr
1 5

<210> SEQ ID NO 76
<211> LENGTH: 27
<212> TYPE: DNA
<213> ORGANISM: Influenza A virus
<220> FEATURE:
<221> NAME/KEY: misc_feature
<222> LOCATION: (1)..(27)
<223> OTHER INFORMATION: H3N2 Neuraminidase conserved region (nucleic
acid)

<400> SEQUENCE: 76
caatttgccc ttggacaggg aacaaca 27

<210> SEQ ID NO 77
<211> LENGTH: 7
<212> TYPE: PRT
<213> ORGANISM: Influenza A virus
<220> FEATURE:
<221> NAME/KEY: misc_feature
<222> LOCATION: (1)..(7)
<223> OTHER INFORMATION: H3N2 Neuraminidase conserved region (amino
acid)

<400> SEQUENCE: 77

Ala Trp Ser Ser Ser Ser Cys
1 5

<210> SEQ ID NO 78
<211> LENGTH: 21
<212> TYPE: DNA
<213> ORGANISM: Influenza A virus
<220> FEATURE:
<221> NAME/KEY: misc_feature
<222> LOCATION: (1)..(21)
<223> OTHER INFORMATION: H3N2 Neuraminidase conserved region (nucleic
acid)

<400> SEQUENCE: 78
gcatggtcca gctcaagttg t 21

<210> SEQ ID NO 79
<211> LENGTH: 8
<212> TYPE: PRT
<213> ORGANISM: Influenza A virus
<220> FEATURE:
<221> NAME/KEY: misc_feature
<222> LOCATION: (1)..(8)
<223> OTHER INFORMATION: H3N2 Neuraminidase conserved region (amino
acid)

<400> SEQUENCE: 79

Leu Arg Thr Gln Glu Ser Glu Cys
1 5

<210> SEQ ID NO 80
<211> LENGTH: 24
<212> TYPE: DNA
<213> ORGANISM: Influenza A virus
<220> FEATURE:
<221> NAME/KEY: misc_feature
<222> LOCATION: (1)..(24)
<223> OTHER INFORMATION: H3N2 Neuraminidase conserved region (nucleic acid)

<400> SEQUENCE: 80
ctcaggaccc aggagtcaga atgc 24

<210> SEQ ID NO 81
<211> LENGTH: 7
<212> TYPE: PRT
<213> ORGANISM: Influenza A virus
<220> FEATURE:
<221> NAME/KEY: misc_feature
<222> LOCATION: (1)..(7)
<223> OTHER INFORMATION: H3N2 Neuraminidase conserved region (amino acid)

<400> SEQUENCE: 81

Glu Glu Cys Ser Cys Tyr Pro
1 5

<210> SEQ ID NO 82
<211> LENGTH: 21
<212> TYPE: DNA
<213> ORGANISM: Influenza A virus
<220> FEATURE:
<221> NAME/KEY: misc_feature
<222> LOCATION: (1)..(21)
<223> OTHER INFORMATION: H3N2 Neuraminidase conserved region (nucleic acid)

<400> SEQUENCE: 82
gaggagtgct cctgctatcc t 21

<210> SEQ ID NO 83
<211> LENGTH: 10
<212> TYPE: PRT
<213> ORGANISM: Influenza A virus
<220> FEATURE:
<221> NAME/KEY: misc_feature
<222> LOCATION: (1)..(10)
<223> OTHER INFORMATION: H3N2 Neuraminidase conserved region (amino acid)

<400> SEQUENCE: 83

Cys Ser Gly Leu Val Gly Asp Thr Pro Arg
1 5 10

<210> SEQ ID NO 84
<211> LENGTH: 30
<212> TYPE: DNA
<213> ORGANISM: Influenza A virus
<220> FEATURE:
<221> NAME/KEY: misc_feature
<222> LOCATION: (1)..(30)
<223> OTHER INFORMATION: H3N2 Neuraminidase conserved region (nucleic acid)

<400> SEQUENCE: 84
tgctcaggac ttgttggaga cacacccaga 30

<210> SEQ ID NO 85

<211> LENGTH: 8
<212> TYPE: PRT
<213> ORGANISM: Influenza A virus
<220> FEATURE:
<221> NAME/KEY: misc_feature
<222> LOCATION: (1)..(8)
<223> OTHER INFORMATION: H3N2 Neuraminidase conserved region (amino acid)

<400> SEQUENCE: 85

Gly Val Lys Gly Trp Ala Phe Asp
1 5

<210> SEQ ID NO 86
<211> LENGTH: 24
<212> TYPE: DNA
<213> ORGANISM: Influenza A virus
<220> FEATURE:
<221> NAME/KEY: misc_feature
<222> LOCATION: (1)..(24)
<223> OTHER INFORMATION: H3N2 Neuraminidase conserved region (nucleic acid)

<400> SEQUENCE: 86
ggagtgaaag gctgggcctt tgat 24

<210> SEQ ID NO 87
<211> LENGTH: 11
<212> TYPE: PRT
<213> ORGANISM: Influenza A virus
<220> FEATURE:
<221> NAME/KEY: misc_feature
<222> LOCATION: (1)..(11)
<223> OTHER INFORMATION: H3N2 Neuraminidase conserved region (amino acid)

<400> SEQUENCE: 87

Asn Arg Cys Phe Tyr Val Glu Leu Ile Arg Gly
1 5 10

<210> SEQ ID NO 88
<211> LENGTH: 33
<212> TYPE: DNA
<213> ORGANISM: Influenza A virus
<220> FEATURE:
<221> NAME/KEY: misc_feature
<222> LOCATION: (1)..(33)
<223> OTHER INFORMATION: H3N2 Neuraminidase conserved region (nucleic acid)

<400> SEQUENCE: 88
aatcggtgct tttatgtgga gttgataagg gga 33

<210> SEQ ID NO 89
<211> LENGTH: 10
<212> TYPE: PRT
<213> ORGANISM: Influenza A virus
<220> FEATURE:
<221> NAME/KEY: misc_feature
<222> LOCATION: (1)..(10)
<223> OTHER INFORMATION: H3N2 Neuraminidase conserved region (amino acid)

<400> SEQUENCE: 89

Val Phe Cys Gly Thr Ser Gly Thr Tyr Gly
1 5 10

<210> SEQ ID NO 90
<211> LENGTH: 30

<212> TYPE: DNA
<213> ORGANISM: Influenza A virus
<220> FEATURE:
<221> NAME/KEY: misc_feature
<222> LOCATION: (1)..(30)
<223> OTHER INFORMATION: H3N2 Neuraminidase conserved region (nucleic
acid)

<400> SEQUENCE: 90
gtgttttgtg gcacctcagg tacatatgga 30

<210> SEQ ID NO 91
<211> LENGTH: 7
<212> TYPE: PRT
<213> ORGANISM: Influenza A virus
<220> FEATURE:
<221> NAME/KEY: misc_feature
<222> LOCATION: (1)..(7)
<223> OTHER INFORMATION: H3N2 Neuraminidase conserved region (amino
acid)

<400> SEQUENCE: 91

Gly Ser Trp Pro Asp Gly Ala
1 5

<210> SEQ ID NO 92
<211> LENGTH: 21
<212> TYPE: DNA
<213> ORGANISM: Influenza A virus
<220> FEATURE:
<221> NAME/KEY: misc_feature
<222> LOCATION: (1)..(21)
<223> OTHER INFORMATION: H3N2 Neuraminidase conserved region (nucleic
acid)

<400> SEQUENCE: 92
ggctcatggc ctgatggggc g 21

<210> SEQ ID NO 93
<211> LENGTH: 13
<212> TYPE: PRT
<213> ORGANISM: Influenza B virus
<220> FEATURE:
<221> NAME/KEY: misc_feature
<222> LOCATION: (1)..(12)
<223> OTHER INFORMATION: Influenza B Hemagglutinin conserved region
(amino acid)

<400> SEQUENCE: 93

Val Lys Thr Ala Thr Gln Gly Glu Val Asn Val Thr Gly
1 5 10

<210> SEQ ID NO 94
<211> LENGTH: 39
<212> TYPE: DNA
<213> ORGANISM: Influenza B virus
<220> FEATURE:
<221> NAME/KEY: misc_feature
<222> LOCATION: (1)..(39)
<223> OTHER INFORMATION: Influenza B Hemagglutinin conserved region
(nucleic acid)

<400> SEQUENCE: 94
gtcaaaactg ctactcaagg ggaggtcaat gtgactggt 39

<210> SEQ ID NO 95
<211> LENGTH: 9
<212> TYPE: PRT
<213> ORGANISM: Influenza B virus
<220> FEATURE:
<221> NAME/KEY: misc_feature
<222> LOCATION: (1)..(9)
<223> OTHER INFORMATION: Influenza B Hemagglutinin conserved region
(amino acid)

<400> SEQUENCE: 95

Asn Cys Thr Asp Leu Asp Val Ala Leu
1 5

<210> SEQ ID NO 96
<211> LENGTH: 27
<212> TYPE: DNA
<213> ORGANISM: Influenza B virus
<220> FEATURE:
<221> NAME/KEY: misc_feature
<222> LOCATION: (1)..(27)
<223> OTHER INFORMATION: Influenza B Hemagglutinin conserved region
(nucleic acid)

<400> SEQUENCE: 96
aactgcacag atctggacgt agccttg 27

<210> SEQ ID NO 97
<211> LENGTH: 17
<212> TYPE: PRT
<213> ORGANISM: Influenza B virus
<220> FEATURE:
<221> NAME/KEY: misc_feature
<222> LOCATION: (1)..(17)
<223> OTHER INFORMATION: Influenza B Hemagglutinin conserved region
(amino acid)_

<400> SEQUENCE: 97

Thr Ser Gly Cys Phe Pro Ile Met His Asp Arg Thr Lys Ile Arg Gln
1 5 10 15

Leu

<210> SEQ ID NO 98
<211> LENGTH: 51
<212> TYPE: DNA
<213> ORGANISM: Influenza B virus
<220> FEATURE:
<221> NAME/KEY: misc_feature
<222> LOCATION: (1)..(51)
<223> OTHER INFORMATION: Influenza B Hemagglutinin conserved region
(nucleic acid)

<400> SEQUENCE: 98
acatctgggt gctttcctat aatgcacgac agaacaaaaa ttagacagct g 51

<210> SEQ ID NO 99
<211> LENGTH: 7
<212> TYPE: PRT
<213> ORGANISM: Influenza B virus
<220> FEATURE:
<221> NAME/KEY: misc_feature
<222> LOCATION: (1)..(7)
<223> OTHER INFORMATION: Influenza B Hemagglutinin conserved region
(amino acid)

<400> SEQUENCE: 99

Asn Leu Leu Arg Gly Tyr Glu
1 5

<210> SEQ ID NO 100
<211> LENGTH: 21
<212> TYPE: DNA

<213> ORGANISM: Influenza B virus
<220> FEATURE:
<221> NAME/KEY: misc_feature
<222> LOCATION: (1)..(21)
<223> OTHER INFORMATION: Influenza B Hemagglutinin conserved region
(nucleic acid)

<400> SEQUENCE: 100
aaccttctcc gaggatacga a 21

<210> SEQ ID NO 101
<211> LENGTH: 7
<212> TYPE: PRT
<213> ORGANISM: Influenza B virus
<220> FEATURE:
<221> NAME/KEY: misc_feature
<222> LOCATION: (1)..(7)
<223> OTHER INFORMATION: Influenza B Hemagglutinin conserved region
(amino acid)

<400> SEQUENCE: 101

Thr Met Ala Trp Ala Val Pro
1 5

<210> SEQ ID NO 102
<211> LENGTH: 21
<212> TYPE: DNA
<213> ORGANISM: Influenza B virus
<220> FEATURE:
<221> NAME/KEY: misc_feature
<222> LOCATION: (1)..(21)
<223> OTHER INFORMATION: Influenza B Hemagglutinin conserved region
(nucleic acid)

<400> SEQUENCE: 102
acaatggctt gggccgtccc a 21

<210> SEQ ID NO 103
<211> LENGTH: 16
<212> TYPE: PRT
<213> ORGANISM: Influenza B virus
<220> FEATURE:
<221> NAME/KEY: misc_feature
<222> LOCATION: (1)..(16)
<223> OTHER INFORMATION: Influenza B Hemagglutinin conserved region
(amino acid)

<400> SEQUENCE: 103

Glu Asp Gly Gly Leu Pro Gln Ser Gly Arg Ile Val Val Asp Tyr Met
1 5 10 15

<210> SEQ ID NO 104
<211> LENGTH: 48
<212> TYPE: DNA
<213> ORGANISM: Influenza B virus
<220> FEATURE:
<221> NAME/KEY: misc_feature
<222> LOCATION: (1)..(48)
<223> OTHER INFORMATION: Influenza B Hemagglutinin conserved region
(nucleic acid)

<400> SEQUENCE: 104
gaagacggag gactaccaca aagtggtaga attgttgttg attacatg 48

<210> SEQ ID NO 105
<211> LENGTH: 12
<212> TYPE: PRT
<213> ORGANISM: Influenza B virus
<220> FEATURE:

<221> NAME/KEY: misc_feature
<222> LOCATION: (1)..(12)
<223> OTHER INFORMATION: Influenza B Hemagglutinin conserved region
(amino acid)

<400> SEQUENCE: 105

Leu Pro Leu Ile Gly Glu Ala Asp Cys Leu His Glu
1 5 10

<210> SEQ ID NO 106
<211> LENGTH: 36
<212> TYPE: DNA
<213> ORGANISM: Influenza B virus
<220> FEATURE:
<221> NAME/KEY: misc_feature
<222> LOCATION: (1)..(36)
<223> OTHER INFORMATION: Influenza B Hemagglutinin conserved region
(nucleic acid)

<400> SEQUENCE: 106
ttgcctttaa ttggagaagc agattgcctc cacgaa 36

<210> SEQ ID NO 107
<211> LENGTH: 13
<212> TYPE: PRT
<213> ORGANISM: Influenza B virus
<220> FEATURE:
<221> NAME/KEY: misc_feature
<222> LOCATION: (1)..(13)
<223> OTHER INFORMATION: Influenza B Hemagglutinin conserved region
(amino acid)

<400> SEQUENCE: 107

Tyr Gly Gly Leu Asn Lys Ser Lys Pro Tyr Tyr Thr Gly
1 5 10

<210> SEQ ID NO 108
<211> LENGTH: 39
<212> TYPE: DNA
<213> ORGANISM: Influenza B virus
<220> FEATURE:
<221> NAME/KEY: misc_feature
<222> LOCATION: (1)..(39)
<223> OTHER INFORMATION: Influenza B Hemagglutinin conserved region
(nucleic acid)

<400> SEQUENCE: 108
tacggtggat taaacaaaag caagccttac tacacaggg 39

<210> SEQ ID NO 109
<211> LENGTH: 9
<212> TYPE: PRT
<213> ORGANISM: Influenza B virus
<220> FEATURE:
<221> NAME/KEY: misc_feature
<222> LOCATION: (1)..(9)
<223> OTHER INFORMATION: Influenza B Hemagglutinin conserved region
(amino acid)

<400> SEQUENCE: 109

Cys Pro Ile Trp Val Lys Thr Pro Leu
1 5

<210> SEQ ID NO 110
<211> LENGTH: 27
<212> TYPE: DNA
<213> ORGANISM: Influenza B virus
<220> FEATURE:
<221> NAME/KEY: misc_feature
<222> LOCATION: (1)..(27)
<223> OTHER INFORMATION: Influenza B Hemagglutinin conserved region
(nucleic acid)

<400> SEQUENCE: 110
tgcccaatat gggtgaaaac acccttg 27

<210> SEQ ID NO 111
<211> LENGTH: 17
<212> TYPE: PRT
<213> ORGANISM: Influenza B virus
<220> FEATURE:
<221> NAME/KEY: misc_feature
<222> LOCATION: (1)..(17)
<223> OTHER INFORMATION: Influenza B Hemagglutinin conserved region
(amino acid)

<400> SEQUENCE: 111

Gly Phe Phe Gly Ala Ile Ala Gly Phe Leu Glu Gly Gly Trp Glu Gly
1 5 10 15

Met

<210> SEQ ID NO 112
<211> LENGTH: 51
<212> TYPE: DNA
<213> ORGANISM: Influenza B virus
<220> FEATURE:
<221> NAME/KEY: misc_feature
<222> LOCATION: (1)..(51)
<223> OTHER INFORMATION: Influenza B Hemagglutinin conserved region
(nucleic acid)

<400> SEQUENCE: 112
ggtttcttcg gagctattgc tggtttctta gaaggaggat gggaaggaat g 51

<210> SEQ ID NO 113
<211> LENGTH: 13
<212> TYPE: PRT
<213> ORGANISM: Influenza B virus
<220> FEATURE:
<221> NAME/KEY: misc_feature
<222> LOCATION: (1)..(13)
<223> OTHER INFORMATION: Influenza B Hemagglutinin conserved region
(amino acid)

<400> SEQUENCE: 113

Ala Gly Trp His Gly Tyr Thr Ser His Gly Ala His Gly
1 5 10

<210> SEQ ID NO 114
<211> LENGTH: 39
<212> TYPE: DNA
<213> ORGANISM: Influenza B virus
<220> FEATURE:
<221> NAME/KEY: misc_feature
<222> LOCATION: (1)..(39)
<223> OTHER INFORMATION: Influenza B Hemagglutinin conserved region
(nucleic acid)

<400> SEQUENCE: 114
gcaggttggc acggatacac atcccatggg gcacatgga 39

<210> SEQ ID NO 115
<211> LENGTH: 12
<212> TYPE: PRT
<213> ORGANISM: Influenza B virus
<220> FEATURE:
<221> NAME/KEY: misc_feature
<222> LOCATION: (1)..(12)
<223> OTHER INFORMATION: Influenza B Hemagglutinin conserved region
(amino acid)

<400> SEQUENCE: 115

Ala Val Ala Ala Asp Leu Lys Ser Thr Gln Glu Ala
1 5 10

<210> SEQ ID NO 116
<211> LENGTH: 36
<212> TYPE: DNA
<213> ORGANISM: Influenza B virus
<220> FEATURE:
<221> NAME/KEY: misc_feature
<222> LOCATION: (1)..(36)
<223> OTHER INFORMATION: Influenza B Hemagglutinin conserved region
(nucleic acid)

<400> SEQUENCE: 116
gcggtggcag cagaccttaa gagcactcaa gaggcc 36

<210> SEQ ID NO 117
<211> LENGTH: 13
<212> TYPE: PRT
<213> ORGANISM: Influenza B virus
<220> FEATURE:
<221> NAME/KEY: misc_feature
<222> LOCATION: (1)..(13)
<223> OTHER INFORMATION: Influenza B Hemagglutinin conserved region
(amino acid)

<400> SEQUENCE: 117

Lys Ile Thr Lys Asn Leu Asn Ser Leu Ser Glu Leu Glu
1 5 10

<210> SEQ ID NO 118
<211> LENGTH: 39
<212> TYPE: DNA
<213> ORGANISM: Influenza B virus
<220> FEATURE:
<221> NAME/KEY: misc_feature
<222> LOCATION: (1)..(39)
<223> OTHER INFORMATION: Influenza B Hemagglutinin conserved region
(nucleic acid)

<400> SEQUENCE: 118
aagataacaa aaaatctcaa ctctttgagt gagctggaa 39

<210> SEQ ID NO 119
<211> LENGTH: 7
<212> TYPE: PRT
<213> ORGANISM: Influenza B virus
<220> FEATURE:
<221> NAME/KEY: misc_feature
<222> LOCATION: (1)..(7)
<223> OTHER INFORMATION: Influenza B Hemagglutinin conserved region
(amino acid)_

<400> SEQUENCE: 119

Lys Asn Leu Gln Arg Leu Ser
1 5

<210> SEQ ID NO 120
<211> LENGTH: 21
<212> TYPE: DNA
<213> ORGANISM: Influenza B virus
<220> FEATURE:
<221> NAME/KEY: misc_feature
<222> LOCATION: (1)..(21)

<223> OTHER INFORMATION: Influenza B Hemagglutinin conserved region
(nucleic acid)

<400> SEQUENCE: 120
aagaatcttc aaagactaag c 21

<210> SEQ ID NO 121
<211> LENGTH: 55
<212> TYPE: PRT
<213> ORGANISM: Influenza B virus
<220> FEATURE:
<221> NAME/KEY: misc_feature
<222> LOCATION: (1)..(55)
<223> OTHER INFORMATION: Influenza B Hemagglutinin conserved region
(amino acid)_

<400> SEQUENCE: 121

Glu Ile Leu Glu Leu Asp Glu Lys Val Asp Asp Leu Arg Ala Asp Thr
1 5 10 15

Ile Ser Ser Gln Ile Glu Leu Ala Val Leu Leu Ser Asn Glu Gly Ile
20 25 30

Ile Asn Ser Glu Asp Glu His Leu Leu Ala Leu Glu Arg Lys Leu Lys
35 40 45

Lys Met Leu Gly Pro Ser Ala
50 55

<210> SEQ ID NO 122
<211> LENGTH: 165
<212> TYPE: DNA
<213> ORGANISM: Influenza B virus
<220> FEATURE:
<221> NAME/KEY: misc_feature
<222> LOCATION: (1)..(165)
<223> OTHER INFORMATION: Influenza B Hemagglutinin conserved region
(nucleic acid)

<400> SEQUENCE: 122
gaaatactag aactagatga gaaagtggat gatctcagag ctgatacaat aagctcacaa 60
atagaactcg cagtcctgct ttccaatgaa ggaataataa acagtgaaga tgaacatctc 120
ttggcgcttg aaagaaagct gaagaaaatg ctgggcccct ctgct 165

<210> SEQ ID NO 123
<211> LENGTH: 18
<212> TYPE: PRT
<213> ORGANISM: Influenza B virus
<220> FEATURE:
<221> NAME/KEY: misc_feature
<222> LOCATION: (1)..(18)
<223> OTHER INFORMATION: Influenza B Hemagglutinin conserved region
(amino acid)_

<400> SEQUENCE: 123

Ile Gly Asn Gly Cys Phe Glu Thr Lys His Lys Cys Asn Gln Thr Cys
1 5 10 15

Leu Asp

<210> SEQ ID NO 124
<211> LENGTH: 54
<212> TYPE: DNA
<213> ORGANISM: Influenza B virus
<220> FEATURE:
<221> NAME/KEY: misc_feature
<222> LOCATION: (1)..(54)
<223> OTHER INFORMATION: Influenza B Hemagglutinin conserved region
(nucleic acid)

```
<400> SEQUENCE: 124

atagggaatg gatgctttga aaccaaacac aagtgcaacc agacctgtct cgac        54

<210> SEQ ID NO 125
<211> LENGTH: 19
<212> TYPE: PRT
<213> ORGANISM: Influenza B virus
<220> FEATURE:
<221> NAME/KEY: misc_feature
<222> LOCATION: (1)..(19)
<223> OTHER INFORMATION: Influenza B Hemagglutinin conserved region
      (amino acid)

<400> SEQUENCE: 125

Ala Gly Glu Phe Ser Leu Pro Thr Phe Asp Ser Leu Asn Ile Thr Ala
1               5                   10                  15

Ala Ser Leu

<210> SEQ ID NO 126
<211> LENGTH: 57
<212> TYPE: DNA
<213> ORGANISM: Influenza B virus
<220> FEATURE:
<221> NAME/KEY: misc_feature
<222> LOCATION: (1)..(57)
<223> OTHER INFORMATION: Influenza B Hemagglutinin conserved region
      (nucleic acid)

<400> SEQUENCE: 126

gcaggagaat tttctctccc cacctttgat tcactgaata ttactgctgc atcttta     57

<210> SEQ ID NO 127
<211> LENGTH: 19
<212> TYPE: PRT
<213> ORGANISM: Influenza B virus
<220> FEATURE:
<221> NAME/KEY: misc_feature
<222> LOCATION: (1)..(19)
<223> OTHER INFORMATION: Influenza B Hemagglutinin conserved region
      (amino acid)

<400> SEQUENCE: 127

His Thr Ile Leu Leu Tyr Tyr Ser Thr Ala Ala Ser Ser Leu Ala Val
1               5                   10                  15

Thr Leu Met

<210> SEQ ID NO 128
<211> LENGTH: 57
<212> TYPE: DNA
<213> ORGANISM: Influenza B virus
<220> FEATURE:
<221> NAME/KEY: misc_feature
<222> LOCATION: (1)..(57)
<223> OTHER INFORMATION: Influenza B Hemagglutinin conserved region
      (nucleic acid)

<400> SEQUENCE: 128

catactatac tgctttacta ctcaactgct gcctccagtt tggctgtaac actgatg     57

<210> SEQ ID NO 129
<211> LENGTH: 11
<212> TYPE: PRT
<213> ORGANISM: Influenza B virus
<220> FEATURE:
<221> NAME/KEY: misc_feature
<222> LOCATION: (1)..(11)
```

<223> OTHER INFORMATION: Influenza B Neuraminidase conserved region
(amino acid)

<400> SEQUENCE: 129

Ala Leu Leu Ile Ser Pro His Arg Phe Gly Glu
1 5 10

<210> SEQ ID NO 130
<211> LENGTH: 33
<212> TYPE: DNA
<213> ORGANISM: Influenza B virus
<220> FEATURE:
<221> NAME/KEY: misc_feature
<222> LOCATION: (1)..(33)
<223> OTHER INFORMATION: Influenza B Neuraminidase conserved region
(nucleic acid)

<400> SEQUENCE: 130
gcactcctaa ttagccctca tagattcgga gaa 33

<210> SEQ ID NO 131
<211> LENGTH: 12
<212> TYPE: PRT
<213> ORGANISM: Influenza B virus
<220> FEATURE:
<221> NAME/KEY: misc_feature
<222> LOCATION: (1)..(12)
<223> OTHER INFORMATION: Influenza B Neuraminidase conserved region
(amino acid)

<400> SEQUENCE: 131

His Phe Ala Leu Thr His Tyr Ala Ala Gln Pro Gly
1 5 10

<210> SEQ ID NO 132
<211> LENGTH: 36
<212> TYPE: DNA
<213> ORGANISM: Influenza B virus
<220> FEATURE:
<221> NAME/KEY: misc_feature
<222> LOCATION: (1)..(36)
<223> OTHER INFORMATION: Influenza B Neuraminidase conserved region
(nucleic acid)

<400> SEQUENCE: 132
cactttgctt taacccatta tgcagcccaa ccaggg 36

<210> SEQ ID NO 133
<211> LENGTH: 8
<212> TYPE: PRT
<213> ORGANISM: Influenza B virus
<220> FEATURE:
<221> NAME/KEY: misc_feature
<222> LOCATION: (1)..(8)
<223> OTHER INFORMATION: Influenza B Neuraminidase conserved region
(amino acid)

<400> SEQUENCE: 133

Asp Arg Asn Lys Leu Arg His Leu
1 5

<210> SEQ ID NO 134
<211> LENGTH: 24
<212> TYPE: DNA
<213> ORGANISM: Influenza B virus
<220> FEATURE:
<221> NAME/KEY: misc_feature
<222> LOCATION: (1)..(24)
<223> OTHER INFORMATION: Influenza B Neuraminidase conserved region (nucleic acid)

<400> SEQUENCE: 134
gacagaaaca agctgaggca tcta 24

<210> SEQ ID NO 135
<211> LENGTH: 10
<212> TYPE: PRT
<213> ORGANISM: Influenza B virus
<220> FEATURE:
<221> NAME/KEY: misc_feature
<222> LOCATION: (1)..(10)
<223> OTHER INFORMATION: Influenza B Neuraminidase conserved region (amino acid)

<400> SEQUENCE: 135

Ala Trp Ser Gly Ser Ala Cys His Asp Gly
1 5 10

<210> SEQ ID NO 136
<211> LENGTH: 30
<212> TYPE: DNA
<213> ORGANISM: Influenza B virus
<220> FEATURE:
<221> NAME/KEY: misc_feature
<222> LOCATION: (1)..(30)
<223> OTHER INFORMATION: Influenza B Neuraminidase conserved region (nucleic acid)

<400> SEQUENCE: 136
gcatggagcg ggtccgcgtg ccatgatggt 30

<210> SEQ ID NO 137
<211> LENGTH: 13
<212> TYPE: PRT
<213> ORGANISM: Influenza B virus
<220> FEATURE:
<221> NAME/KEY: misc_feature
<222> LOCATION: (1)..(13)
<223> OTHER INFORMATION: Influenza B Neuraminidase conserved region (amino acid)

<400> SEQUENCE: 137

Lys Tyr Gly Glu Ala Tyr Thr Asp Thr Tyr His Ser Tyr
1 5 10

<210> SEQ ID NO 138
<211> LENGTH: 39
<212> TYPE: DNA
<213> ORGANISM: Influenza B virus
<220> FEATURE:
<221> NAME/KEY: misc_feature
<222> LOCATION: (1)..(39)
<223> OTHER INFORMATION: Influenza B Neuraminidase conserved region (nucleic acid)

<400> SEQUENCE: 138
aaatatggag aagcatatac tgacacatac cattcctat 39

<210> SEQ ID NO 139
<211> LENGTH: 11
<212> TYPE: PRT
<213> ORGANISM: Influenza B virus
<220> FEATURE:
<221> NAME/KEY: misc_feature
<222> LOCATION: (1)..(11)
<223> OTHER INFORMATION: Influenza B Neuraminidase conserved region (amino acid)

<400> SEQUENCE: 139

Leu Arg Thr Gln Glu Ser Ala Cys Asn Cys Ile
1 5 10

<210> SEQ ID NO 140
<211> LENGTH: 33
<212> TYPE: DNA
<213> ORGANISM: Influenza B virus
<220> FEATURE:
<221> NAME/KEY: misc_feature
<222> LOCATION: (1)..(33)
<223> OTHER INFORMATION: Influenza B Neuraminidase conserved region (nucleic acid)

<400> SEQUENCE: 140
ctaagaacac aagaaagtgc ctgcaattgc atc 33

<210> SEQ ID NO 141
<211> LENGTH: 10
<212> TYPE: PRT
<213> ORGANISM: Influenza B virus
<220> FEATURE:
<221> NAME/KEY: misc_feature
<222> LOCATION: (1)..(10)
<223> OTHER INFORMATION: Influenza B Neuraminidase conserved region (amino acid)

<400> SEQUENCE: 141

Cys Arg Phe Leu Lys Ile Arg Glu Gly Arg
1 5 10

<210> SEQ ID NO 142
<211> LENGTH: 30
<212> TYPE: DNA
<213> ORGANISM: Influenza B virus
<220> FEATURE:
<221> NAME/KEY: misc_feature
<222> LOCATION: (1)..(30)
<223> OTHER INFORMATION: Influenza B Neuraminidase conserved region (nucleic acid)

<400> SEQUENCE: 142
tgcagatttc ttaagattcg agagggccga 30

<210> SEQ ID NO 143
<211> LENGTH: 10
<212> TYPE: PRT
<213> ORGANISM: Influenza B virus
<220> FEATURE:
<221> NAME/KEY: misc_feature
<222> LOCATION: (1)..(10)
<223> OTHER INFORMATION: Influenza B Neuraminidase conserved region (amino acid)

<400> SEQUENCE: 143

His Thr Glu Glu Cys Thr Cys Gly Phe Ala
1 5 10

<210> SEQ ID NO 144
<211> LENGTH: 30
<212> TYPE: DNA
<213> ORGANISM: Influenza B virus
<220> FEATURE:
<221> NAME/KEY: misc_feature
<222> LOCATION: (1)..(30)
<223> OTHER INFORMATION: Influenza B Neuraminidase conserved region (nucleic acid)

<400> SEQUENCE: 144
cacactgagg aatgcacatg cggatttgcc 30

<210> SEQ ID NO 145
<211> LENGTH: 10
<212> TYPE: PRT
<213> ORGANISM: Influenza B virus
<220> FEATURE:
<221> NAME/KEY: misc_feature
<222> LOCATION: (1)..(10)
<223> OTHER INFORMATION: Influenza B Neuraminidase conserved region (amino acid)

<400> SEQUENCE: 145

Tyr Thr Ala Lys Arg Pro Phe Val Lys Leu
1 5 10

<210> SEQ ID NO 146
<211> LENGTH: 30
<212> TYPE: DNA
<213> ORGANISM: Influenza B virus
<220> FEATURE:
<221> NAME/KEY: misc_feature
<222> LOCATION: (1)..(30)
<223> OTHER INFORMATION: Influenza B Neuraminidase conserved region (nucleic acid)

<400> SEQUENCE: 146
tacacagcaa aaagaccttt tgtcaaatta 30

<210> SEQ ID NO 147
<211> LENGTH: 8
<212> TYPE: PRT
<213> ORGANISM: Influenza B virus
<220> FEATURE:
<221> NAME/KEY: misc_feature
<222> LOCATION: (1)..(8)
<223> OTHER INFORMATION: Influenza B Neuraminidase conserved region (amino acid)

<400> SEQUENCE: 147

Lys Gly Gly Phe Val His Gln Arg
1 5

<210> SEQ ID NO 148
<211> LENGTH: 24
<212> TYPE: DNA
<213> ORGANISM: Influenza B virus
<220> FEATURE:
<221> NAME/KEY: misc_feature
<222> LOCATION: (1)..(24)
<223> OTHER INFORMATION: Influenza B Neuraminidase conserved region (nucleic acid)

<400> SEQUENCE: 148
aagggaggat ttgttcatca aaga 24

<210> SEQ ID NO 149
<211> LENGTH: 7
<212> TYPE: PRT
<213> ORGANISM: Influenza B virus
<220> FEATURE:
<221> NAME/KEY: misc_feature
<222> LOCATION: (1)..(7)
<223> OTHER INFORMATION: Influenza B Neuraminidase conserved region (amino acid)

<400> SEQUENCE: 149

Gly Arg Trp Tyr Ser Arg Thr 1 5

<210> SEQ ID NO 150
<211> LENGTH: 21
<212> TYPE: DNA
<213> ORGANISM: Influenza B virus
<220> FEATURE:
<221> NAME/KEY: misc_feature
<222> LOCATION: (1)..(21)
<223> OTHER INFORMATION: Influenza B Neuraminidase conserved region (nucleic acid)

<400> SEQUENCE: 150
ggaaggtggt actctcgaac g 21

<210> SEQ ID NO 151
<211> LENGTH: 10
<212> TYPE: PRT
<213> ORGANISM: Influenza B virus
<220> FEATURE:
<221> NAME/KEY: misc_feature
<222> LOCATION: (1)..(10)
<223> OTHER INFORMATION: Influenza B Neuraminidase conserved region (amino acid)

<400> SEQUENCE: 151

Glu Pro Gly Trp Tyr Ser Phe Gly Phe Glu
1 5 10

<210> SEQ ID NO 152
<211> LENGTH: 30
<212> TYPE: DNA
<213> ORGANISM: Influenza B virus
<220> FEATURE:
<221> NAME/KEY: misc_feature
<222> LOCATION: (1)..(30)
<223> OTHER INFORMATION: Influenza B Neuraminidase conserved region (nucleic acid)

<400> SEQUENCE: 152
gaacctggtt ggtattcctt tggcttcgaa 30

<210> SEQ ID NO 153
<211> LENGTH: 7
<212> TYPE: PRT
<213> ORGANISM: Influenza B virus
<220> FEATURE:
<221> NAME/KEY: misc_feature
<222> LOCATION: (1)..(7)
<223> OTHER INFORMATION: Influenza B Neuraminidase conserved region (amino acid)

<400> SEQUENCE: 153

Glu Met Val His Asp Gly Gly
1 5

<210> SEQ ID NO 154
<211> LENGTH: 21
<212> TYPE: DNA
<213> ORGANISM: Influenza B virus
<220> FEATURE:
<221> NAME/KEY: misc_feature
<222> LOCATION: (1)..(21)
<223> OTHER INFORMATION: Influenza B Neuraminidase conserved region (nucleic acid)

<400> SEQUENCE: 154
gagatggtac atgatggtgg a 21

<210> SEQ ID NO 155
<211> LENGTH: 8
<212> TYPE: PRT
<213> ORGANISM: Influenza A virus
<220> FEATURE:
<221> NAME/KEY: misc_feature
<222> LOCATION: (1)..(8)
<223> OTHER INFORMATION: H1N1 Neuraminidase conserved region (amino acid)

<400> SEQUENCE: 155

Gly Ala Val Ala Val Leu Lys Tyr
1 5

<210> SEQ ID NO 156
<211> LENGTH: 24
<212> TYPE: DNA
<213> ORGANISM: Influenza A virus
<220> FEATURE:
<221> NAME/KEY: misc_feature
<222> LOCATION: (1)..(24)
<223> OTHER INFORMATION: H1N1 Neuraminidase conserved region (nucleic acid)

<400> SEQUENCE: 156
ggggcagtgg ctgtgttaaa gtac 24

<210> SEQ ID NO 157
<211> LENGTH: 566
<212> TYPE: PRT
<213> ORGANISM: Influenza A virus
<220> FEATURE:
<221> NAME/KEY: misc_feature
<222> LOCATION: (1)..(566)
<223> OTHER INFORMATION: Variant of H1N1 Hemagglutinin A/Michigan/45/2015 strain (amino acid) GenBank: MK622940.1 Hypervariable residues substituted with Ala

<400> SEQUENCE: 157

Met Lys Ala Ile Leu Val Val Leu Leu Tyr Thr Phe Ala Ala Ala Asn
1 5 10 15

Ala Asp Thr Leu Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Ala Ala His Asn Gly Lys Leu Cys Lys Leu Arg Gly Val
50 55 60

Ala Pro Leu His Leu Gly Lys Cys Asn Ile Ala Gly Trp Ala Leu Gly
65 70 75 80

Asn Pro Glu Cys Glu Ala Leu Ala Thr Ala Ser Ser Trp Ser Tyr Ile
85 90 95

Val Glu Thr Ser Ala Ser Asp Asn Gly Thr Cys Tyr Pro Gly Asp Phe
100 105 110

Ile Ala Tyr Glu Glu Leu Arg Glu Gln Leu Ser Ser Val Ser Ser Phe
115 120 125

Glu Arg Phe Glu Ile Phe Pro Lys Ala Ser Ser Trp Pro Asn His Asp
130 135 140

Ala Asn Ala Gly Val Thr Ala Ala Cys Pro Ala Ala Gly Ala Ala Ala
145 150 155 160

Phe Tyr Ala Asn Leu Ile Trp Leu Val Lys Lys Gly Asn Ser Tyr Pro
165 170 175

Lys Ala Ala Ala Ser Tyr Ile Asn Ala Lys Ala Lys Glu Val Leu Val

-continued

```
            180                 185                 190

Leu Trp Ala Ile His His Pro Ala Thr Ala Ala Asp Gln Gln Ser Leu
        195                 200                 205

Tyr Gln Asn Ala Asp Ala Tyr Val Phe Val Gly Ala Ser Ala Tyr Ser
    210                 215                 220

Ala Lys Phe Ala Pro Glu Ile Ala Ala Arg Pro Lys Val Arg Ala Gln
225                 230                 235                 240

Ala Gly Arg Met Asn Tyr Tyr Trp Thr Leu Ala Glu Pro Gly Asp Ala
                245                 250                 255

Ile Thr Phe Glu Ala Thr Gly Asn Leu Val Val Pro Arg Tyr Ala Phe
            260                 265                 270

Ala Ala Ala Arg Ala Ala Gly Ser Gly Ile Ile Ile Ser Asp Ala Ala
        275                 280                 285

Val His Asp Cys Ala Thr Thr Cys Gln Thr Pro Ala Gly Ala Ile Asn
    290                 295                 300

Thr Ser Leu Pro Phe Gln Asn Ile His Pro Ala Thr Ile Gly Ala Cys
305                 310                 315                 320

Pro Lys Tyr Val Lys Ser Thr Lys Leu Arg Ala Ala Thr Gly Leu Arg
                325                 330                 335

Asn Ala Pro Ser Ile Gln Ser Arg Gly Leu Phe Gly Ala Ile Ala Gly
            340                 345                 350

Phe Ile Glu Gly Gly Trp Thr Gly Met Ala Asp Gly Trp Tyr Gly Tyr
        355                 360                 365

His His Gln Asn Glu Gln Gly Ser Gly Tyr Ala Ala Asp Ala Lys Ser
    370                 375                 380

Thr Gln Asn Ala Ile Asp Ala Ile Thr Asn Lys Val Asn Ser Val Ile
385                 390                 395                 400

Glu Lys Met Asn Thr Gln Phe Thr Ala Val Gly Lys Glu Phe Ala His
                405                 410                 415

Leu Glu Ala Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ala Gln Leu Lys Asn Asn Ala Lys Glu Ile Gly Asn Gly
465                 470                 475                 480

Cys Phe Glu Phe Tyr His Lys Cys Asp Ala Ala Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Ala Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Ala
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 158
<211> LENGTH: 85
<212> TYPE: PRT
<213> ORGANISM: Influenza A virus
<220> FEATURE:
<221> NAME/KEY: misc_feature
<222> LOCATION: (1)..(85)
<223> OTHER INFORMATION: Influenza A H1N1 Hemagglutinin 2009 residues 145-229

<400> SEQUENCE: 158

Ser Asn Lys Gly Val Thr Ala Ala Cys Pro His Ala Gly Ala Lys Ser
1 5 10 15

Phe Tyr Lys Asn Leu Ile Trp Leu Val Lys Lys Gly Asn Ser Tyr Pro
20 25 30

Lys Leu Ser Lys Ser Tyr Ile Asn Asp Lys Gly Lys Glu Val Leu Val
35 40 45

Leu Trp Gly Ile His His Pro Ser Thr Ser Ala Asp Gln Gln Ser Leu
50 55 60

Tyr Gln Asn Ala Asp Ala Tyr Val Phe Val Gly Ser Ser Arg Tyr Ser
65 70 75 80

Lys Lys Phe Lys Pro
85

<210> SEQ ID NO 159
<211> LENGTH: 85
<212> TYPE: PRT
<213> ORGANISM: Influenza A virus
<220> FEATURE:
<221> NAME/KEY: misc_feature
<222> LOCATION: (1)..(85)
<223> OTHER INFORMATION: Influenza A H1N1 Hemagglutinin 2010 residues 145-229

<400> SEQUENCE: 159

Ser Asn Lys Gly Val Thr Ala Ala Cys Pro His Ala Gly Ala Lys Ser
1 5 10 15

Phe Tyr Lys Asn Leu Ile Trp Leu Val Lys Lys Gly Asn Ser Tyr Pro
20 25 30

Lys Leu Ser Lys Ser Tyr Ile Asn Asp Lys Gly Lys Glu Val Leu Val
35 40 45

Leu Trp Gly Ile His His Pro Pro Thr Ser Ala Asp Gln Gln Ser Leu
50 55 60

Tyr Gln Asn Ala Asp Ala Tyr Val Phe Val Gly Thr Ser Arg Tyr Ser
65 70 75 80

Lys Lys Phe Lys Pro
85

<210> SEQ ID NO 160
<211> LENGTH: 85
<212> TYPE: PRT
<213> ORGANISM: Influenza A virus
<220> FEATURE:
<221> NAME/KEY: misc_feature
<222> LOCATION: (1)..(85)
<223> OTHER INFORMATION: Influenza A H1N1 Hemagglutinin 2011 residues 145-229

<400> SEQUENCE: 160

Thr Thr Arg Gly Thr Thr Val Ala Cys Ser His Ser Gly Ala Asn Ser
1 5 10 15

Phe Tyr Arg Asn Leu Leu Trp Ile Val Lys Lys Gly Asn Ser Tyr Pro
20 25 30

Lys Leu Ser Lys Ser Tyr Thr Asn Asn Lys Gly Lys Glu Val Leu Val
35 40 45

```
Ile Trp Gly Val His His Pro Pro Thr Asp Ser Asp Gln Gln Thr Leu
    50                  55                  60

Tyr Gln Asn Asn His Thr Tyr Val Ser Val Gly Ser Ser Lys Tyr Tyr
65                  70                  75                  80

Lys Arg Leu Thr Pro
                85


<210> SEQ ID NO 161
<211> LENGTH: 85
<212> TYPE: PRT
<213> ORGANISM: Influenza A virus
<220> FEATURE:
<221> NAME/KEY: misc_feature
<222> LOCATION: (1)..(85)
<223> OTHER INFORMATION: Influenza A H1N1 Hemagglutinin 2012 residues
      145-229

<400> SEQUENCE: 161

Ser Asn Lys Gly Val Thr Ala Ala Cys Pro His Ala Gly Ala Lys Gly
1               5                   10                  15

Phe Tyr Lys Asn Leu Ile Trp Leu Val Lys Lys Gly Asn Ser Tyr Pro
            20                  25                  30

Lys Leu Ser Lys Ser Tyr Ile Asn Asp Lys Gly Lys Glu Val Leu Val
        35                  40                  45

Leu Trp Gly Ile His His Pro Ser Thr Thr Ala Asp Gln Gln Ser Leu
    50                  55                  60

Tyr Gln Asn Ala Asp Thr Tyr Val Phe Val Gly Thr Ser Arg Tyr Ser
65                  70                  75                  80

Lys Lys Phe Lys Pro
                85


<210> SEQ ID NO 162
<211> LENGTH: 85
<212> TYPE: PRT
<213> ORGANISM: Influenza A virus
<220> FEATURE:
<221> NAME/KEY: misc_feature
<222> LOCATION: (1)..(85)
<223> OTHER INFORMATION: Influenza A H1N1 Hemagglutinin 2013 residues
      145-229

<400> SEQUENCE: 162

Ser Asn Lys Gly Val Thr Ala Ala Cys Pro His Ala Gly Ala Lys Ser
1               5                   10                  15

Phe Tyr Lys Asn Leu Ile Trp Leu Val Lys Lys Gly Asn Ser Tyr Pro
            20                  25                  30

Lys Leu Ser Lys Ser Tyr Ile Asn Asp Lys Gly Lys Glu Val Leu Val
        35                  40                  45

Leu Trp Gly Ile His His Pro Ser Thr Thr Ala Asp Gln Gln Ser Leu
    50                  55                  60

Tyr Gln Asn Ala Asn Ala Tyr Val Phe Val Gly Thr Ser Lys Tyr Ser
65                  70                  75                  80

Lys Lys Phe Lys Pro
                85


<210> SEQ ID NO 163
<211> LENGTH: 85
<212> TYPE: PRT
<213> ORGANISM: Influenza A virus
<220> FEATURE:
<221> NAME/KEY: misc_feature
<222> LOCATION: (1)..(85)
```

<223> OTHER INFORMATION: Influenza A H1N1 Hemagglutinin 2014 residues 145-229

<400> SEQUENCE: 163

Ser Asn Lys Gly Val Thr Ala Ala Cys Pro His Ala Gly Ala Lys Ser
1 5 10 15

Phe Tyr Lys Asn Leu Ile Trp Leu Val Lys Lys Gly Asn Ser Tyr Pro
20 25 30

Lys Leu Ser Lys Ser Tyr Ile Asn Asp Lys Gly Lys Glu Val Leu Val
35 40 45

Leu Trp Gly Ile His His Pro Ser Thr Ser Ala Asp Gln Gln Ser Leu
50 55 60

Tyr Gln Asn Ala Asp Ala Tyr Val Phe Val Gly Thr Ser Arg Tyr Ser
65 70 75 80

Lys Lys Phe Lys Pro
85

<210> SEQ ID NO 164
<211> LENGTH: 85
<212> TYPE: PRT
<213> ORGANISM: Influenza A virus
<220> FEATURE:
<221> NAME/KEY: misc_feature
<222> LOCATION: (1)..(85)
<223> OTHER INFORMATION: Influenza A H1N1 Hemagglutinin 2015 residues 145-229

<400> SEQUENCE: 164

Ser Asn Lys Gly Val Thr Ala Ala Cys Pro His Ala Gly Ala Lys Ser
1 5 10 15

Phe Tyr Lys Asn Leu Ile Trp Leu Val Lys Lys Gly Asn Ser Tyr Pro
20 25 30

Lys Leu Ser Lys Ser Tyr Ile Asn Asp Lys Gly Lys Glu Val Leu Val
35 40 45

Leu Trp Gly Ile His His Pro Ser Thr Ser Ala Asp Gln Gln Ser Leu
50 55 60

Tyr Gln Asn Ala Asp Ala Tyr Val Phe Val Gly Thr Ser Arg Tyr Ser
65 70 75 80

Lys Lys Phe Lys Pro
85

<210> SEQ ID NO 165
<211> LENGTH: 85
<212> TYPE: PRT
<213> ORGANISM: Influenza A virus
<220> FEATURE:
<221> NAME/KEY: misc_feature
<222> LOCATION: (1)..(85)
<223> OTHER INFORMATION: Influenza A H1N1 Hemagglutinin 2016 residues 145-229

<400> SEQUENCE: 165

Ser Asn Lys Gly Val Thr Ala Ala Cys Pro His Ala Gly Ala Lys Ser
1 5 10 15

Phe Tyr Lys Asn Leu Ile Trp Leu Val Lys Lys Gly Asn Ser Tyr Pro
20 25 30

Lys Leu Asn Gln Ser Tyr Ile Asn Asp Lys Gly Lys Glu Val Leu Val
35 40 45

Leu Trp Gly Ile His His Pro Ser Thr Thr Ala Asp Gln Gln Ser Leu
50 55 60

Tyr Gln Asn Ala Asp Ala Tyr Val Phe Val Gly Thr Ser Arg Tyr Ser
65 70 75 80

Lys Lys Phe Lys Pro
85

<210> SEQ ID NO 166
<211> LENGTH: 85
<212> TYPE: PRT
<213> ORGANISM: Influenza A virus
<220> FEATURE:
<221> NAME/KEY: misc_feature
<222> LOCATION: (1)..(85)
<223> OTHER INFORMATION: Influenza A H1N1 Hemagglutinin 2017 residues 145-229

<400> SEQUENCE: 166

Ser Asn Lys Gly Val Thr Ala Ala Cys Pro His Ala Gly Ala Lys Ser
1 5 10 15

Phe Tyr Lys Asn Leu Ile Trp Leu Val Lys Lys Gly Asn Ser Tyr Pro
20 25 30

Lys Leu Asn Gln Thr Tyr Ile Asn Asp Lys Gly Lys Glu Val Leu Val
35 40 45

Leu Trp Gly Ile His His Pro Pro Thr Thr Ala Asp Gln Gln Ser Leu
50 55 60

Tyr Gln Asn Ala Asp Ala Tyr Val Phe Val Gly Thr Ser Arg Tyr Ser
65 70 75 80

Lys Lys Phe Lys Pro
85

<210> SEQ ID NO 167
<211> LENGTH: 85
<212> TYPE: PRT
<213> ORGANISM: Influenza A virus
<220> FEATURE:
<221> NAME/KEY: misc_feature
<222> LOCATION: (1)..(85)
<223> OTHER INFORMATION: Influenza A H1N1 Hemagglutinin 2018 residues 145-229

<400> SEQUENCE: 167

Ser Asp Lys Gly Val Thr Ala Ala Cys Pro His Ala Gly Ala Lys Ser
1 5 10 15

Phe Tyr Lys Asn Leu Ile Trp Leu Val Lys Lys Gly Asn Ser Tyr Pro
20 25 30

Lys Leu Asn Gln Thr Tyr Ile Asn Asp Lys Gly Lys Glu Val Leu Val
35 40 45

Leu Trp Gly Ile His His Pro Pro Thr Ile Ala Asp Gln Gln Ser Leu
50 55 60

Tyr Gln Asn Ala Asp Ala Tyr Val Phe Val Gly Thr Ser Arg Tyr Ser
65 70 75 80

Lys Lys Phe Lys Pro
85

<210> SEQ ID NO 168
<211> LENGTH: 85
<212> TYPE: PRT
<213> ORGANISM: Influenza A virus
<220> FEATURE:
<221> NAME/KEY: misc_feature
<222> LOCATION: (1)..(85)
<223> OTHER INFORMATION: Influenza A H1N1 Hemagglutinin 2019 residues 145-229

<400> SEQUENCE: 168

Ser Asn Lys Gly Val Thr Ala Ala Cys Pro His Ala Gly Ala Lys Ser
1               5                   10                  15

Phe Tyr Lys Asn Leu Ile Trp Leu Val Lys Lys Gly Asn Ser Tyr Pro
            20                  25                  30

Lys Ile Asn Gln Thr Tyr Ile Asn Asp Lys Gly Lys Glu Val Leu Val
        35                  40                  45

Leu Trp Gly Ile His His Pro Pro Thr Thr Ala Asp Gln Gln Ser Leu
    50                  55                  60

Tyr Gln Asn Ala Asp Ala Tyr Val Phe Val Gly Thr Ser Arg Tyr Ser
65                  70                  75                  80

Lys Lys Phe Lys Pro
                85

<210> SEQ ID NO 169
<211> LENGTH: 1701
<212> TYPE: DNA
<213> ORGANISM: Influenza A virus
<220> FEATURE:
<221> NAME/KEY: misc_feature
<222> LOCATION: (1)..(1701)
<223> OTHER INFORMATION: H1N1 Hemagglutinin A/Michigan/45/2015 strain
      (nucleotide) GenBank: MK622940.1

<400> SEQUENCE: 169
atgaaggcaa tactagtagt tctgctatat acatttacaa ccgcaaatgc agacacatta      60
tgtataggtt atcatgcgaa caattcaaca gacactgtag acacagtact agaaaagaat     120
gtaacagtaa cacactctgt taaccttctg gaagacaagc ataacggaaa actatgcaaa     180
ctaagagggg tagccccatt gcatttgggt aaatgtaaca ttgctggctg gatcctggga     240
aatccagagt gtgaatcrct ctccacagca agttcatggt cctacattgt ggaaacatct     300
aattcagaca atggaacgtg ttacccagga gatttcatca attatgagga gctaagagag     360
caattgagct cagtgtcatc atttgaaagg tttgagatat tccccaagac aagttcatgg     420
cccaatcatg actcgaacaa aggtgtaacg gcagcatgtc ctcacgctgg agcaaaaagc     480
ttctacaaaa acttgatatg gctagttaaa aaaggaaatt catacccaaa gcttaaccaa     540
tcctacatta atgataaagg gaaagaagtc ctcgtgctgt ggggcattca ccatccatct     600
actactgctg accaacaaag tctctatcag aatgcagatg catatgtttt tgtggggaca     660
tcaagataca gcaagaagtt caagccggaa atagcaacaa gacccaaagt gagggatcaa     720
gaagggagaa tgaactatta ctggacacta gtagagccgg gagacaaaat aacattcgaa     780
gcaactggaa atctagtggt accgagatat gcattcacaa tggaaagaaa tgctggatct     840
ggtattatca tttcagatac accagtccac gattgcaata caacttgtca gacacccgag     900
ggtgctataa acaccagcct cccatttcag aatatacatc cgatcacaat tggaaaatgt     960
ccaaagtatg taaaaagcac aaaattgaga ctggccacag gattgaggaa tgttccgtct    1020
attcaatcta gaggcctatt cggggccatt gccggcttca ttgaaggggg gtggacaggg    1080
atggtagatg gatggtacgg ttatcaccat caaaatgagc aggggtcagg atatgcagcc    1140
gacctgaaga gcacacaaaa tgccattgac aagattacta acaaagtaaa ttctgttatt    1200
gaaaagatga atacacagtt cacagcagtg ggtaaagagt tcaaccacct ggaaaaaaga    1260
atagagaatc taaataaaaa agttgatgat ggtttcctgg acatttggac ttacaatgcc    1320
gaactgttgg ttctattgga aaatgaaaga actttggact atcacgattc aaatgtgaag    1380

-continued

```
aacttgtatg aaaaagtaag aaaccagtta aaaaacaatg ccaaggaaat tggaaacggc   1440

tgctttgaat tttaccacaa atgcgataac acgtgcatgg aaagtgtcaa aaatgggact   1500

tatgactacc caaaatactc agaggaagca aaattaaaca gagaaaaaat agatggggta   1560

aagctggaat caacaaggat ttaccagatt ttggcgatct attcaactgt cgccagttca   1620

ttggtactgg tagtctccct gggggcaatc agcttctgga tgtgctctaa tgggtctcta   1680

cagtgtagaa tatgtattta a                                             1701
```

```
<210> SEQ ID NO 170
<211> LENGTH: 1701
<212> TYPE: DNA
<213> ORGANISM: Influenza A virus
<220> FEATURE:
<221> NAME/KEY: misc_feature
<222> LOCATION: (1)..(1701)
<223> OTHER INFORMATION: Variant of H1N1 Hemagglutinin
      A/Michigan/45/2015 strain (nucleotide)   GenBank: MK622940.1
      Hypervariable residues substituted with Ala

<400> SEQUENCE: 170

atgaaggcaa tactagtagt tctgctatat acatttgcag ccgcaaatgc agacacatta     60

tgtataggtt atcatgcgaa caattcaaca gacactgtag acacagtact agaaaagaat    120

gtaacagtaa cacactctgt taaccttctg gaagccgcgc ataacggaaa actatgcaaa    180

ctaagagggg tagccccatt gcatttgggt aaatgtaaca ttgctggctg ggccctggga    240

aatccagagt gtgaagcrct cgccacagca agttcatggt cctacattgt ggaaacatct    300

gcttcagaca atggaacgtg ttacccagga gatttcatcg cttatgagga gctaagagag    360

caattgagct cagtgtcatc atttgaaagg tttgagatat tccccaaggc aagttcatgg    420

cccaatcatg acgcgaacgc aggtgtaacg gcagcatgtc ctgccgctgg agcagcagcc    480

ttctacgcaa acttgatatg gctagttaaa aaaggaaatt catacccaaa ggctgccgca    540

tcctacatta atgctaaagc gaaagaagtc ctcgtgctgt gggccattca ccatccagct    600

actgctgctg accaacaaag tctctatcag aatgcagatg catatgtttt tgtggggaca    660

tcagcataca gcgcgaagtt cgcgccggaa atagcagcaa gacccaaagt gagggctcaa    720

gcagggagaa tgaactatta ctggacacta gcagagccgg gagacgcaat aacattcgaa    780

gcaactggaa atctagtggt accgagatat gcattcgcag cggcaagagc tgctggatct    840

ggtattatca tttcagatgc agcagtccac gattgcgcta caacttgtca gacacccgcg    900

ggtgctataa acaccagcct cccatttcag aatatacatc cggccacaat tggagcatgt    960

ccaaagtatg taaaaagcac aaaattgaga gcggccacag gattgaggaa tgctccgtct   1020

attcaatcta gaggcctatt cggggccatt gccggcttca ttgaaggggg gtggacaggg   1080

atggcagatg gatggtacgg ttatcaccat caaaatgagc aggggtcagg atatgcagcc   1140

gacgcgaaga gcacacaaaa tgccattgac gcgattacta acaaagtaaa ttctgttatt   1200

gaaaagatga atacacagtt cacagcagtg ggtaaagagt tcgcccacct ggaagcaaga   1260

atagagaatc taaataaaaa agttgatgat ggtttcctgg acatttggac ttacaatgcc   1320

gaactgttgg ttctattgga aaatgaaaga actttggact atcacgattc aaatgtgaag   1380

aacttgtatg aaaaagtaag agcccagtta aaaaacaatg ccaaggaaat tggaaacggc   1440

tgctttgaat tttaccacaa atgcgatgcc gcgtgcatgg aaagtgtcaa aaatgggact   1500

tatgactacc caaaatactc agaggaagca aaattaaaca gagaagcaat agatggggta   1560

aagctggaat caacaaggat ttaccagatt ttggcgatct attcaactgt cgccagttca   1620
```

```
ttggtactgg cagtctccct gggggcaatc agcttctgga tgtgctctaa tgggtctcta   1680

cagtgtagaa tatgtattta a                                             1701


<210> SEQ ID NO 171
<211> LENGTH: 252
<212> TYPE: PRT
<213> ORGANISM: Influenza A virus
<220> FEATURE:
<221> NAME/KEY: misc_feature
<222> LOCATION: (1)..(252)
<223> OTHER INFORMATION: H3N2 M1 Protein

<400> SEQUENCE: 171

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Ala Thr Thr Asn Pro Leu Ile Lys His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Ile Ala Ser Gln
        195                 200                 205

Ala Arg Gln Met Val Gln Ala Met Arg Ala Ile Gly Thr His Pro Ser
    210                 215                 220

Ser Ser Thr Gly Leu Arg Asp Asp Leu Leu Glu Asn Leu Gln Thr Tyr
225                 230                 235                 240

Gln Lys Arg Met Gly Val Gln Met Gln Arg Phe Lys
                245                 250


<210> SEQ ID NO 172
<211> LENGTH: 121
<212> TYPE: PRT
<213> ORGANISM: Influenza A virus
<220> FEATURE:
<221> NAME/KEY: misc_feature
<222> LOCATION: (1)..(121)
<223> OTHER INFORMATION: H3N2 NEP Protein

<400> SEQUENCE: 172

Met Asp Ser Asn Thr Val Ser Ser Phe Gln Asp Ile Leu Leu Arg Met
1               5                   10                  15
```

Ser Lys Met Gln Leu Gly Ser Ser Ser Glu Asp Leu Asn Gly Met Ile
20 25 30

Thr Gln Phe Glu Ser Leu Lys Ile Tyr Arg Asp Ser Leu Gly Glu Ala
35 40 45

Val Met Arg Met Gly Asp Leu His Leu Leu Gln Asn Arg Asn Gly Lys
50 55 60

Trp Arg Glu Gln Leu Gly Gln Lys Phe Glu Glu Ile Arg Trp Leu Ile
65 70 75 80

Glu Glu Val Arg His Arg Leu Arg Thr Thr Glu Asn Ser Phe Glu Gln
85 90 95

Ile Thr Phe Met Gln Ala Leu Gln Leu Leu Phe Glu Val Glu Gln Glu
100 105 110

Ile Arg Thr Phe Ser Phe Gln Leu Ile
115 120

<210> SEQ ID NO 173
<211> LENGTH: 498
<212> TYPE: PRT
<213> ORGANISM: Influenza A virus
<220> FEATURE:
<221> NAME/KEY: misc_feature
<222> LOCATION: (1)..(498)
<223> OTHER INFORMATION: H3N2 NP Protein

<400> SEQUENCE: 173

Met Ala Ser Gln Gly Thr Lys Arg Ser Tyr Glu Gln Met Glu Thr Asp
1 5 10 15

Gly Asp Arg Gln Asn Ala Thr Glu Ile Arg Ala Ser Val Gly Lys Met
20 25 30

Ile Asp Gly Ile Gly Arg Phe Tyr Ile Gln Met Cys Thr Glu Leu Lys
35 40 45

Leu Ser Asp His Glu Gly Arg Leu Ile Gln Asn Ser Leu Thr Ile Glu
50 55 60

Lys Met Val Leu Ser Ala Phe Asp Glu Arg Arg Asn Lys Tyr Leu Glu
65 70 75 80

Glu His Pro Ser Ala Gly Lys Asp Pro Lys Lys Thr Gly Gly Pro Ile
85 90 95

Tyr Arg Arg Val Asp Gly Lys Trp Met Arg Glu Leu Val Leu Tyr Asp
100 105 110

Lys Glu Glu Ile Arg Arg Ile Trp Arg Gln Ala Asn Asn Gly Glu Asp
115 120 125

Ala Thr Ser Gly Leu Thr His Ile Met Ile Trp His Ser Asn Leu Asn
130 135 140

Asp Ala Thr Tyr Gln Arg Thr Arg Ala Leu Val Arg Thr Gly Met Asp
145 150 155 160

Pro Arg Met Cys Ser Leu Met Gln Gly Ser Thr Leu Pro Arg Arg Ser
165 170 175

Gly Ala Ala Gly Ala Ala Val Lys Gly Ile Gly Thr Met Val Met Glu
180 185 190

Leu Ile Arg Met Val Lys Arg Gly Ile Asn Asp Arg Asn Phe Trp Arg
195 200 205

Gly Glu Asn Gly Arg Lys Thr Arg Ser Ala Tyr Glu Arg Met Cys Asn
210 215 220

Ile Leu Lys Gly Lys Phe Gln Thr Ala Ala Gln Arg Ala Met Val Asp
225 230 235 240

```
Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Ala Tyr Gly Pro Ala Val Ser Ser Gly
        275                 280                 285

Tyr Asp Phe Glu Lys Glu Gly Tyr Ser Leu Val Gly Ile Asp Pro Phe
    290                 295                 300

Lys Leu Leu Gln Asn Ser Gln Ile Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Leu Leu Ser Phe Ile Arg Gly Thr Lys Val
            340                 345                 350

Ser Pro Arg Gly Lys Leu Ser Thr Arg Gly Val Gln Ile Ala Ser Asn
        355                 360                 365

Glu Asn Met Asp Asn Met Gly Ser Ser Thr Leu Glu Leu Arg Ser Gly
    370                 375                 380

Tyr Trp Ala Ile Arg Thr Arg Ser Gly Gly Asn Thr Asn Gln Gln Arg
385                 390                 395                 400

Ala Ser Ala Gly Gln Thr Ser Val Gln Pro Thr Phe Ser Val Gln Arg
                405                 410                 415

Asn Leu Pro Phe Glu Lys Ser Thr Ile Met Ala Ala Phe Thr Gly Asn
            420                 425                 430

Thr Glu Gly Arg Thr Ser Asp Met Arg Ala Glu Ile Ile Arg Met Met
        435                 440                 445

Glu Gly Ala Lys Pro Glu Glu Val Ser Phe Arg Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn


<210> SEQ ID NO 174
<211> LENGTH: 217
<212> TYPE: PRT
<213> ORGANISM: Influenza A virus
<220> FEATURE:
<221> NAME/KEY: misc_feature
<222> LOCATION: (1)..(217)
<223> OTHER INFORMATION: H3N2 NS1 Protein

<400> SEQUENCE: 174

Met Asp Ser Asn Thr Val Ser Ser Phe Gln Val Asp Cys Phe Leu Trp
1               5                   10                  15

His Ile Arg Lys Gln Val Val Asp Gln Lys Leu Ser Asp Ala Pro Phe
            20                  25                  30

Leu Asp Arg Leu Arg Arg Asp Gln Arg Ser Leu Arg Gly Arg Gly Asn
        35                  40                  45

Thr Leu Gly Leu Asp Ile Lys Ala Ala Thr His Val Gly Lys Gln Ile
    50                  55                  60

Val Glu Lys Ile Leu Lys Glu Glu Ser Asp Glu Ala Leu Lys Met Thr
65                  70                  75                  80

Met Val Ser Thr Pro Ala Ser Arg Tyr Ile Thr Asp Met Thr Ile Glu
                85                  90                  95
```

```
Glu Leu Ser Arg Asn Trp Phe Met Leu Met Pro Lys Gln Lys Val Glu
            100                 105                 110

Gly Pro Leu Cys Ile Arg Met Asp Gln Ala Ile Met Glu Lys Asn Ile
        115                 120                 125

Met Leu Lys Ala Asn Phe Asn Val Ile Phe Gly Arg Leu Glu Thr Ile
    130                 135                 140

Val Leu Leu Arg Ala Phe Thr Glu Glu Gly Ala Ile Val Gly Glu Ile
145                 150                 155                 160

Ser Pro Leu Pro Ser Phe Pro Gly His Thr Ile Glu Asp Val Lys Asn
                165                 170                 175

Ala Ile Gly Val Leu Ile Gly Gly Leu Glu Trp Asn Asp Asn Thr Val
            180                 185                 190

Arg Val Ser Lys Asn Leu Gln Arg Phe Ala Trp Arg Ser Ser Asn Glu
        195                 200                 205

Asn Gly Gly Pro Pro Leu Thr Pro Lys
    210                 215


<210> SEQ ID NO 175
<211> LENGTH: 121
<212> TYPE: PRT
<213> ORGANISM: Influenza A virus
<220> FEATURE:
<221> NAME/KEY: misc_feature
<222> LOCATION: (1)..(121)
<223> OTHER INFORMATION: H3N2 NS2 Protein

<400> SEQUENCE: 175

Met Asp Ser Asn Thr Val Ser Ser Phe Gln Asp Ile Leu Leu Arg Met
1               5                   10                  15

Ser Lys Met Gln Leu Gly Ser Ser Ser Glu Asp Leu Asn Gly Met Ile
            20                  25                  30

Thr Gln Phe Glu Ser Leu Lys Ile Tyr Arg Asp Ser Leu Gly Glu Ala
        35                  40                  45

Val Met Arg Met Gly Asp Leu His Leu Leu Gln Asn Arg Asn Gly Lys
    50                  55                  60

Trp Arg Glu Gln Leu Gly Gln Lys Phe Glu Glu Ile Arg Trp Leu Ile
65                  70                  75                  80

Glu Glu Val Arg His Arg Leu Lys Thr Thr Glu Asn Ser Phe Glu Gln
                85                  90                  95

Ile Thr Phe Met Gln Ala Leu Gln Leu Leu Phe Glu Val Glu Gln Glu
            100                 105                 110

Ile Arg Thr Phe Ser Phe Gln Leu Ile
        115                 120


<210> SEQ ID NO 176
<211> LENGTH: 716
<212> TYPE: PRT
<213> ORGANISM: Influenza A virus
<220> FEATURE:
<221> NAME/KEY: misc_feature
<222> LOCATION: (1)..(716)
<223> OTHER INFORMATION: H3N2 PA Protein

<400> SEQUENCE: 176

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Leu Lys Ile Glu Thr
            20                  25                  30
```

```
Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Val Val Glu
    50                  55                  60

Leu Asp Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Gly Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Asn Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Asn Arg Gly Leu Trp Asp Ser Phe Arg
            180                 185                 190

Gln Ser Glu Arg Gly Glu Glu Thr Ile Glu Glu Lys Phe Glu Ile Thr
        195                 200                 205

Gly Thr Met Arg Arg Leu Ala Asp Gln Ser Leu Pro Pro Asn Phe Ser
    210                 215                 220

Cys Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Gln
                245                 250                 255

Ile Glu Pro Phe Leu Lys Thr Thr Pro Arg Pro Ile Lys Leu Pro Ser
            260                 265                 270

Gly Pro Pro Cys Tyr Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Ile Lys Thr Phe Phe Gly Trp Lys Glu Pro
305                 310                 315                 320

Tyr Ile Val Lys Pro His Glu Lys Gly Ile Asn Ser Asn Tyr Leu Leu
                325                 330                 335

Ser Trp Lys Gln Val Leu Ser Glu Leu Gln Asp Ile Glu Asn Glu Glu
            340                 345                 350

Lys Ile Pro Arg Thr Lys Asn Met Lys Lys Thr Ser Gln Leu Lys Trp
        355                 360                 365

Ala Leu Gly Glu Asn Met Ala Pro Glu Lys Val Asp Phe Glu Asn Cys
    370                 375                 380

Arg Asp Ile Ser Asp Leu Lys Gln Tyr Asp Ser Glu Glu Pro Glu Leu
385                 390                 395                 400

Arg Ser Leu Ser Ser Trp Ile Gln Ser Glu Phe Asn Lys Ala Cys Glu
                405                 410                 415

Leu Thr Asp Ser Val Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
```

450 455 460

Ile Asn Thr Ala Leu Leu Asn Ala Ser Cys Ala Ala Met Asp Asp Phe
465 470 475 480

Gln Leu Ile Pro Met Ile Ser Lys Cys Arg Thr Lys Glu Gly Arg Arg
485 490 495

Lys Thr Asn Leu Tyr Gly Phe Ile Ile Lys Gly Arg Ser His Leu Arg
500 505 510

Asn Asp Thr Asp Val Val Asn Phe Val Ser Met Glu Phe Ser Leu Thr
515 520 525

Asp Pro Arg Leu Glu Pro His Lys Trp Glu Lys Tyr Cys Val Leu Glu
530 535 540

Ile Gly Asp Met Leu Leu Arg Ser Ala Ile Gly Gln Ile Ser Arg Pro
545 550 555 560

Met Phe Leu Tyr Val Arg Thr Asn Gly Thr Ser Lys Val Lys Met Lys
565 570 575

Trp Gly Met Glu Met Arg Arg Cys Leu Leu Gln Ser Leu Gln Gln Ile
580 585 590

Glu Ser Met Ile Glu Ala Glu Ser Ser Val Lys Glu Lys Asp Met Thr
595 600 605

Lys Glu Phe Phe Glu Asn Lys Ser Glu Ala Trp Pro Ile Gly Glu Ser
610 615 620

Pro Lys Gly Val Glu Glu Gly Ser Ile Gly Lys Val Cys Arg Thr Leu
625 630 635 640

Leu Ala Lys Ser Val Phe Asn Ser Leu Tyr Ala Ser Pro Gln Leu Glu
645 650 655

Gly Phe Ser Ala Glu Ser Arg Lys Leu Leu Leu Ile Val Gln Ala Leu
660 665 670

Arg Asp Lys Leu Glu Pro Gly Thr Phe Asp Leu Gly Gly Leu Tyr Glu
675 680 685

Ala Ile Glu Glu Cys Leu Ile Asn Asp Pro Trp Val Leu Leu Asn Ala
690 695 700

Ser Trp Phe Asn Ser Phe Leu Thr His Ala Leu Lys
705 710 715

<210> SEQ ID NO 177
<211> LENGTH: 252
<212> TYPE: PRT
<213> ORGANISM: Influenza A virus
<220> FEATURE:
<221> NAME/KEY: misc_feature
<222> LOCATION: (1)..(252)
<223> OTHER INFORMATION: H3N2 PA-X Protein

<400> SEQUENCE: 177

Met Glu Asp Phe Val Arg Gln Cys Phe Asn Pro Met Ile Val Glu Leu
1 5 10 15

Ala Glu Lys Ala Met Lys Glu Tyr Gly Glu Asp Leu Lys Ile Glu Thr
20 25 30

Asn Lys Phe Ala Ala Ile Cys Thr His Leu Glu Val Cys Phe Met Tyr
35 40 45

Ser Asp Phe His Phe Ile Asn Glu Gln Gly Glu Ser Ile Val Val Glu
50 55 60

Leu Asp Asp Pro Asn Ala Leu Leu Lys His Arg Phe Glu Ile Ile Glu
65 70 75 80

Gly Arg Asp Arg Thr Met Ala Trp Thr Val Val Asn Ser Ile Cys Asn
85 90 95

-continued

```
Thr Thr Gly Ala Gly Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Asn Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Asn Arg Gly Leu Trp Asp Ser Phe Val
            180                 185                 190

Ser Pro Lys Glu Ala Lys Lys Gln Leu Lys Lys Asn Leu Lys Ser Gln
        195                 200                 205

Glu Leu Cys Ala Gly Leu Pro Thr Lys Val Ser His Arg Thr Ser Pro
    210                 215                 220

Ala Leu Arg Ile Leu Glu Pro Met Trp Met Asp Ser Asn Arg Thr Ala
225                 230                 235                 240

Ala Leu Arg Ala Ser Phe Leu Lys Cys Pro Lys Lys
                245                 250


<210> SEQ ID NO 178
<211> LENGTH: 757
<212> TYPE: PRT
<213> ORGANISM: Influenza A virus
<220> FEATURE:
<221> NAME/KEY: misc_feature
<222> LOCATION: (1)..(757)
<223> OTHER INFORMATION: H3N2 PB1 Protein

<400> SEQUENCE: 178

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Arg Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Ala Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Met Glu Ile Thr Thr His Phe Gln Arg Lys Arg Arg Val Arg
            180                 185                 190
```

```
Asp Asn Met Thr Lys Lys Met Val Thr Gln Arg Thr Ile Gly Lys Lys
        195                 200                 205

Lys Gln Arg Val Asn Lys Arg Gly Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Lys Asn Gln Pro Glu Trp Phe Arg Asn Ile
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Arg Met Lys Leu Arg Thr Gln Ile
        355                 360                 365

Pro Ala Glu Met Leu Ala Ser Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Lys Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
                565                 570                 575

Lys Lys Leu Trp Asp Gln Thr Gln Ser Arg Thr Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asn Tyr Arg Gly Arg Leu
```

```
    610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Ile Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ser Glu Ile Met Lys Ile Cys Ser Thr Ile Glu Glu
            740                 745                 750

Leu Arg Arg Gln Lys
        755


<210> SEQ ID NO 179
<211> LENGTH: 759
<212> TYPE: PRT
<213> ORGANISM: Influenza A virus
<220> FEATURE:
<221> NAME/KEY: misc_feature
<222> LOCATION: (1)..(759)
<223> OTHER INFORMATION: H3N2 PB2 Protein

<400> SEQUENCE: 179

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ser Leu Arg Met Lys
        35                  40                  45

Trp Met Met Ala Met Lys Tyr Pro Ile Thr Ala Asp Lys Arg Ile Thr
    50                  55                  60

Glu Met Val Pro Glu Arg Asn Glu Gln Gly Gln Thr Leu Trp Ser Lys
65                  70                  75                  80

Met Ser Asp Ala Gly Ser Asp Arg Val Met Val Ser Pro Leu Ala Val
                85                  90                  95

Thr Trp Trp Asn Arg Asn Gly Pro Val Thr Ser Thr Val His Tyr Pro
            100                 105                 110

Lys Val Tyr Lys Thr Tyr Phe Asp Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Arg Asp Cys Lys Ile Ser Pro Leu Met Val Ala Tyr Met Leu Glu
        195                 200                 205
```

```
Arg Glu Leu Val Arg Lys Thr Arg Phe Leu Pro Val Ala Gly Gly Thr
    210                 215                 220

Ser Ser Ile Tyr Ile Glu Val Leu His Leu Thr Gln Gly Thr Cys Trp
225                 230                 235                 240

Glu Gln Met Tyr Thr Pro Gly Gly Gly Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Thr Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Lys Glu Glu Glu Val Leu Thr Gly Asn Leu Gln Thr Leu
            340                 345                 350

Arg Ile Arg Val His Glu Gly Tyr Glu Glu Phe Thr Met Val Gly Lys
        355                 360                 365

Arg Ala Thr Ala Ile Leu Arg Lys Ala Thr Arg Arg Leu Val Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Val Glu His Ile Asp Ser Val Met Gly Met Val Gly Val Leu
    450                 455                 460

Pro Asp Met Thr Pro Ser Thr Glu Met Ser Met Arg Gly Ile Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Arg Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Ala Val
545                 550                 555                 560

Lys Ile Gln Trp Ser Gln Asn Pro Ala Met Leu Tyr Asn Lys Met Glu
                565                 570                 575

Phe Glu Pro Phe Gln Ser Leu Val Pro Lys Ala Thr Arg Ser Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620
```

-continued

```
Pro Pro Lys Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Thr Thr Lys Arg Leu Thr Ile Leu Gly Lys Asp Ala
            660                 665                 670

Gly Thr Leu Ile Glu Asp Pro Asp Glu Ser Thr Ser Gly Val Glu Ser
        675                 680                 685

Ala Val Leu Arg Gly Phe Leu Ile Ile Gly Lys Glu Asp Arg Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755
```

<210> SEQ ID NO 180
<211> LENGTH: 109
<212> TYPE: PRT
<213> ORGANISM: Influenza B virus
<220> FEATURE:
<221> NAME/KEY: misc_feature
<222> LOCATION: (1)..(109)
<223> OTHER INFORMATION: Influenza B bm2 Protein

<400> SEQUENCE: 180

```
Met Leu Glu Pro Phe Gln Ile Leu Ser Ile Cys Ser Phe Ile Leu Ser
1               5                   10                  15

Ala Leu His Phe Met Ala Trp Thr Ile Gly His Leu Asn Gln Ile Lys
            20                  25                  30

Arg Gly Val Asn Met Lys Ile Arg Ile Lys Gly Pro Asn Lys Glu Thr
        35                  40                  45

Ile Asn Arg Glu Val Ser Ile Leu Arg His Ser Tyr Gln Lys Glu Ile
    50                  55                  60

Gln Ala Lys Glu Ala Met Lys Glu Val Leu Ser Asp Asn Met Glu Val
65                  70                  75                  80

Leu Ser Asp His Ile Val Ile Glu Gly Leu Ser Ala Glu Glu Ile Ile
                85                  90                  95

Lys Met Gly Glu Thr Val Leu Glu Val Glu Glu Leu His
            100                 105
```

<210> SEQ ID NO 181
<211> LENGTH: 248
<212> TYPE: PRT
<213> ORGANISM: Influenza B virus
<220> FEATURE:
<221> NAME/KEY: misc_feature
<222> LOCATION: (1)..(248)
<223> OTHER INFORMATION: Influenza B bm1 Protein

<400> SEQUENCE: 181

```
Met Ser Leu Phe Gly Asp Thr Ile Ala Tyr Leu Leu Ser Leu Thr Glu
1               5                   10                  15

Asp Gly Glu Gly Lys Ala Glu Leu Ala Glu Lys Leu His Cys Trp Phe
            20                  25                  30

Gly Gly Lys Glu Phe Asp Leu Asp Ser Ala Leu Glu Trp Ile Lys Asn
```

```
        35                  40                  45

Lys Arg Cys Leu Thr Asp Ile Gln Lys Ala Leu Ile Gly Ala Ser Ile
    50                  55                  60

Cys Phe Leu Lys Pro Lys Asp Gln Glu Arg Lys Arg Arg Phe Ile Thr
65                  70                  75                  80

Glu Pro Leu Ser Gly Met Gly Thr Thr Ala Thr Lys Lys Lys Gly Leu
                85                  90                  95

Ile Leu Ala Glu Arg Lys Met Arg Lys Cys Val Ser Phe His Glu Ala
            100                 105                 110

Phe Glu Ile Ala Glu Gly His Glu Ser Ser Ala Leu Leu Tyr Cys Leu
        115                 120                 125

Met Val Met Tyr Leu Asn Pro Gly Asn Tyr Ser Met Gln Val Lys Leu
    130                 135                 140

Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
            180                 185                 190

Gly Lys Gly Glu Asp Val Gln Lys Leu Ala Glu Glu Leu Gln Ser Asn
        195                 200                 205

Ile Gly Val Leu Arg Ser Leu Gly Ala Ser Gln Lys Asn Gly Glu Gly
    210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245


<210> SEQ ID NO 182
<211> LENGTH: 122
<212> TYPE: PRT
<213> ORGANISM: Influenza B virus
<220> FEATURE:
<221> NAME/KEY: misc_feature
<222> LOCATION: (1)..(122)
<223> OTHER INFORMATION: Influenza B nep Protein

<400> SEQUENCE: 182

Met Ala Asp Asn Met Thr Thr Thr Gln Ile Glu Trp Arg Met Lys Lys
1               5                   10                  15

Met Ala Ile Gly Ser Ser Ile His Ser Ser Ser Val Leu Met Lys Asp
            20                  25                  30

Ile Gln Ser Gln Phe Glu Gln Leu Lys Leu Arg Trp Glu Ser Tyr Pro
        35                  40                  45

Asn Leu Val Lys Ser Thr Asp Tyr His Gln Lys Arg Glu Thr Ile Arg
    50                  55                  60

Leu Val Thr Glu Glu Leu Tyr Leu Leu Ser Lys Arg Ile Asp Asp Asn
65                  70                  75                  80

Ile Leu Phe His Lys Thr Val Ile Ala Asn Ser Ser Ile Ile Ala Asp
                85                  90                  95

Met Val Val Ser Leu Ser Leu Leu Glu Thr Leu Tyr Glu Met Lys Asp
            100                 105                 110

Val Val Glu Val Tyr Ser Arg Gln Cys Leu
        115                 120


<210> SEQ ID NO 183
```

<211> LENGTH: 281
<212> TYPE: PRT
<213> ORGANISM: Influenza B virus
<220> FEATURE:
<221> NAME/KEY: misc_feature
<222> LOCATION: (1)..(281)
<223> OTHER INFORMATION: Influenza B ns1 Protein

<400> SEQUENCE: 183

```
Met Ala Asp Asn Met Thr Thr Thr Gln Ile Glu Val Gly Pro Gly Ala
1               5                   10                  15

Thr Asn Ala Thr Ile Asn Phe Glu Ala Gly Ile Leu Glu Cys Tyr Glu
            20                  25                  30

Arg Leu Ser Trp Gln Arg Ala Leu Asp Tyr Pro Gly Gln Asp Arg Leu
        35                  40                  45

Asn Arg Leu Lys Arg Lys Leu Glu Ser Arg Ile Lys Thr His Asn Lys
    50                  55                  60

Ser Glu Pro Glu Ser Lys Arg Met Ser Leu Glu Glu Arg Lys Ala Ile
65                  70                  75                  80

Gly Val Lys Met Met Lys Val Leu Leu Phe Met Asn Pro Ser Ala Gly
                85                  90                  95

Ile Glu Gly Phe Glu Pro Tyr Cys Met Lys Ser Ser Ser Asn Ser Asn
            100                 105                 110

Cys Pro Lys Tyr Asn Trp Thr Asp Tyr Pro Ser Thr Pro Gly Arg Cys
        115                 120                 125

Leu Asp Asp Ile Glu Glu Glu Pro Asp Asp Val Asp Gly Pro Thr Glu
    130                 135                 140

Ile Val Leu Arg Asp Met Asn Asn Lys Asp Ala Arg Gln Lys Ile Lys
145                 150                 155                 160

Glu Glu Val Asn Thr Gln Lys Glu Gly Lys Phe Arg Leu Thr Ile Lys
                165                 170                 175

Arg Asp Met Arg Asn Val Leu Ser Leu Arg Val Leu Val Asn Gly Thr
            180                 185                 190

Phe Leu Lys His Pro Asn Gly Tyr Lys Ser Leu Ser Thr Leu His Arg
        195                 200                 205

Leu Asn Ala Tyr Asp Gln Ser Gly Arg Leu Val Ala Lys Leu Val Ala
    210                 215                 220

Thr Asp Asp Leu Thr Val Glu Asp Glu Glu Asp Gly His Arg Ile Leu
225                 230                 235                 240

Asn Ser Leu Phe Glu Arg Leu Asn Glu Gly His Ser Lys Pro Ile Arg
                245                 250                 255

Ala Ala Glu Thr Ala Val Gly Val Leu Ser Gln Phe Gly Gln Glu His
            260                 265                 270

Arg Leu Ser Pro Glu Glu Gly Asp Asn
        275                 280
```

<210> SEQ ID NO 184
<211> LENGTH: 122
<212> TYPE: PRT
<213> ORGANISM: Influenza B virus
<220> FEATURE:
<221> NAME/KEY: misc_feature
<222> LOCATION: (1)..(122)
<223> OTHER INFORMATION: Influenza B ns2 Protein

<400> SEQUENCE: 184

```
Met Ala Asp Asn Met Thr Thr Thr Gln Ile Glu Trp Arg Met Lys Lys
1               5                   10                  15
```

Met Ala Ile Gly Ser Ser Thr His Ser Ser Ser Val Leu Met Lys Asp
20 25 30

Ile Gln Ser Gln Phe Glu Gln Leu Lys Leu Arg Trp Glu Ser Tyr Pro
35 40 45

Asn Leu Val Lys Ser Thr Asp Tyr His Gln Lys Arg Glu Thr Ile Arg
50 55 60

Leu Val Thr Glu Glu Leu Tyr Leu Leu Ser Lys Arg Ile Asp Asp Asn
65 70 75 80

Ile Leu Phe His Lys Thr Val Ile Ala Asn Ser Ser Ile Ile Ala Asp
85 90 95

Met Val Val Ser Leu Ser Leu Leu Glu Thr Leu Tyr Glu Met Lys Asp
100 105 110

Val Val Glu Val Tyr Ser Arg Gln Cys Leu
115 120

<210> SEQ ID NO 185
<211> LENGTH: 726
<212> TYPE: PRT
<213> ORGANISM: Influenza B virus
<220> FEATURE:
<221> NAME/KEY: misc_feature
<222> LOCATION: (1)..(726)
<223> OTHER INFORMATION: Influenza B pa Protein

<400> SEQUENCE: 185

Met Asp Thr Phe Ile Thr Arg Asn Phe Gln Thr Thr Ile Ile Gln Lys
1 5 10 15

Ala Lys Asn Thr Met Ala Glu Phe Ser Glu Asp Pro Glu Leu Gln Pro
20 25 30

Ala Met Leu Phe Asn Ile Cys Val His Leu Glu Val Cys Tyr Val Ile
35 40 45

Ser Asp Met Asn Phe Leu Asp Glu Glu Gly Lys Ala Tyr Thr Ala Leu
50 55 60

Glu Gly Gln Gly Lys Glu Gln Asn Leu Arg Pro Gln Tyr Glu Val Ile
65 70 75 80

Glu Gly Met Pro Arg Thr Ile Ala Trp Met Val Gln Arg Ser Leu Ala
85 90 95

Gln Glu His Gly Ile Glu Thr Pro Lys Tyr Leu Ala Asp Leu Phe Asp
100 105 110

Tyr Lys Thr Lys Arg Phe Ile Glu Val Gly Ile Thr Lys Gly Leu Ala
115 120 125

Asp Asp Tyr Phe Trp Lys Lys Lys Glu Lys Leu Gly Asn Ser Met Glu
130 135 140

Leu Met Ile Phe Ser Tyr Asn Gln Asp Tyr Ser Leu Ser Asn Glu Ser
145 150 155 160

Ser Leu Asp Glu Glu Gly Lys Gly Arg Val Leu Ser Arg Leu Thr Glu
165 170 175

Leu Gln Ala Glu Leu Ser Leu Lys Asn Leu Trp Gln Val Leu Ile Gly
180 185 190

Glu Glu Asp Val Glu Lys Gly Ile Asp Phe Lys Leu Gly Gln Thr Ile
195 200 205

Ser Arg Leu Arg Asp Ile Ser Val Pro Ala Gly Phe Ser Asn Phe Glu
210 215 220

Gly Met Arg Ser Tyr Ile Asp Asn Ile Asp Pro Lys Gly Ala Ile Glu
225 230 235 240

Arg Asn Leu Ala Arg Met Ser Pro Leu Val Ser Val Thr Pro Lys Lys

```
                245                 250                 255

Leu Lys Trp Glu Asp Leu Arg Pro Ile Gly Pro His Ile Tyr Asn His
            260                 265                 270

Glu Leu Pro Glu Val Pro Tyr Asn Ala Phe Leu Leu Met Ser Asp Glu
        275                 280                 285

Leu Gly Leu Ala Asn Met Thr Glu Gly Lys Ser Lys Lys Pro Lys Thr
    290                 295                 300

Leu Ala Lys Glu Cys Leu Glu Lys Tyr Ser Thr Leu Arg Asp Gln Thr
305                 310                 315                 320

Asp Pro Ile Leu Ile Met Lys Ser Glu Lys Ala Asn Glu Asn Phe Leu
                325                 330                 335

Trp Lys Leu Trp Arg Asp Cys Val Asn Thr Ile Ser Asn Glu Glu Met
            340                 345                 350

Ser Asn Glu Leu Gln Lys Thr Asn Tyr Ala Lys Trp Ala Thr Gly Asp
        355                 360                 365

Gly Leu Thr Tyr Gln Lys Ile Met Lys Glu Val Ala Ile Asp Asp Glu
    370                 375                 380

Thr Met Cys Gln Glu Glu Pro Lys Ile Pro Asn Lys Cys Arg Val Ala
385                 390                 395                 400

Ala Trp Val Gln Thr Glu Met Asn Leu Leu Ser Thr Leu Thr Ser Lys
                405                 410                 415

Arg Ala Leu Asp Leu Pro Glu Ile Gly Pro Asp Val Ala Pro Val Glu
            420                 425                 430

His Val Gly Ser Glu Arg Arg Lys Tyr Phe Val Asn Glu Ile Asn Tyr
        435                 440                 445

Cys Lys Ala Ser Thr Val Met Met Lys Tyr Val Leu Phe His Thr Ser
    450                 455                 460

Leu Leu Asn Glu Ser Asn Ala Ser Met Gly Lys Tyr Lys Val Ile Pro
465                 470                 475                 480

Ile Thr Asn Arg Val Val Asn Glu Lys Gly Glu Ser Phe Asp Met Leu
                485                 490                 495

Tyr Gly Leu Ala Val Lys Gly Gln Ser His Leu Arg Gly Asp Thr Asp
            500                 505                 510

Val Val Thr Val Val Thr Phe Glu Phe Ser Ser Thr Asp Pro Arg Val
        515                 520                 525

Asp Ser Gly Lys Trp Pro Lys Tyr Thr Val Phe Arg Ile Gly Ser Leu
    530                 535                 540

Phe Val Ser Gly Arg Glu Lys Ser Val Tyr Leu Tyr Cys Arg Val Asn
545                 550                 555                 560

Gly Thr Asn Lys Ile Gln Met Lys Trp Gly Met Glu Ala Arg Arg Cys
                565                 570                 575

Leu Leu Gln Ser Met Gln Gln Met Glu Ala Ile Val Glu Gln Glu Ser
            580                 585                 590

Ser Ile Gln Gly Tyr Asp Met Thr Lys Ala Cys Phe Lys Gly Asp Arg
        595                 600                 605

Val Asn Ser Pro Lys Thr Phe Ser Ile Gly Thr Gln Glu Gly Lys Leu
    610                 615                 620

Val Lys Gly Ser Phe Gly Lys Ala Leu Arg Val Ile Phe Thr Lys Cys
625                 630                 635                 640

Leu Met His Tyr Val Phe Gly Asn Ala Gln Leu Glu Gly Phe Ser Ala
                645                 650                 655

Glu Ser Arg Arg Leu Leu Leu Leu Ile Gln Ala Leu Lys Asp Arg Lys
            660                 665                 670
```

```
Gly Pro Trp Val Phe Asp Leu Glu Gly Met Tyr Ser Gly Ile Glu Glu
        675                 680                 685

Cys Ile Ser Asn Asn Pro Trp Val Ile Gln Ser Ala Tyr Trp Phe Asn
    690                 695                 700

Glu Trp Leu Gly Phe Glu Lys Glu Gly Ser Lys Val Leu Glu Ser Val
705                 710                 715                 720

Asp Glu Ile Met Asp Glu
                725


<210> SEQ ID NO 186
<211> LENGTH: 752
<212> TYPE: PRT
<213> ORGANISM: Influenza B virus
<220> FEATURE:
<221> NAME/KEY: misc_feature
<222> LOCATION: (1)..(752)
<223> OTHER INFORMATION: Influenza B pb1 Protein

<400> SEQUENCE: 186

Met Asn Ile Asn Pro Tyr Phe Leu Phe Ile Asp Val Pro Ile Gln Ala
1               5                   10                  15

Ala Ile Ser Thr Thr Phe Pro Tyr Thr Gly Val Pro Pro Tyr Ser His
            20                  25                  30

Gly Thr Gly Thr Gly Tyr Thr Ile Asp Thr Val Ile Arg Thr His Glu
        35                  40                  45

Tyr Ser Asn Lys Gly Lys Gln Tyr Val Ser Asp Ile Thr Gly Cys Thr
    50                  55                  60

Met Val Asp Pro Thr Asn Gly Pro Leu Pro Glu Asp Asn Glu Pro Ser
65                  70                  75                  80

Ala Tyr Ala Gln Leu Asp Cys Val Leu Glu Ala Leu Asp Arg Met Asp
                85                  90                  95

Glu Glu His Pro Gly Leu Phe Gln Ala Ala Ser Gln Asn Ala Met Glu
            100                 105                 110

Ala Leu Met Val Thr Thr Val Asp Lys Leu Thr Gln Gly Arg Gln Thr
        115                 120                 125

Phe Asp Trp Thr Val Cys Arg Asn Gln Pro Ala Ala Thr Ala Leu Asn
    130                 135                 140

Thr Thr Ile Thr Ser Phe Arg Leu Asn Asp Leu Asn Gly Ala Asp Lys
145                 150                 155                 160

Gly Gly Leu Val Pro Phe Cys Gln Asp Ile Ile Asp Ser Leu Asp Lys
                165                 170                 175

Pro Glu Met Thr Phe Phe Ser Val Lys Asn Ile Lys Lys Lys Leu Pro
            180                 185                 190

Ala Lys Asn Arg Lys Gly Phe Leu Ile Lys Arg Ile Pro Met Lys Val
        195                 200                 205

Lys Asp Arg Ile Ser Arg Val Glu Tyr Ile Lys Arg Ala Leu Ser Leu
    210                 215                 220

Asn Thr Met Thr Lys Asp Ala Glu Arg Gly Lys Leu Lys Arg Arg Ala
225                 230                 235                 240

Ile Ala Thr Ala Gly Ile Gln Ile Arg Gly Phe Val Leu Val Val Glu
                245                 250                 255

Asn Leu Ala Lys Asn Ile Cys Glu Asn Leu Glu Gln Ser Gly Leu Pro
            260                 265                 270

Val Gly Gly Asn Glu Lys Lys Ala Lys Leu Ser Asn Ala Val Ala Lys
        275                 280                 285
```

-continued

```
Met Leu Ser Asn Cys Pro Pro Gly Gly Ile Ser Met Thr Val Thr Gly
    290                 295                 300

Asp Asn Thr Lys Trp Asn Glu Cys Leu Asn Pro Arg Ile Phe Leu Ala
305                 310                 315                 320

Met Thr Glu Arg Ile Thr Arg Asp Ser Pro Ile Trp Phe Arg Asp Phe
                325                 330                 335

Cys Ser Ile Ala Pro Val Leu Phe Ser Asn Lys Ile Ala Arg Leu Gly
            340                 345                 350

Lys Gly Phe Met Ile Thr Ser Lys Thr Lys Arg Leu Lys Ala Gln Ile
        355                 360                 365

Pro Cys Pro Asp Leu Phe Ser Ile Pro Leu Glu Arg Tyr Asn Glu Glu
    370                 375                 380

Thr Arg Ala Lys Leu Lys Lys Leu Lys Pro Phe Phe Asn Glu Glu Gly
385                 390                 395                 400

Thr Ala Ser Leu Ser Pro Gly Met Met Met Gly Met Phe Asn Met Leu
                405                 410                 415

Ser Thr Val Leu Gly Val Ala Ala Leu Gly Ile Lys Asn Ile Gly Asn
            420                 425                 430

Lys Glu Tyr Leu Trp Asp Gly Leu Gln Ser Ser Asp Asp Phe Ala Leu
        435                 440                 445

Phe Val Asn Ala Lys Asp Glu Glu Thr Cys Met Glu Gly Ile Asn Asp
    450                 455                 460

Phe Tyr Arg Thr Cys Lys Leu Leu Gly Ile Asn Met Ser Lys Lys Lys
465                 470                 475                 480

Ser Tyr Cys Asn Glu Thr Gly Met Phe Glu Phe Thr Ser Met Phe Tyr
                485                 490                 495

Arg Asp Gly Phe Val Ser Asn Phe Ala Met Glu Ile Pro Ser Phe Gly
            500                 505                 510

Val Ala Gly Val Asn Glu Ser Ala Asp Met Ala Ile Gly Met Thr Ile
        515                 520                 525

Ile Lys Asn Asn Met Ile Asn Asn Gly Met Gly Pro Ala Thr Ala Gln
    530                 535                 540

Thr Ala Ile Gln Leu Phe Ile Ala Asp Tyr Arg Tyr Thr Tyr Lys Cys
545                 550                 555                 560

His Arg Gly Asp Ser Lys Val Glu Gly Lys Arg Met Lys Ile Ile Lys
                565                 570                 575

Glu Leu Trp Glu Asn Thr Lys Gly Arg Asp Gly Leu Leu Val Ala Asp
            580                 585                 590

Gly Gly Pro Asn Ile Tyr Asn Leu Arg Asn Leu His Ile Pro Glu Ile
        595                 600                 605

Val Leu Lys Tyr Asn Leu Met Asp Pro Glu Tyr Lys Gly Arg Leu Leu
    610                 615                 620

His Pro Gln Asn Pro Phe Val Gly His Leu Ser Ile Glu Gly Ile Lys
625                 630                 635                 640

Glu Ala Asp Ile Thr Pro Ala His Gly Pro Val Lys Lys Met Asp Tyr
                645                 650                 655

Asp Ala Val Ser Gly Thr His Ser Trp Arg Thr Lys Arg Asn Arg Ser
            660                 665                 670

Ile Leu Asn Thr Asp Gln Arg Asn Met Ile Leu Glu Glu Gln Cys Tyr
        675                 680                 685

Ala Lys Cys Cys Asn Leu Phe Glu Ala Cys Phe Asn Ser Ala Ser Tyr
    690                 695                 700

Arg Lys Pro Val Gly Gln His Ser Met Leu Glu Ala Met Ala His Arg
```

705 710 715 720

Leu Arg Met Asp Ala Arg Leu Asp Tyr Glu Ser Gly Arg Met Ser Lys
725 730 735

Asp Asp Phe Glu Lys Ala Met Ala His Leu Gly Glu Ile Gly Tyr Thr
740 745 750

<210> SEQ ID NO 187
<211> LENGTH: 770
<212> TYPE: PRT
<213> ORGANISM: Influenza B virus
<220> FEATURE:
<221> NAME/KEY: misc_feature
<222> LOCATION: (1)..(770)
<223> OTHER INFORMATION: Influenza B pb2 Protein

<400> SEQUENCE: 187

Met Thr Leu Ala Lys Ile Glu Leu Leu Lys Gln Leu Leu Arg Asp Asn
1 5 10 15

Glu Ala Lys Thr Val Leu Lys Gln Thr Thr Val Asp Gln Tyr Asn Ile
20 25 30

Ile Arg Lys Phe Asn Thr Ser Arg Ile Glu Lys Asn Pro Ser Leu Arg
35 40 45

Met Lys Trp Ala Met Cys Ser Asn Phe Pro Leu Ala Leu Thr Lys Gly
50 55 60

Asp Met Ala Asn Arg Ile Pro Leu Glu Tyr Lys Gly Ile Gln Leu Lys
65 70 75 80

Thr Asn Ala Glu Asp Ile Gly Thr Lys Gly Gln Met Cys Ser Ile Ala
85 90 95

Ala Val Thr Trp Trp Asn Thr Tyr Gly Pro Ile Gly Asp Thr Glu Gly
100 105 110

Phe Glu Lys Val Tyr Glu Ser Phe Phe Leu Arg Lys Met Arg Leu Asp
115 120 125

Asn Ala Thr Trp Gly Arg Ile Thr Phe Gly Pro Val Glu Arg Val Arg
130 135 140

Lys Arg Val Leu Leu Asn Pro Leu Thr Lys Glu Met Pro Pro Asp Glu
145 150 155 160

Ala Ser Asn Val Ile Met Glu Ile Leu Phe Pro Lys Glu Ala Gly Ile
165 170 175

Pro Arg Glu Ser Thr Trp Ile His Arg Glu Leu Ile Lys Glu Lys Arg
180 185 190

Glu Lys Leu Lys Gly Thr Met Ile Thr Pro Ile Val Leu Ala Tyr Met
195 200 205

Leu Glu Arg Glu Leu Val Ala Arg Arg Arg Phe Leu Pro Val Ala Gly
210 215 220

Ala Thr Ser Ala Glu Phe Ile Glu Met Leu His Cys Leu Gln Gly Glu
225 230 235 240

Asn Trp Arg Gln Ile Tyr His Pro Gly Gly Asn Lys Leu Thr Glu Ser
245 250 255

Arg Ser Gln Ser Met Ile Val Ala Cys Arg Lys Ile Ile Arg Arg Ser
260 265 270

Ile Val Ala Ser Asn Pro Leu Glu Leu Ala Val Glu Ile Ala Asn Lys
275 280 285

Thr Val Ile Asp Thr Glu Pro Leu Lys Ser Cys Leu Thr Ala Ile Asp
290 295 300

Gly Gly Asp Val Ala Cys Asp Ile Ile Arg Ala Ala Leu Gly Leu Lys
305 310 315 320

-continued

```
Ile Arg Gln Arg Gln Arg Phe Gly Arg Leu Glu Leu Lys Arg Ile Ser
                325                 330                 335

Gly Arg Gly Phe Lys Asn Asp Glu Glu Ile Leu Ile Gly Asn Gly Thr
            340                 345                 350

Ile Gln Lys Ile Gly Ile Trp Asp Gly Glu Glu Glu Phe His Val Arg
        355                 360                 365

Cys Gly Glu Cys Arg Gly Ile Leu Lys Lys Ser Lys Met Arg Met Glu
    370                 375                 380

Lys Leu Leu Ile Asn Ser Ala Lys Lys Glu Asp Met Lys Asp Leu Ile
385                 390                 395                 400

Ile Leu Cys Met Val Phe Ser Gln Asp Thr Arg Met Phe Gln Gly Val
                405                 410                 415

Arg Gly Glu Ile Asn Phe Leu Asn Arg Ala Gly Gln Leu Leu Ser Pro
            420                 425                 430

Met Tyr Gln Leu Gln Arg Tyr Phe Leu Ser Arg Ser Asn Asp Leu Phe
        435                 440                 445

Asp Gln Trp Gly Tyr Glu Glu Ser Pro Lys Ala Ser Glu Leu His Gly
    450                 455                 460

Ile Asn Glu Leu Met Asn Ala Ser Asp Tyr Thr Leu Lys Gly Val Val
465                 470                 475                 480

Val Thr Lys Asn Val Ile Asp Asp Phe Ser Ser Thr Glu Thr Glu Lys
                485                 490                 495

Val Ser Ile Thr Lys Asn Leu Ser Leu Ile Lys Arg Thr Gly Glu Val
            500                 505                 510

Ile Met Gly Ala Asn Asp Val Ser Glu Leu Glu Ser Gln Ala Gln Leu
        515                 520                 525

Met Ile Thr Tyr Asp Thr Pro Lys Met Trp Glu Met Gly Thr Thr Lys
    530                 535                 540

Glu Leu Val Gln Asn Thr Tyr Gln Trp Val Leu Lys Asn Leu Val Thr
545                 550                 555                 560

Leu Lys Ala Gln Phe Leu Leu Gly Lys Glu Asp Met Phe Gln Trp Asp
                565                 570                 575

Ala Phe Glu Ala Phe Glu Ser Ile Ile Pro Gln Lys Met Ala Gly Gln
            580                 585                 590

Tyr Ser Gly Phe Ala Arg Ala Val Leu Lys Gln Met Arg Asp Gln Glu
        595                 600                 605

Val Met Lys Thr Asp Gln Phe Ile Lys Leu Leu Pro Phe Cys Phe Ser
    610                 615                 620

Pro Pro Lys Leu Arg Ser Asn Gly Glu Pro Tyr Gln Phe Leu Arg Leu
625                 630                 635                 640

Val Leu Lys Gly Gly Gly Glu Asn Phe Ile Glu Val Arg Lys Gly Ser
                645                 650                 655

Pro Leu Phe Ser Tyr Asn Pro Gln Thr Glu Val Leu Thr Ile Cys Gly
            660                 665                 670

Arg Met Met Ser Leu Lys Gly Lys Ile Glu Asp Glu Glu Arg Asn Arg
        675                 680                 685

Ser Met Gly Asn Ala Val Leu Ala Gly Phe Leu Val Ser Gly Lys Tyr
    690                 695                 700

Asp Pro Asp Leu Gly Asp Phe Lys Thr Ile Glu Glu Leu Glu Lys Leu
705                 710                 715                 720

Lys Pro Gly Glu Lys Ala Asn Ile Leu Leu Tyr Gln Gly Lys Pro Val
                725                 730                 735
```

Lys Val Val Lys Arg Lys Arg Tyr Ser Ala Leu Ser Asn Asp Ile Ser
740 745 750

Gln Gly Ile Lys Arg Gln Arg Met Thr Val Glu Ser Met Gly Trp Ala
755 760 765

Leu Ser
770

<210> SEQ ID NO 188
<211> LENGTH: 252
<212> TYPE: PRT
<213> ORGANISM: Influenza B virus
<220> FEATURE:
<221> NAME/KEY: misc_feature
<222> LOCATION: (1)..(252)
<223> OTHER INFORMATION: H1N1 M Protein

<400> SEQUENCE: 188

Met Ser Leu Leu Thr Glu Val Glu Thr Tyr Val Leu Ser Ile Ile Pro
1 5 10 15

Ser Gly Pro Leu Lys Ala Glu Ile Ala Gln Arg Leu Glu Ser Val Phe
20 25 30

Ala Gly Lys Asn Thr Asp Leu Glu Ala Leu Met Glu Trp Leu Lys Thr
35 40 45

Arg Pro Ile Leu Ser Pro Leu Thr Lys Gly Ile Leu Gly Phe Val Phe
50 55 60

Thr Leu Thr Val Pro Ser Glu Arg Gly Leu Gln Arg Arg Arg Phe Ile
65 70 75 80

Gln Asn Ala Leu Asn Gly Asn Gly Asp Pro Asn Asn Met Asp Arg Ala
85 90 95

Val Lys Leu Tyr Lys Lys Leu Lys Arg Glu Ile Thr Phe His Gly Ala
100 105 110

Lys Glu Val Ser Leu Ser Tyr Ser Thr Gly Ala Leu Ala Ser Cys Met
115 120 125

Gly Leu Ile Tyr Asn Arg Met Gly Thr Val Thr Thr Glu Ala Ala Phe
130 135 140

Gly Leu Val Cys Ala Thr Cys Glu Gln Ile Ala Asp Ser Gln His Arg
145 150 155 160

Ser His Arg Gln Met Ala Thr Thr Thr Asn Pro Leu Ile Arg His Glu
165 170 175

Asn Arg Met Val Leu Ala Ser Thr Thr Ala Lys Ala Met Glu Gln Val
180 185 190

Ala Gly Ser Ser Glu Gln Ala Ala Glu Ala Met Glu Val Ala Asn Gln
195 200 205

Thr Arg Gln Met Val His Ala Met Arg Thr Ile Gly Thr His Pro Ser
210 215 220

Ser Ser Ala Gly Leu Arg Asp Asp Leu Leu Glu Asn Leu Gln Ala Tyr
225 230 235 240

Gln Lys Arg Met Gly Val Gln Met Gln Arg Phe Lys
245 250

<210> SEQ ID NO 189
<211> LENGTH: 219
<212> TYPE: PRT
<213> ORGANISM: Influenza A virus
<220> FEATURE:
<221> NAME/KEY: misc_feature
<222> LOCATION: (1)..(219)
<223> OTHER INFORMATION: H1N1 ns1 Protein

<400> SEQUENCE: 189

Met Asp Ser Asn Thr Met Ser Ser Phe Gln Val Asp Cys Phe Leu Trp
1 5 10 15

His Ile Arg Lys Arg Phe Ala Asp Asn Gly Leu Gly Asp Ala Pro Phe
20 25 30

Leu Asp Arg Leu Arg Arg Asp Gln Lys Ser Leu Lys Gly Arg Gly Asn
35 40 45

Thr Leu Gly Leu Asp Ile Glu Thr Ala Thr Leu Val Gly Lys Gln Ile
50 55 60

Val Glu Trp Ile Leu Lys Glu Glu Ser Ser Glu Thr Leu Arg Met Thr
65 70 75 80

Ile Ala Ser Val Pro Thr Ser Arg Tyr Leu Ser Asp Met Thr Leu Glu
85 90 95

Glu Met Ser Arg Asp Trp Phe Met Leu Met Pro Arg Gln Lys Ile Ile
100 105 110

Gly Pro Leu Cys Val Arg Leu Asp Gln Ala Ile Met Glu Lys Asn Ile
115 120 125

Val Leu Lys Ala Asn Phe Ser Val Ile Phe Asn Arg Leu Glu Thr Leu
130 135 140

Ile Leu Leu Arg Ala Phe Thr Glu Glu Gly Ala Ile Val Gly Glu Ile
145 150 155 160

Ser Pro Leu Pro Ser Leu Pro Gly His Thr Tyr Glu Asp Val Lys Asn
165 170 175

Ala Val Gly Val Leu Ile Gly Gly Leu Glu Trp Asn Gly Asn Thr Val
180 185 190

Arg Val Ser Glu Asn Ile Gln Arg Phe Ala Trp Arg Asn Cys Asp Glu
195 200 205

Asn Gly Arg Pro Ser Leu Pro Pro Glu Gln Lys
210 215

<210> SEQ ID NO 190
<211> LENGTH: 716
<212> TYPE: PRT
<213> ORGANISM: Influenza A virus
<220> FEATURE:
<221> NAME/KEY: misc_feature
<222> LOCATION: (1)..(716)
<223> OTHER INFORMATION: H1N1 pa Protein

<400> SEQUENCE: 190

Met Glu Gly Phe Val Arg Gln Cys Phe Asn Pro Met Ile Val Glu Leu
1 5 10 15

Ala Glu Lys Ala Met Lys Glu Tyr Gly Glu Asp Pro Lys Ile Glu Thr
20 25 30

Asn Lys Phe Ala Ala Ile Cys Thr His Leu Glu Val Cys Phe Met Tyr
35 40 45

Ser Asp Phe His Phe Ile Asp Glu Arg Gly Glu Ser Ile Ile Val Glu
50 55 60

Ser Gly Asp Pro Asn Ala Leu Leu Lys His Arg Phe Glu Ile Ile Glu
65 70 75 80

Gly Arg Asp Arg Ile Met Ala Trp Thr Val Val Asn Ser Ile Cys Asn
85 90 95

Thr Thr Gly Val Glu Lys Pro Lys Phe Leu Pro Asp Leu Tyr Asp Tyr
100 105 110

Lys Glu Asn Arg Phe Ile Glu Ile Gly Val Thr Arg Arg Glu Val His
115 120 125

```
Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Ser Leu Trp Asp Ser Phe Arg
            180                 185                 190

Gln Ser Glu Arg Gly Glu Glu Thr Ile Glu Glu Lys Phe Glu Ile Thr
        195                 200                 205

Gly Thr Met Arg Lys Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Lys
                245                 250                 255

Ile Glu Pro Phe Leu Arg Thr Thr Pro Arg Pro Leu Arg Leu Pro Asp
            260                 265                 270

Gly Pro Leu Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Asn Ile Val Lys Pro His Glu Lys Gly Ile Asn Pro Asn Tyr Leu Met
                325                 330                 335

Thr Trp Lys Gln Val Leu Ala Glu Leu Gln Asp Ile Glu Asn Glu Glu
            340                 345                 350

Lys Ile Pro Arg Thr Lys Asn Met Lys Arg Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Pro
385                 390                 395                 400

Arg Ser Leu Ala Ser Trp Val Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540
```

Ile Gly Asp Met Leu Leu Arg Thr Ala Ile Gly Gln Val Ser Arg Pro
545 550 555 560

Met Phe Leu Tyr Val Arg Thr Asn Gly Thr Ser Lys Ile Lys Met Lys
565 570 575

Trp Gly Met Glu Met Arg Arg Cys Leu Leu Gln Ser Leu Gln Gln Ile
580 585 590

Glu Ser Met Ile Glu Ala Glu Ser Ser Val Lys Glu Lys Asp Met Thr
595 600 605

Lys Glu Phe Phe Glu Asn Lys Ser Glu Thr Trp Pro Ile Gly Glu Ser
610 615 620

Pro Arg Gly Val Glu Glu Gly Ser Ile Gly Lys Val Cys Arg Thr Leu
625 630 635 640

Leu Ala Lys Ser Val Phe Asn Ser Leu Tyr Ala Ser Pro Gln Leu Glu
645 650 655

Gly Phe Ser Ala Glu Ser Arg Lys Leu Leu Leu Ile Val Gln Ala Leu
660 665 670

Arg Asp Asn Leu Glu Pro Gly Thr Phe Asp Leu Gly Gly Leu Tyr Glu
675 680 685

Ala Ile Glu Glu Cys Leu Ile Asn Asp Pro Trp Val Leu Leu Asn Ala
690 695 700

Ser Trp Phe Asn Ser Phe Leu Thr His Ala Leu Lys
705 710 715

<210> SEQ ID NO 191
<211> LENGTH: 757
<212> TYPE: PRT
<213> ORGANISM: Influenza A virus
<220> FEATURE:
<221> NAME/KEY: misc_feature
<222> LOCATION: (1)..(757)
<223> OTHER INFORMATION: H1N1 pb1 Protein

<400> SEQUENCE: 191

Met Asp Val Asn Pro Thr Leu Leu Phe Leu Lys Ile Pro Ala Gln Asn
1 5 10 15

Ala Ile Ser Thr Thr Phe Pro Tyr Thr Gly Asp Pro Pro Tyr Ser His
20 25 30

Gly Thr Gly Thr Gly Tyr Thr Met Asp Thr Val Asn Arg Thr His Gln
35 40 45

Tyr Ser Glu Lys Gly Lys Trp Thr Thr Asn Thr Glu Thr Gly Ala Pro
50 55 60

Gln Leu Asn Pro Ile Asp Gly Pro Leu Pro Glu Asp Asn Glu Pro Ser
65 70 75 80

Gly Tyr Ala Gln Thr Asp Cys Val Leu Glu Ala Met Ala Phe Leu Glu
85 90 95

Glu Ser His Pro Gly Ile Phe Glu Asn Ser Cys Leu Glu Thr Met Glu
100 105 110

Val Val Gln Gln Thr Arg Val Asp Lys Leu Thr Gln Gly Arg Gln Thr
115 120 125

Tyr Asp Trp Thr Leu Asn Arg Asn Gln Pro Ala Ala Thr Ala Leu Ala
130 135 140

Asn Thr Ile Glu Val Phe Arg Ser Asn Gly Leu Thr Ala Asn Glu Ser
145 150 155 160

Gly Arg Leu Ile Asp Phe Leu Lys Asp Val Met Glu Ser Met Asn Lys
165 170 175

Glu Glu Ile Glu Ile Thr Thr His Phe Gln Arg Lys Arg Arg Val Arg

-continued

```
            180                 185                 190

Asp Asn Met Thr Lys Lys Met Val Thr Gln Arg Thr Ile Gly Lys Lys
        195                 200                 205

Lys Gln Arg Leu Asn Lys Arg Gly Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Ile Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Ile
                325                 330                 335

Leu Ser Met Ala Pro Ile Met Phe Ser Asn Lys Met Ala Arg Leu Gly
            340                 345                 350

Arg Gly Tyr Met Phe Glu Ser Lys Arg Met Lys Ile Arg Thr Gln Ile
        355                 360                 365

Pro Ala Glu Met Leu Ala Ser Ile Asp Leu Lys Tyr Phe Asn Glu Ser
    370                 375                 380

Thr Lys Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Lys Thr Ile Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Lys Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Val Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Asp Gln Thr Gln Ser Lys Val Gly Leu Leu Val Ser
            580                 585                 590

Asp Gly Gly Pro Asn Leu Tyr Asn Ile Arg Asn Leu His Ile Pro Glu
        595                 600                 605
```

Val Cys Leu Lys Trp Glu Leu Met Asp Asp Asp Tyr Arg Gly Arg Leu
610 615 620

Cys Asn Pro Leu Asn Pro Phe Val Ser His Lys Glu Ile Asp Ser Val
625 630 635 640

Asn Asn Ala Val Val Met Pro Ala His Gly Pro Ala Lys Ser Met Glu
645 650 655

Tyr Asp Ala Val Ala Thr Thr His Ser Trp Ile Pro Lys Arg Asn Arg
660 665 670

Ser Ile Leu Asn Thr Ser Gln Arg Gly Ile Leu Glu Asp Glu Gln Met
675 680 685

Tyr Gln Lys Cys Cys Asn Leu Phe Glu Lys Phe Phe Pro Ser Ser Ser
690 695 700

Tyr Arg Arg Pro Val Gly Ile Ser Ser Met Val Glu Ala Met Val Ser
705 710 715 720

Arg Ala Arg Ile Asp Ala Arg Val Asp Phe Glu Ser Gly Arg Ile Lys
725 730 735

Lys Glu Glu Phe Ser Glu Ile Met Lys Ile Cys Ser Thr Ile Glu Glu
740 745 750

Leu Arg Arg Gln Lys
755

<210> SEQ ID NO 192
<211> LENGTH: 446
<212> TYPE: PRT
<213> ORGANISM: Influenza A virus
<220> FEATURE:
<221> NAME/KEY: misc_feature
<222> LOCATION: (1)..(446)
<223> OTHER INFORMATION: H1N1 pb2 Protein

<400> SEQUENCE: 192

Ala Met Gly Leu Arg Ile Ser Ser Ser Phe Ser Phe Gly Gly Phe Thr
1 5 10 15

Phe Lys Arg Thr Ser Gly Ser Ser Val Lys Arg Glu Glu Glu Val Leu
20 25 30

Thr Gly Asn Leu Gln Thr Leu Lys Leu Thr Val His Glu Gly Tyr Glu
35 40 45

Glu Phe Thr Met Val Gly Lys Arg Ala Thr Ala Ile Leu Arg Lys Ala
50 55 60

Thr Arg Arg Leu Ile Gln Leu Ile Val Ser Gly Arg Asp Glu Gln Ser
65 70 75 80

Ile Val Glu Ala Ile Val Val Ala Met Val Phe Ser Gln Glu Asp Cys
85 90 95

Met Val Lys Ala Val Arg Gly Asp Leu Asn Phe Val Asn Arg Ala Asn
100 105 110

Gln Arg Leu Asn Pro Met His Gln Leu Leu Arg His Phe Gln Lys Asp
115 120 125

Ala Lys Val Leu Phe Leu Asn Trp Gly Val Glu Pro Ile Asp Asn Val
130 135 140

Met Gly Met Ile Gly Ile Leu Pro Asp Met Thr Pro Ser Thr Glu Met
145 150 155 160

Ser Met Arg Gly Val Arg Val Ser Lys Met Gly Val Asp Glu Tyr Ser
165 170 175

Asn Ala Glu Arg Val Val Val Ser Ile Asp Arg Phe Leu Arg Val Arg
180 185 190

Asp Gln Arg Gly Asn Val Leu Leu Ser Pro Glu Glu Val Ser Glu Thr
195 200 205

Gln Gly Thr Glu Lys Leu Thr Ile Thr Tyr Ser Ser Ser Met Met Trp
210 215 220

Glu Ile Asn Gly Pro Glu Ser Val Leu Ile Asn Thr Tyr Gln Trp Ile
225 230 235 240

Ile Arg Asn Trp Glu Thr Val Lys Ile Gln Trp Ser Gln Asn Pro Thr
245 250 255

Met Leu Tyr Asn Lys Met Glu Phe Glu Pro Phe Gln Ser Leu Val Pro
260 265 270

Lys Ala Ile Arg Gly Gln Tyr Ser Gly Phe Val Arg Thr Leu Phe Gln
275 280 285

Gln Met Arg Asp Val Leu Gly Thr Phe Asp Thr Thr Gln Ile Ile Lys
290 295 300

Leu Leu Pro Phe Ala Ala Ala Pro Pro Lys Gln Ser Arg Met Gln Phe
305 310 315 320

Ser Ser Leu Thr Val Asn Val Arg Gly Ser Gly Met Lys Ile Leu Val
325 330 335

Arg Gly Asn Ser Pro Val Phe Asn Tyr Asn Lys Thr Thr Lys Arg Leu
340 345 350

Thr Val Leu Gly Lys Asp Ala Gly Thr Leu Thr Glu Asp Pro Asp Glu
355 360 365

Gly Thr Ala Gly Val Glu Ser Ala Val Leu Arg Gly Phe Leu Ile Leu
370 375 380

Gly Lys Glu Asp Arg Arg Tyr Gly Pro Ala Leu Ser Ile Asn Glu Leu
385 390 395 400

Ser Asn Leu Ala Lys Gly Glu Lys Ala Asn Val Leu Ile Gly Gln Gly
405 410 415

Asp Val Val Leu Val Met Lys Arg Lys Arg Asp Ser Ser Ile Leu Thr
420 425 430

Asp Ser Gln Thr Ala Thr Lys Arg Ile Arg Met Ala Ile Asn
435 440 445

<210> SEQ ID NO 193
<211> LENGTH: 121
<212> TYPE: PRT
<213> ORGANISM: Influenza A virus
<220> FEATURE:
<221> NAME/KEY: misc_feature
<222> LOCATION: (1)..(121)
<223> OTHER INFORMATION: H1N1 NS2 Protein

<400> SEQUENCE: 193

Met Asp Ser Asn Thr Met Ser Ser Phe Gln Asp Ile Leu Met Arg Met
1 5 10 15

Ser Lys Met Gln Leu Gly Ser Ser Ser Glu Asp Leu Asn Gly Met Val
20 25 30

Thr Arg Phe Glu Ser Leu Lys Ile Tyr Arg Asp Ser Leu Gly Glu Thr
35 40 45

Val Met Arg Met Gly Asp Leu His Tyr Leu Gln Ser Arg Asn Glu Lys
50 55 60

Trp Arg Glu Gln Leu Gly Gln Lys Phe Glu Glu Ile Arg Trp Leu Ile
65 70 75 80

Glu Glu Met Arg His Arg Leu Lys Ala Thr Glu Asn Ser Phe Glu Gln
85 90 95

Ile Thr Phe Met Gln Ala Leu Gln Leu Leu Leu Glu Val Glu Gln Glu

-continued

```
            100                 105                 110

Ile Arg Ala Phe Ser Phe Gln Leu Ile
        115                 120


<210> SEQ ID NO 194
<211> LENGTH: 13
<212> TYPE: PRT
<213> ORGANISM: Influenza B virus

<400> SEQUENCE: 194

Val Lys Thr Ala Thr Gln Gly Glu Val Asn Val Thr Gly
1               5                   10
```